(12) United States Patent
Kobayashi et al.

(10) Patent No.: US 10,912,683 B2
(45) Date of Patent: Feb. 9, 2021

(54) SHEET-SHAPED OBJECT AND METHOD FOR PRODUCING SHEET-SHAPED OBJECT

(71) Applicant: KAO CORPORATION, Tokyo (JP)

(72) Inventors: Kenji Kobayashi, Utsunomiya (JP); Bin Latif Muhamad Nor Salehuddin, Utsunomiya (JP); Ryota Kuramae, Utsunomiya (JP); Aiko Onda, Utsunomiya (JP)

(73) Assignee: KAO CORPORATION, Tokyo (JP)

( * ) Notice: Subject to any disclaimer, the term of this patent is extended or adjusted under 35 U.S.C. 154(b) by 182 days.

(21) Appl. No.: 15/766,609

(22) PCT Filed: Oct. 6, 2016

(86) PCT No.: PCT/JP2016/079845
§ 371 (c)(1),
(2) Date: Apr. 6, 2018

(87) PCT Pub. No.: WO2017/061568
PCT Pub. Date: Apr. 13, 2017

(65) Prior Publication Data
US 2018/0296403 A1    Oct. 18, 2018

(30) Foreign Application Priority Data

Oct. 7, 2015  (JP) .................................. 2015-199376
Dec. 15, 2015  (JP) .................................. 2015-243767

(51) Int. Cl.
*A61F 13/531*    (2006.01)
*A61F 13/539*    (2006.01)
(Continued)

(52) U.S. Cl.
CPC ...... *A61F 13/531* (2013.01); *A61F 13/15658* (2013.01); *A61F 13/15707* (2013.01);
(Continued)

(58) Field of Classification Search
CPC ............. A61F 13/531; A61F 13/15707; A61F 13/15658; A61F 13/532; A61F 13/539;
(Continued)

(56) References Cited

U.S. PATENT DOCUMENTS 5,397,316 A  *  3/1995  LaVon ................ A61F 13/535
                                                    604/369
5,713,881 A      2/1998  Rezai et al.
(Continued)

FOREIGN PATENT DOCUMENTS

CN    1297346 A    5/2001
CN    1376045 A    10/2002
(Continued)

OTHER PUBLICATIONS

International Search Report (PCT/ISA/210) issued in PCT/JP2016/079845, dated Jan. 10, 2017.
(Continued)

*Primary Examiner* — Michael N Orlando
*Assistant Examiner* — Christopher W Raimund
(74) *Attorney, Agent, or Firm* — Birch, Stewart, Kolasch & Birch, LLP

(57) ABSTRACT

A sheet-like article (1) for an absorbent article of the invention includes a plurality of absorbent units (4), each including: a long base portion (2); and water-absorbent polymer particles (3) that are fixed to a surface of first side of the long base portion (2). In the sheet-like article (1), the absorbent units (4) are arranged such that the longitudinal direction thereof is oriented in one direction. When the water-absorbent polymer particles (3) absorb a liquid, the water-absorbent polymer particles (3) swell beyond the lateral side edge portions (2s), of the long base portion (2), that extend along the longitudinal direction, and a position,
(Continued)

in the thickness direction, of each long base portion is varied from the position thereof before absorbing the liquid.

15 Claims, 15 Drawing Sheets

(51) Int. Cl.
| | |
|---|---|
| A61F 13/532 | (2006.01) |
| A61F 13/15 | (2006.01) |
| A61F 13/49 | (2006.01) |
| A61F 13/494 | (2006.01) |
| B32B 5/02 | (2006.01) |
| B32B 5/16 | (2006.01) |
| B32B 7/12 | (2006.01) |
| B32B 37/12 | (2006.01) |
| B32B 38/00 | (2006.01) |
| A61F 13/534 | (2006.01) |
| A61F 13/53 | (2006.01) |

(52) U.S. Cl.
CPC .. *A61F 13/15723* (2013.01); *A61F 13/15739* (2013.01); *A61F 13/49011* (2013.01); *A61F 13/49413* (2013.01); *A61F 13/532* (2013.01); *A61F 13/539* (2013.01); *B32B 5/022* (2013.01); *B32B 5/16* (2013.01); *B32B 7/12* (2013.01); *B32B 37/12* (2013.01); *B32B 38/0004* (2013.01); *A61F 13/15764* (2013.01); *A61F 2013/4948* (2013.01); *A61F 2013/49093* (2013.01); *A61F 2013/5315* (2013.01); *A61F 2013/5349* (2013.01); *A61F 2013/530189* (2013.01); *A61F 2013/530226* (2013.01); *A61F 2013/530233* (2013.01); *A61F 2013/530299* (2013.01); *A61F 2013/530868* (2013.01); *B32B 2307/726* (2013.01); *B32B 2555/02* (2013.01)

(58) Field of Classification Search
CPC .......... A61F 13/49413; A61F 13/49011; A61F 13/15739; A61F 13/15723; A61F 2013/5349; A61F 2013/5315; A61F 2013/530868; A61F 2013/530299; A61F 2013/530233; A61F 2013/530226; A61F 2013/530189; A61F 2013/4948; A61F 2013/49093; A61F 13/15764; A61F 2013/530481; A61F 2013/1591; A61F 13/534; A61F 13/53; A61F 13/49017; A61F 13/15666; A61F 13/15617; A61F 13/15; B32B 38/0004; B32B 37/12; B32B 7/12; B32B 5/16; B32B 5/022; B32B 2555/02; B32B 2307/726

See application file for complete search history.

(56) References Cited

U.S. PATENT DOCUMENTS

| | | |
|---|---|---|
| 5,977,014 A | 11/1999 | Plischke et al. |
| 6,203,654 B1 | 3/2001 | McFall et al. |
| 6,344,036 B1 * | 2/2002 | Ivansson ........... A61F 13/53717 |
| | | 604/369 |
| 6,972,011 B2 * | 12/2005 | Maeda ............. A61F 13/15658 |
| | | 602/41 |
| 8,772,570 B2 | 7/2014 | Kawakami et al. |
| 2003/0163106 A1 | 8/2003 | Blaney et al. |
| 2004/0127874 A1 | 7/2004 | Nishizawa et al. |
| 2004/0158212 A1 * | 8/2004 | Ponomarenko ... A61F 13/15203 |
| | | 604/367 |
| 2005/0096615 A1 * | 5/2005 | Kuen .................... A61F 13/536 |
| | | 604/385.01 |
| 2006/0206091 A1 | 9/2006 | Cole et al. |
| 2009/0062760 A1 * | 3/2009 | Wright ............. A61F 13/15723 |
| | | 604/367 |
| 2009/0088718 A1 * | 4/2009 | Toyoshima ....... A61F 13/49011 |
| | | 604/385.23 |
| 2011/0208147 A1 | 8/2011 | Kawakami et al. |
| 2012/0035565 A1 | 2/2012 | Okawa et al. |

FOREIGN PATENT DOCUMENTS

| | | |
|---|---|---|
| EP | 0 293 208 A1 | 11/1988 |
| EP | 1862156 A1 | 12/2007 |
| JP | 63-18122 U | 2/1988 |
| JP | 1-87720 U | 6/1989 |
| JP | 10-508528 A | 8/1998 |
| JP | 11-170414 A | 6/1999 |
| JP | 2002-224162 A | 8/2002 |
| JP | 2003-265525 A | 9/2003 |
| JP | 2006-341061 A | 12/2006 |
| JP | 2010-104523 A | 5/2010 |
| JP | 2011-136033 A | 7/2011 |
| JP | 2013-39804 A | 2/2013 |
| JP | 2015-42244 A | 3/2015 |
| JP | 2017-70496 A | 4/2017 |
| JP | 2017-70497 A | 4/2017 |
| JP | 2017-70498 A | 4/2017 |
| JP | 2017-70499 A | 4/2017 |
| JP | 2017-70501 A | 4/2017 |
| KR | 2002-0027651 A | 4/2002 |
| KR | 10-2007-0113196 A | 11/2007 |
| KR | 10-2011-0139682 A | 12/2011 |
| WO | WO 99/42068 A1 | 8/1999 |
| WO | WO 01/19311 A1 | 3/2001 |

OTHER PUBLICATIONS

European Patent Office Communication and extended search report issued in the corresponding European Patent Application No. 16853719.9 dated May 10, 2019.

* cited by examiner

SHEET-SHAPED OBJECT AND METHOD FOR PRODUCING SHEET-SHAPED OBJECT

TECHNICAL FIELD

The present invention relates to a sheet-like article to be used in an absorbent article and a method for manufacturing the sheet-like article. The invention also relates to an absorbent article such as a disposable diaper.

BACKGROUND ART

Absorbent members used in absorbent articles, such as disposable diapers, sanitary napkins, and incontinence pads, are generally manufactured by: carrying, on an airflow, a material for the absorbent member including pulp fiber and a water-absorbent polymer, and sucking and depositing the material in a depression formed in the outer circumferential surface of a rotary drum; and then covering the fiber stack having accumulated in the depression with a water-permeable sheet material. The weight of the water-absorbent polymer, however, is considerably heavier than the weight of the pulp fiber. Thus, dispersion of the water-absorbent polymer tends to become nonuniform. In such nonuniform absorbent members, inhibition caused by swelling, such as gel blocking, is likely to occur, making it impossible to make full use of the water-absorbent polymer's absorption performance.

Patent Literature 1 describes a body fluid absorbent member wherein: two sheets are fixed by a plurality of fixing parts, thereby forming, between adjacent fixing parts, channel spaces that are continuous along the longitudinal direction; and an absorbent component, wherein a body fluid absorbent material including a highly absorbent polymer is integrated with a contraction material, is arranged in each channel space. In the body fluid absorbent member disclosed in Patent Literature 1, the entire absorbent member can be employed effectively.

Patent Literature 2 describes an absorbent article including an absorbent member including: an excretion-section slit region in an excretion-section opposing zone, the excretion-section slit region having longitudinal slits extending along the longitudinal direction and being formed in a dispersed state; and a central slit region in a central area in the lateral direction and longitudinal direction of the excretion-section slit region. The absorbent article disclosed in Patent Literature 2 is improved in comfortableness while worn.

Patent Literature 3 describes an absorbent article including an absorbent member having four or more rows of slits provided with intervals therebetween. The absorbent article disclosed in Patent Literature 3 can reduce the rigidity of the absorbent member and improve absorption properties.

Applicant has previously proposed a disposable diaper including an absorbent assembly that includes an absorbent core in which a central absorbent member and a pair of side absorbent members are separated in the crotch region, wherein elastic members for causing the respective side absorbent members to stand up are provided along the longitudinal direction on the respective lateral sides of the absorbent core (Patent Literature 4).

Other than the aforementioned disposable diaper, Patent Literatures 3 and 5 disclose, as absorbent members for absorbent articles, absorbent members in which a plurality of slits with a predetermined length are formed.

CITATION LIST

Patent Literature

Patent Literature 1: JP 2002-224162 A
Patent Literature 2: JP 2015-42244 A
Patent Literature 3: JP S63-18122 U
Patent Literature 4: JP 2006-341061 A
Patent Literature 5: JP H01-87720 U

SUMMARY OF INVENTION

The invention relates to a sheet-like article for an absorbent article, the sheet-like article including a plurality of absorbent units, each absorbent unit including: a long base portion having a lateral direction, a longitudinal direction that is longer than the lateral direction, and a thickness direction; and water-absorbent polymer particles that are fixed to a surface of first side of the long base portion, the absorbent units being arranged such that the absorbent unit's longitudinal direction is oriented at least in one direction. When the water-absorbent polymer particles absorb a liquid, the water-absorbent polymer particles swell beyond the long base portion's lateral side edge portions that extend along the longitudinal direction, and a position, in the thickness direction, of each long base portion is varied from the position thereof before absorbing the liquid.

The invention also relates to a method for manufacturing a sheet-like article for an absorbent article, the sheet-like article including a plurality of absorbent units each including: a long base portion having a lateral direction, a longitudinal direction that is longer than the lateral direction, and a thickness direction; and water-absorbent polymer particles that are fixed to a surface of first side of the long base portion, the absorbent units being arranged such that the absorbent unit's longitudinal direction is oriented at least in one direction, wherein, when the water-absorbent polymer particles absorb a liquid, the water-absorbent polymer particles swell beyond the long base portion's lateral side edge portions that extend along the longitudinal direction, and a position, in the thickness direction, of each long base portion is varied from the position thereof before absorbing the liquid. The sheet-like article manufacturing method of the invention involves: a cutting step of cutting a continuous base sheet to thereby form a plurality of the long base portions; and a water-absorbent polymer particle dispersion step of dispersing the water-absorbent polymer particles on the surface of the first side of the plurality of long base portions that have been formed.

The invention also relates to an absorbent article including an absorbent assembly that includes a topsheet, a backsheet, and an absorbent member interposed between the topsheet and the backsheet, the absorbent article having an article longitudinal direction corresponding to a wearer's front-to-rear direction, and an article lateral direction orthogonal to the article longitudinal direction. The absorbent member includes an absorbent core formed of a sheet-like article including a plurality of absorbent units, each absorbent unit including: a long base portion having a lateral direction, a longitudinal direction that is longer than the lateral direction, and a thickness direction; and water-absorbent polymer particles that are fixed to a surface of first side of the long base portion, the absorbent units being arranged such that the absorbent unit's longitudinal direction is oriented at least in one direction. The absorbent core includes a central region in a central area in the article lateral direction, and a pair of side regions provided more outward, in the article lateral direction, than the central region. In each side region, the absorbent units are arranged such that the absorbent unit's longitudinal direction is oriented in the article lateral direction. The topsheet covers a skin-facing surface of the absorbent member, and includes extension portions extending outward, in the article lateral direction, from respective lateral side edge portions of the absorbent member, the extension portions being folded back toward a non-skin-facing surface side of the absorbent member and respectively covering the absorbent member's non-skin-facing surface located in the respective side regions of the absorbent core. A tip-end portion of each extension portion of the topsheet is located more toward the non-skin-facing surface side than the extension portion and is fixed to a constituent member of the absorbent article located adjacent to the extension portion.

DESCRIPTION OF EMBODIMENTS

Figure 1:
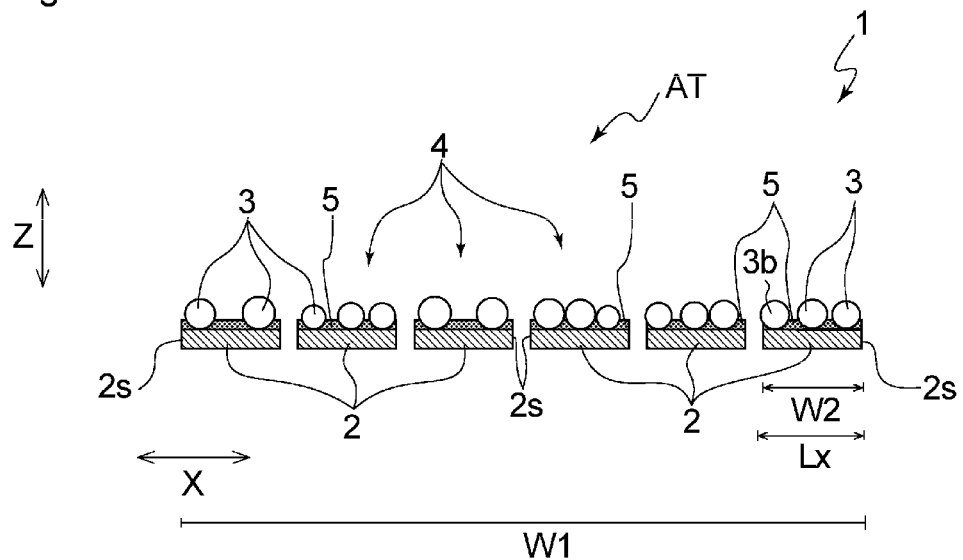
FIG. 1 is a cross-sectional view schematically illustrating an embodiment of a sheet-like article for an absorbent article of the invention, the figure illustrating a state before water-absorbent polymer particles absorb a liquid.

In the absorbent member disclosed in Patent Literature 1, the absorbent material including a highly absorbent polymer is arranged inside each channel space formed by fixing with the fixing parts, which makes it difficult for the absorbent material to move in the thickness direction, even when the highly absorbent polymer absorbs body fluid and swells. This makes it impossible to make full use of the absorption performance of the highly absorbent polymer.

Patent Literatures 2 and 3 describe nothing about the positional relationship between the water-absorbent polymer particles and the slits when the water-absorbent polymer particles absorb a liquid.

The present invention therefore provides a sheet-like article capable of overcoming the aforementioned drawbacks of the conventional art. The present invention also provides a method for manufacturing a sheet-like article capable of overcoming the aforementioned drawbacks of the conventional art.

In the disposable diaper disclosed in Patent Literature 4, the absorbent core is separated into a central absorbent member and a pair of side absorbent members, and elastic members for causing the respective side absorbent members to stand up are provided on the respective lateral sides of the absorbent core. Thus, the side absorbent members can stand up easily, thereby improving fittability and leakage-preventing performance in the crotch region. It is thought, however, that, while the diaper is worn, the standing side absorbent members may impinge upon the wearer's skin and cause uncomfortableness. Inventors' intent is to also eliminate any uncomfortableness caused by the standing side absorbent members.

Patent Literatures 3 and 5 only disclose absorbent members with slits, and describe nothing about causing the absorbent member in side sections on both lateral sides of the absorbent member to stand up.

The present invention therefore provides an absorbent article capable of overcoming the aforementioned drawbacks of the conventional art.

A sheet-like article of the invention is described below according to preferred embodiments thereof with reference to the drawings.

The sheet-like article of the invention is used for absorbent articles. In general, absorbent articles are used for absorbing and retaining excreted body fluid such as urine or menstrual blood. Absorbent articles include, for example, disposable diapers, sanitary napkins, and incontinence pads, but are not limited thereto, and widely encompass articles used for absorbing liquids excreted from the human body.

Typically, an absorbent article includes: a liquid-retentive absorbent member; a topsheet arranged on the skin-facing surface side of the absorbent member; and a backsheet arranged on the non-skin-facing surface side of the absorbent member. The absorbent member includes: the sheet-like article of the invention; and a liquid-permeable core-wrap sheet that covers the sheet-like article. Stated differently, the sheet-like article of the invention is used in an absorbent article, for example, as an absorbent member covered by a liquid-permeable core-wrap sheet. The absorbent article may include a so-called sublayer sheet on one or both of the skin-facing surface and non-skin-facing surface of the absorbent member. A sublayer sheet is a liquid-permeable sheet arranged between the absorbent member and the topsheet, or between the absorbent member and the backsheet.

For the topsheet, backsheet, and core-wrap sheet, various materials ordinarily used in this technical field can be used Without particular limitation. For example, for the topsheet, it is possible to use a liquid-permeable sheet, with examples including various hydrophilized nonwoven fabrics and porous films. For the backsheet, it is possible to use a liquid-impermeable or water-repellent sheet, with examples including thermoplastic resin films and laminates of such films and nonwoven fabrics. The backsheet may be vapor permeable. For the core-wrap sheet, it is possible to use, for example, tracing paper (tissue paper) made by a wet papermaking method or a liquid-permeable nonwoven fabric. The absorbent article may further include various components depending on the concrete usage of the absorbent article. Such components are known to persons skilled in the art. For example, in cases of using the absorbent article as a disposable diaper or a sanitary napkin, one or more pairs of leak-proof cuffs may be arranged on both left and right lateral sides on the topsheet.

Figure 2:
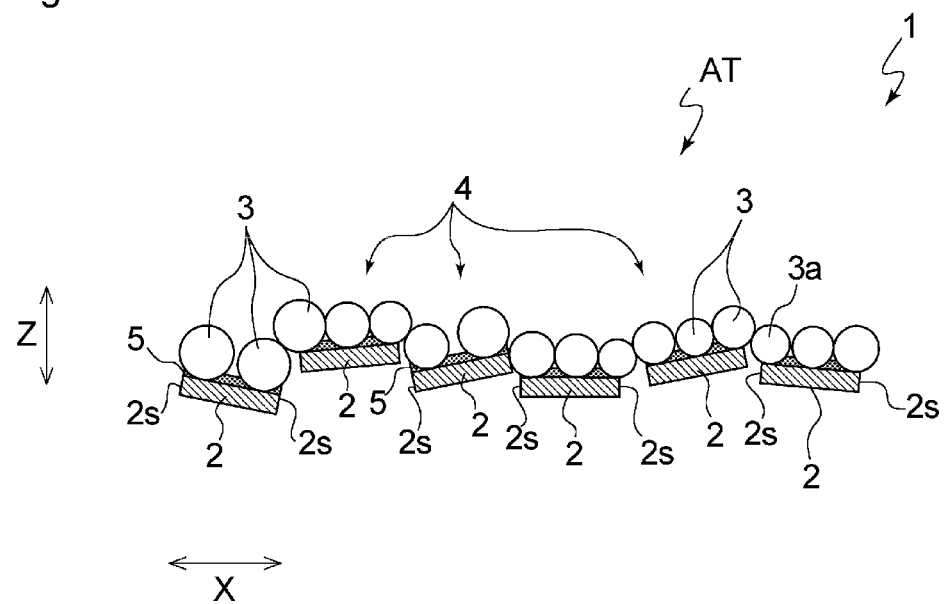
FIG. 2 is a cross-sectional view schematically illustrating a state in which the water-absorbent polymer particles in the sheet-like article illustrated in FIG. 1 have swollen by absorbing a liquid.
Figure 3:
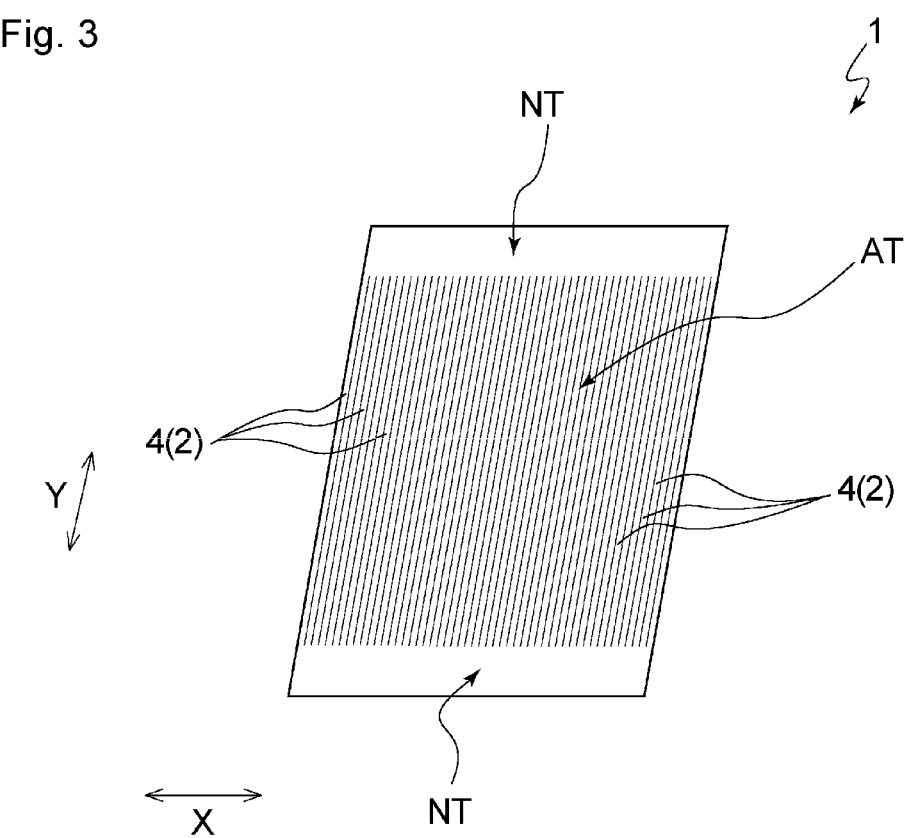
FIG. 3 is a perspective view as viewed from an upper surface side of the sheet-like article illustrated in FIG. 1.

FIGS. 1 and 2 are cross-sectional views schematically illustrating a sheet-like article 1 according to a preferred embodiment of the sheet-like article of the invention (also referred to hereinafter simply as "sheet-like article 1"). The sheet-like article 1 of FIG. 1 shows a state before water-absorbent polymer particles absorb a liquid (also referred to hereinafter simply as "a state before use"). The sheet-like article 1 of FIG. 2 shows a state in which the water-absorbent polymer particles have swollen by absorbing a liquid (also referred to hereinafter simply as "state after swelling"). Herein, a "state after swelling" refers to a state of the water-absorbent polymer particles after immersing the sheet-like article 1 in a physiological saline solution (0.9 mass % sodium chloride aqueous solution), whose temperature has been adjusted to 25° C., for 60 minutes. FIG. 3 shows a perspective view of the sheet-like article 1 in a state before use.

The sheet-like article 1 illustrated in FIG. 1 includes a plurality of absorbent units 4, each absorbent unit including: a long base portion 2 having a lateral direction (X direction), a longitudinal direction (Y direction) that is longer than the lateral direction (X direction), and a thickness direction (Z direction); and water-absorbent polymer particles 3 (also referred to hereinafter simply as "water-absorbent polymer 3") that are fixed to a surface of first side of the long base portion 2. The sheet-like article 1 is formed by arranging the absorbent units 4 such that the their longitudinal direction (Y direction) is oriented at least in one direction. The lateral direction (X direction), the longitudinal direction (Y direction), and the thickness direction (Z direction) of the long base portion 2 match the lateral direction (X direction), the longitudinal direction (Y direction), and the thickness direction (Z direction) of the absorbent unit 4, and, in the present embodiment, also match the lateral direction (X direction), the longitudinal direction (Y direction), and the thickness direction (Z direction) of the sheet-like article 1 (see FIG. 3). The longitudinal direction (Y direction) of the sheet-like article 1 also matches the wearer's front-to-rear direction when the absorbent article including the sheet-like article 1 is worn.

As illustrated in FIG. 1, the sheet-like article 1 is formed by arranging a plurality of absorbent units 4 such that the longitudinal direction (Y direction) of the absorbent units 4 is oriented in the longitudinal direction (Y direction) of the sheet-like article 1 (see FIG. 3). From the viewpoint of easy movement of the absorbent units 4, there is no intervening member present between the absorbent units 4, 4 adjacent to one another in the lateral direction (X direction) of the long base portions 2 (absorbent units 4). Stated differently, each absorbent unit 4 is in a state where it is not wrapped by any intervening member. In FIGS. 1 and 2, the upper surface, which is the first side of the long base portion 2, is the skin-facing surface facing the wearer's skin, and the lower surface, which is the second side of the long base portion 2, is the non-skin-facing surface facing the backsheet. Stated differently, the face on the opposite side from the first side is the second side.

In a state before use, the absorbent unit 4 of the sheet-like article 1 is formed in a continuous shape that is long in the longitudinal direction Y. As described further below, in a state before use, each absorbent unit 4 may include a water-absorbent polymer particle 3b that extends across the lateral side edge portion 2s of the long base portion 2 (see FIG. 1); thus, the length Lx in the lateral direction X is formed slightly longer than the later-described width (W2) of the long base portion 2. More specifically, the length Lx in the lateral direction X of the absorbent unit 4 is preferably approximately from 0.5 to 10 mm, more preferably approximately from 1 to 5 mm. The length Ly in the longitudinal direction Y of the absorbent unit 4 to the length Lx in the lateral direction X is preferably approximately from 20 to 200 times, more preferably approximately from 40 to 80 times. On condition that this scaling factor is satisfied, the length Ly in the longitudinal direction Y of the absorbent unit 4 is preferably approximately from 10 to 500 mm, more preferably approximately from 200 to 400 mm. As described above, the absorbent unit 4 has an extremely long, narrow shape.

In a state before use, the dimensional relationship between the long base portion 2's width W2 and the absorbent unit 4's length Lx in the lateral direction (X direction) is preferably 0 μm<(Lx−W2)<1400 μm, more preferably 200 μm<(Lx−W2)<1000 μm.

In the present embodiment, in a state before use, the sheet-like article 1 is formed in a rectangular shape that is long in the longitudinal direction (Y direction). The sheet-like article 1's length in the longitudinal direction (Y direction) is around 100 to 1000 mm, and the length in the lateral direction (X direction) is around 50 to 300 mm.

In a state before use, the sheet-like article 1 includes an absorbent region AT in which the plurality of absorbent units 4 are arranged so as to be oriented at least in one direction. From the viewpoint of facilitating the absorption of liquid in a region where the water-absorbent polymer particles 3 are fixed, in a planar view of the sheet-like article 1 in a state before use, the percentage of the absorbent region AT to the entire sheet-like article 1 is preferably 20% or greater, more preferably 50% or greater, and preferably 100% or less, more preferably 90% or less, and more specifically, preferably from 20 to 100%, more preferably from 50 to 90%. Herein, the expression "the percentage of the absorbent region AT is 100%" refers to a configuration wherein, in cases where for example the plurality of absorbent units 4 are arranged side by side in the lateral direction (X direction) of the sheet-like article 1 such that the longitudinal direction (Y direction) of the absorbent units 4 is oriented in the longitudinal direction (Y direction) of the sheet-like article 1, the absorbent units 4 are arranged over the entire region between both end portions, in the longitudinal direction (Y direction), of the sheet-like article 1. Alternatively, in cases where the plurality of absorbent units 4 are arranged side by side in the longitudinal direction (Y direction) of the sheet-like article 1 such that the longitudinal direction (Y direction) of the absorbent units 4 is oriented in the lateral direction (X direction) of the sheet-like article 1, the above expression refers to a configuration wherein the absorbent units 4 are arranged over the entire region between both the sheet-like article 1's lateral sides extending along the longitudinal direction (Y direction). Note that, in a planar view of the sheet-like article 1, regions other than the absorbent region AT constitute non-slit regions NT described further below.

In cases where the longitudinal direction (Y direction) of the absorbent units 4 is arranged so as to be oriented in the longitudinal direction (Y direction) of the sheet-like article 1, it is preferable that 3 pieces or more, more preferably 50 pieces or more, and preferably 1000 pieces or fewer, more preferably 500 pieces or fewer, and more specifically, preferably from 3 to 1000 pieces, more preferably from 50 to 500 pieces, of the absorbent units 4 are arranged in a single sheet-like article. In cases where the longitudinal direction (Y direction) of the absorbent units 4 is arranged so as to be oriented in the lateral direction (X direction) of the sheet-like article 1, it is preferable that 3 pieces or more, more preferably 50 pieces or more, and preferably 3500 pieces or fewer, more preferably 2000 pieces or fewer, and more specifically, preferably from 3 to 3500 pieces, more preferably from 50 to 2000 pieces, of the absorbent units 4 are arranged in a single sheet-like article. In counting the number of absorbent units 4, the number of absorbent units is defined as the maximum number of absorbent units that intersect with a straight line rendered in the lateral direction X.

From the viewpoint of ease of transportation during manufacture, it is preferable that the sheet-like article 1 in a state before use is configured such that a plurality of absorbent units 4 are arranged such that their longitudinal direction (Y direction) is oriented in the longitudinal direction (Y direction) of the sheet-like article 1, and it is more preferable that the absorbent units 4 are arranged in the longitudinal direction (Y direction) of the sheet-like article 1 parallel to the longitudinal direction (Y direction) such that the absorbent units 4 do not intersect with one another. The sheet-like article 1 illustrated in FIG. 1 is formed by using a plurality of absorbent units 4 respectively including long base portions 2 with a uniform width, and by arranging the absorbent units 4 parallel to the longitudinal direction (Y direction) of the sheet-like article 1 such that the longitudinal direction (Y direction) of the absorbent units 4 is oriented in the longitudinal direction (Y direction) of the sheet-like article 1.

It is preferable that the sheet-like article 1 includes, in both end portions in the longitudinal direction (Y direction) or in both lateral sides extending along the longitudinal direction (Y direction), non-slit regions NT wherein a plurality of long base portions 2 are connected in the lateral direction (X direction), and as illustrated in FIG. 3, the sheet-like article 1 of the present embodiment includes non-slit regions NT in both end portions in the longitudinal direction (Y direction). Stated differently, the sheet-like article 1 of the present embodiment includes a single base sheet; the non-slit regions NT are provided in the respective end portions, in the longitudinal direction (Y direction), of the base sheet; and the long base portions formed by a later-described cutting step are provided between the non-slit regions NT. Providing these non-slit regions NT is advantageous in that, in a state before use, the sheet form of the sheet-like article 1 is easy to maintain and the structure is less prone to getting disarranged, and the sheet is easy to transport during manufacture. Preferably, no water-absorbent polymer particle 3 is arranged in the non-slit regions NT. By not arranging any water-absorbent polymer particles 3 in the non-slit regions NT, even when liquid is absorbed, the water-absorbent polymer particles 3 are less likely to swell in the non-slit regions NT, and thus, even in a state after swelling, the sheet form of the sheet-like article 1 is easy to maintain and the structure is less prone to getting disarranged. Meanwhile, in regions where the water-absorbent polymer particles 3 are arranged, liquid can be absorbed easily, thus being effective in easily striking a balance over the entire sheet-like article 1. Further, in cases where the sheet-like article 1 having the non-slit regions NT provided in the respective end portions in the longitudinal direction (Y direction)—as illustrated in FIG. 3—is used in an absorbent article, it is preferable that both end portions, in the longitudinal direction (Y direction), of the sheet-like article 1 are fixed to the absorbent article, from the viewpoint that the sheet form of the sheet-like article 1 becomes easy to maintain and the structure becomes less prone to getting disarranged, and also the softness of the absorbent region AT is improved, making it less likely to cause uncomfortableness to the wearer.

In the sheet-like article 1 illustrated in FIG. 1, from various viewpoints such as swelling inhibition, softness, air permeability, sheet-form maintainability, and the amount of water-absorbent polymer borne, the ratio (W2/W1) of the width (W2) (length in the lateral direction (X direction)) of the long base portion 2 to the width (W1) of the sheet-like article 1 is preferably 0.001 or greater, more preferably 0.002 or greater, and preferably 0.2 or less, more preferably 0.04 or less, and more specifically, preferably from 0.001 to 0.2, more preferably from 0.002 to 0.04.

Preferably, from the same viewpoint, the width W2 of the long base portion 2 is preferably 0.3 mm or greater, more preferably 0.6 mm or greater, and preferably 10 mm or less, more preferably 2 mm or less, even more preferably 1.8 mm or less, and more specifically, preferably from 0.3 to 10 mm, more preferably from 0.6 to 2 mm, even more preferably from 0.6 to 1.8 mm.

The long base portions 2 (base sheet) constituting the absorbent units 4 are preferably made of a hydrophilic sheet from the viewpoint of easy diffusibility of liquid in the absorbent region AT and improvement in usage efficiency of the water-absorbent polymer 3. Examples of hydrophilic sheets include paper, nonwoven fabrics, cloths, and synthetic sponge made by foaming synthetic resins, and among the above, nonwoven fabrics are preferably used, from the viewpoint of relatively high tensile strength despite its thinness and capability of achieving softness and thinness. Examples of preferably usable nonwoven fabrics include hydrophilic nonwoven fabrics including hydrophilic fibers as constituent fibers, and hydrophilic nonwoven fabrics including, as constituent fibers, fibers obtained by imparting hydrophilicity to synthetic fibers. The basis weight of the nonwoven fabric is preferably from 5 to 100 g/m$^2$, more preferably from 10 to 40 g/m$^2$.

Various types of polymers conventionally used in the technical field of absorbent articles can be used for the water-absorbent polymer 3 to be fixed to the surface of the first side of the long base portions 2. Examples include sodium polyacrylate, (acrylic acid-vinyl alcohol) copolymer, crosslinked sodium polyacrylate, (starch-acrylic acid) graft polymer, (isobutylene-maleic anhydride) copolymer and saponified products thereof, potassium polyacrylate, and cesium polyacrylate. One type of polymer may be used singly, or two or more types may be used as a mixture. Based on differences in their shape, there are various types of water-absorbent polymer particles 3, such as the amorphous type, block type, barrel type, pellet-agglomeration type, and spherical type; any type of particle may be used. In the sheet-like article 1, spherical-type particles are used.

Examples of methods for fixing the water-absorbent polymer particles 3 to the long base portions 2 include methods using adhesives and chemical fixing methods employing a hydrogen bond etc., and in cases where the long base portions 2 are a nonwoven fabric or a cloth, the constituent fibers may be napped, and the water-absorbent polymer particles 3 may be fixed among the napped constituent fibers. In the sheet-like article 1 illustrated in FIGS. 1 and 2, an adhesive 5 is employed. More specifically, the water-absorbent polymer particles 3 of the sheet-like article 1 are fixed to the surface of the long base portions 2 by means of the adhesive 5. Fixing the water-absorbent polymer particles 3 to the surface of the long base portions 2 by means of the adhesive 5 suppresses the water-absorbent polymer particles 3 from falling off in a state before use of the sheet-like article 1 and in a state after the polymer has swollen.

For example, a hot-melt adhesive may be preferably used for the adhesive 5. Examples of hot-melt adhesives include styrene-based and olefin-based adhesives. Examples of styrene-based hot-melt adhesives that may be used include styrene-butadiene-styrene (SBS) copolymers, styrene-isoprene-styrene (SIS) copolymers, styrene-ethylene-butylene-styrene (SEBS) copolymers which are hydrogenated products of SBS, and blended hot-melt adhesives in which two or more types of the above are blended. Among the above, particularly, a blended hot-melt adhesive including SIS and SBS or a blended hot-melt adhesive including SIS and SEBS is preferably used from the viewpoint of the ease of balancing tack force and cohesive force. The amount of hot-melt adhesive applied is preferably from 0.5 to 100 g/m$^2$, more preferably from 5 to 50 g/m$^2$.

In the sheet-like article 1 illustrated in FIG. 1, from the viewpoint of easily maintaining the sheet form of the sheet-like article 1 before use, making it less likely for the structure to get disarranged, and arranging the water-absorbent polymer particles 3 in appropriate positions, it is preferable that, in a state before use, i.e., before the water-absorbent polymer particles 3 absorb a liquid, the long base portions 2, 2 of respective absorbent units 4 which are adjacent to one another in the lateral direction (X direction) are at least partially contiguous, and more preferably, the long base portions 2, 2 which are adjacent to one another in the lateral direction (X direction) are contiguous over their entirety. In the sheet-like article 1 illustrated in FIG. 1, the long base portions 2, 2 which are adjacent to one another in the lateral direction (X direction) are contiguous over their entirety. Herein, "contiguous" means that adjacent long base portions 2, 2 abut one another and are continuous.

In the sheet-like article 1, in a state after swelling as illustrated in FIG. 2, the water-absorbent polymer particles 3 swell beyond the long base portion 2's lateral side edge portions 2s that extend along the longitudinal direction (Y direction). Herein, "the water-absorbent polymer particles 3 swell beyond the long base portion 2's lateral side edge portions 2s" means, in other words, that, in a state after swelling of the sheet-like article 1, the swollen water-absorbent polymer particles 3 extend across the lateral side edge portions 2s of the long base portions 2, like the swollen water-absorbent polymer particle 3a as illustrated in FIG. 2, for example. Note that, so long as the swollen water-absorbent polymer particles 3 extend across the lateral side edge portions 2s of the long base portions 2 in a state after swelling of the sheet-like article 1, the water-absorbent polymer particles 3 may exist inward of the lateral side edge portions 2s of the long base portions 2 in a state before use of the sheet-like article 1. Alternatively, the water-absorbent polymer particles 3 may extend across the lateral side edge portions 2s of the long base portions 2 from the beginning, like the water-absorbent polymer particle 3b before use (before swelling) as illustrated in FIG. 1, for example.

Further, in the sheet-like article 1, in a swollen state as illustrated in FIG. 2, the position, in the thickness direction (Z direction), of each long base portion 2 is varied from the position thereof before absorbing a liquid. Herein, "in a state after swelling of the sheet-like article 1, the position, in the thickness direction (Z direction), of each long base portion 2 is varied from the position thereof before absorbing a liquid" means that the sheet-like article is formed such that the position of each long base portion 2 in a state after swelling of the water-absorbent polymer particles 3 as illustrated in FIG. 2 is varied, in the vertical direction, from the position of the long base portion 2 in a state before use (before swelling) of the water-absorbent polymer particles 3 as illustrated in FIG. 1. More specifically, the varying in position includes cases where long base portions are misaligned vertically, obliquely, or both.

As described above, in the sheet-like article 1 of the present embodiment, as illustrated in FIG. 2, in a state after swelling, the water-absorbent polymer particles 3 swell beyond the long base portion 2's lateral side edge portions 2s (cf. the water-absorbent polymer 3a in FIG. 2), and the position, in the thickness direction (Z direction), of each long base portion 2 is varied from the position thereof before absorbing a liquid. Thus, in cases where the sheet-like article 1 is used in an absorbent article, even when the water-absorbent polymer particles 3, 3 that have swollen beyond the lateral side edge portions 2s of the respective long base portions 2 of adjacent absorbent units 4, 4 come into contact with one another when the water-absorbent polymer particles 3 absorb body fluid and swell as illustrated in FIG. 2, the adjacent absorbent units 4, 4 are facilitated to move freely in the thickness direction (Z direction), which makes it possible to lessen collision between the swollen water-absorbent polymer particles 3, 3 and reduce pressure applied to the swollen water-absorbent polymer particles 3, thus suppressing inhibition of absorption of body fluid by the water-absorbent polymer particles 3. Thus, in the sheet-like article 1 of the present embodiment, the water-absorbent polymer particles 3 are less likely to cause swelling inhibition when the water-absorbent polymer particles 3 absorb body fluid and swell, and it is possible to make full use of the absorption performance of the water-absorbent polymer particles 3. Thus, the absorption performance is easily improved. Particularly, in the sheet-like article 1 of the present embodiment, since there is no intervening member present between the absorbent units 4, 4 adjacent to one another, the absorbent units 4 can move easily, thus making it even more easy to achieve the aforementioned effects.

Further, in the sheet-like article 1, in a state after swelling as illustrated in FIG. 2, the respective positions of the long base portions 2 constituting adjacent absorbent units 4 are varied in the thickness direction (Z direction) so as to be misaligned vertically or obliquely, for example. Thus, the adjacent absorbent units 4, 4 are facilitated to move freely in the thickness direction (Z direction), which makes it possible to easily lessen collision between the swollen water-absorbent polymer particles 3, 3 and reduce pressure applied to the swollen water-absorbent polymer particles 3, thus suppressing inhibition of absorption of body fluid by the water-absorbent polymer particles 3.

In the sheet-like article 1, from the viewpoint of further suppressing swelling inhibition of the water-absorbent polymer particles 3 by causing the water-absorbent polymer particles 3 in a swollen state to swell beyond the lateral side edge portions 2s of the long base portions 2 and cause adjacent absorbent units 4, 4 to move freely in the thickness direction (Z direction), it is preferable that, in a state before use as illustrated in FIG. 1, the water-absorbent polymer particles 3 are arranged in the vicinity of the long base portion 2's lateral side edge portions 2s which extend along the longitudinal direction (Y direction), and more preferably, the water-absorbent polymer particles 3 protrude beyond the long base portion 2's lateral side edge portions 2s (cf. the water-absorbent polymer particle 3b illustrated in FIG. 1).

Further, in the sheet-like article 1, from the viewpoint of further suppressing swelling inhibition of the water-absorbent polymer particles 3 by causing the water-absorbent polymer particles 3 in a swollen state to swell beyond the lateral side edge portions 2s of the long base portions 2 and cause adjacent absorbent units 4, 4 to move freely in the thickness direction (Z direction), it is preferable that the distance between the long base portion 2's both lateral side edge portions 2s, 2s that extend along the longitudinal direction (Y direction) is greater than the average particle size of the water-absorbent polymer particles 3 in a state before use (before swelling), and is smaller than the average particle size of the water-absorbent polymer particles 3 in a state after swelling. Herein, "the distance between the long base portion 2's both lateral side edge portions 2s, 2s" is synonymous with the width (W2) of the long base portion 2. It is preferable that the average particle size of the water-absorbent polymer particles 3 in a state before use (before swelling) is preferably 20 μm or greater, more preferably 200 μm or greater, and preferably 700 μm or less, more preferably 500 μm or less, and more specifically, preferably from 20 to 700 μm, more preferably from 200 to 500 μm. On the other hand, the average particle size of the water-absorbent polymer particles 3 in a state after swelling is preferably 200 μm or greater, more preferably 800 μm or greater, and preferably 3000 μm or less, more preferably 2000 μm or less, and more specifically, preferably from 200 to 3000 μm, more preferably from 800 to 2000 μm. The average particle size of the water-absorbent polymer particles 3 is found according to the following measurement method.

{Method for Measuring Average Particle Size of Water-Absorbent Polymer Particles in a State Before Use}

The average particle size in a state before use can be measured using water-absorbent polymer particles before use by observing the diameter or major axis of the water-absorbent polymer particles with an optical microscope. Herein, "diameter" applies to cases where the water-absorbent polymer particle is spherical, and "major axis" applies to cases where the water-absorbent polymer particle is odd-formed, such as rhombic, rectangular, cluster-like, or football-shaped. The diameter or major axis is measured for a total of 50 water-absorbent polymer particles, and the number-average particle size is defined as the average particle size of the water-absorbent polymer particles in a state before use.

{Method for Measuring Average Particle Size of Water-Absorbent Polymer Particles in a State after Swelling}

The average particle size in a state after swelling can be measured by: immersing the sheet-like article 1 in a physiological saline solution (0.9 mass % sodium chloride aqueous solution) whose temperature has been adjusted to 25° C.; taking the sheet-like article 1 out from the physiological saline solution after 1 hour from the start of immersion; draining the sheet-like article by hanging the same in a vertical state for 30 minutes; and then observing, with an optical microscope, the diameter or major axis of the water-absorbent polymer particles on the surface of the long base portions 2. Herein, "diameter" applies to cases where the water-absorbent polymer particle is spherical, and "major axis" applies to cases where the water-absorbent polymer particle is odd-formed, such as rhombic, rectangular, cluster-like, or football-shaped. The diameter or major axis is measured for a total of 50 water-absorbent polymer particles, and the number-average particle size is defined as the average particle size of the water-absorbent polymer particles in a state after swelling.

Figure 4:
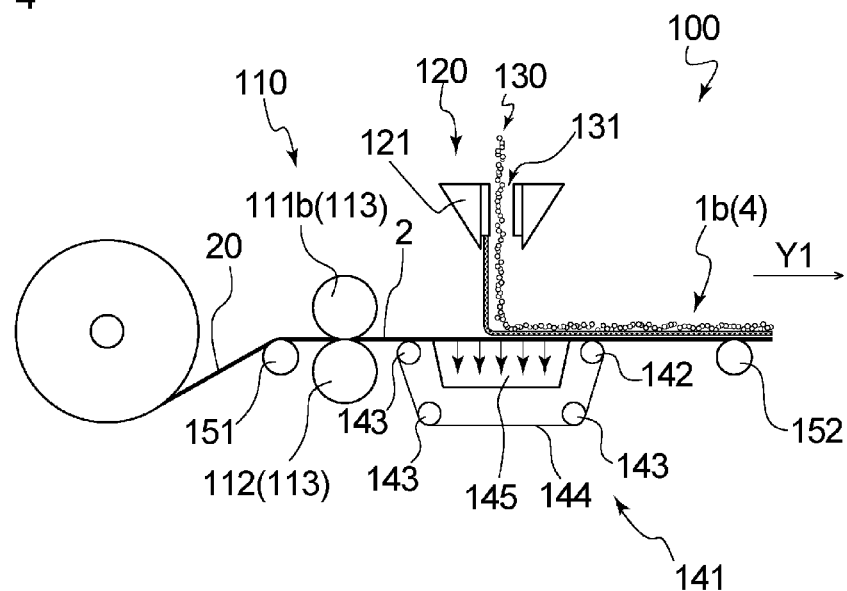
FIG. 4 is a schematic diagram illustrating an embodiment of a device for manufacturing the sheet-like article illustrated in FIG. 1.

Next, a preferred embodiment of a method for manufacturing a sheet-like article of the invention is described with reference to FIG. 4 according to an example of manufacturing the sheet-like article 1 configured as above. FIG. 4 illustrates a manufacturing device 100 suitably used for the manufacturing method of the present embodiment. The manufacturing device 100 of the present embodiment includes, in the following order from the upstream side toward the downstream side of the manufacturing steps: a base sheet cutting unit 110; an adhesive application unit 120; and a water-absorbent polymer dispersion unit 130. Note that, although the manufacturing device 100 illustrated in FIG. 4 uses a device in which the adhesive application unit 120 and the water-absorbent polymer dispersion unit 130 are integrated, the adhesive application unit 120 and the water-absorbent polymer dispersion unit 130 do not have to be integrated. In the integrated device, the adhesive application unit 120 is arranged on the upstream side of the device, and the water-absorbent polymer dispersion unit 130 is arranged on the downstream side of the integrated device.

Figure 5:
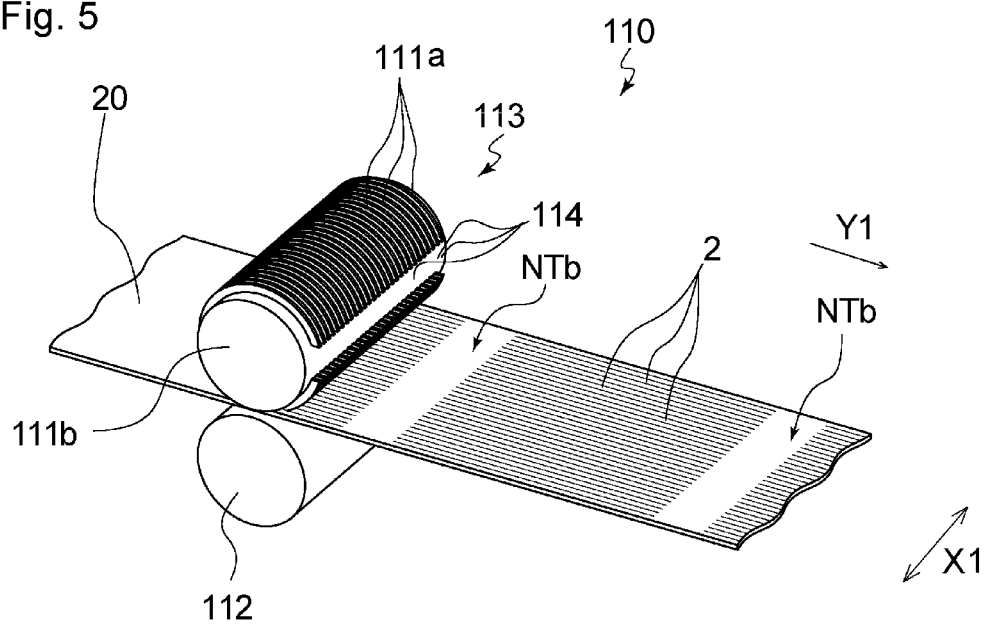
FIG. 5 is a schematic perspective view of a base sheet cutting unit provided in the manufacturing device illustrated in FIG. 4.

The base sheet cutting unit 110 is a region for cutting a continuous base sheet 20 to form a plurality of long base portions 2. Any one of various known cutting devices can be used without particular limitation for cutting the base sheet 20. As illustrated in FIG. 5, this manufacturing device 100 employs a cutting device 113 including: a rotary die 111b having a plurality of cutter blades 111a, 111a, 111a, . . . arranged on the circumferential surface thereof; and a receiving roller 112 that has a flat circumferential surface and that is arranged in opposition to the rotary die 111b. Each cutter blade 111a of the cutting device 113 is arranged along the rotating direction of the rotary die 111b, and the plurality of cutter blades 111a, 111a, 111a, . . . are arranged side by side in a direction (X1 direction) orthogonal to the transporting direction (Y1 direction) of the continuous base sheet 20. The distance between cutter blades 111a, 111a adjacent to one another in the orthogonal direction (X1 direction) corresponds to the width (i.e., the length in the lateral direction (X direction)) of each long base portion 2 to be formed. Herein, the transporting direction (Y1 direction) of the base sheet 20 corresponds to the longitudinal direction (Y direction) of the sheet-like article 1 to be manufactured, and the orthogonal direction (X1 direction) corresponds to the lateral direction (X direction) of the sheet-like article 1 to be manufactured. Note that, for cutting the base sheet 20, it is possible to use: a cutting device employing a shear-cut method in which cutting is achieved by rubbing the side surfaces of an upper blade and a lower blade against one another; a device in which a plurality of score cut knives are arranged side by side in the orthogonal direction (X1 direction); or a laser device that performs melting-and-cutting by the irradiation of a laser beam.

As in the sheet-like article 1 illustrated in FIG. 3, in cases where the sheet-like article 1 includes respective non-slit regions NT at both end portions in the longitudinal direction (Y direction), a depression 114 may be formed in the circumferential surface of each cutter blade 111a, as illustrated in FIG. 5 for example. The length of the arc in the section of the depression 114 in the outer circumference of each rotating cutter blade 111a corresponds to a length equal to the total length, in the longitudinal direction (Y direction), of the non-slit regions NT arranged at both end portions of the sheet-like article 1 as illustrated in FIG. 3. It is possible to prepare a plurality of cutter blades 111a, 111a, 111a, . . . each having such a depression 114, and to use the rotary die 111b in which the respective depressions 114, 114 of the cutter blades 111a adjacent to one another in the X1 direction are aligned. Note that the length of the arc in a section excluding the depression 114 in the outer circumference of each rotating cutter blade 111a corresponds to the length, in the longitudinal direction (Y direction), of each long base portion 2 of the sheet-like article 1 illustrated in FIG. 3. Further, in cases where the sheet-like article 1 includes non-slit regions NT in both lateral sides extending along the longitudinal direction (Y direction), the cutter blades 111a do not have to be provided in positions corresponding to the respective non-slit regions NT.

The adhesive application unit 120, which is located downstream of the base sheet cutting unit 110, is a region for applying an adhesive 5 on the surface of first side (upper surface) of the respective long base portions 2. As illustrated in FIG. 4, the manufacturing device 100 includes an application head 121. Any one of various known application devices can be used without particular limitation for the application head 121. In the X1 direction, the application head 121 is formed having a length corresponding to the width (length in the lateral direction (X direction)) of the absorbent region AT of the sheet-like article 1. The application head 121 configured as above is arranged above first side (upper surface) of the long base portions 2.

The water-absorbent polymer dispersion unit 130, which is located downstream of the adhesive application unit 120, is a region for dispersing water-absorbent polymer particles 3 on the surface of the first side (upper surface) of the long base portions 2, to thereby form absorbent units 4. As illustrated in FIG. 4, the manufacturing device 100 includes a water-absorbent polymer introduction unit 131. For the water-absorbent polymer introduction unit 131, any one of various known introduction devices can be used without particular limitation. In the X1 direction, the water-absorbent polymer introduction unit 131 is formed having a length corresponding to the width (length in the lateral direction (X direction)) of the absorbent region AT of the sheet-like article 1. The water-absorbent polymer introduction unit 131 configured as above is arranged above the first side (upper surface) of the long base portions 2.

In the manufacturing device 100 illustrated in FIG. 4, a vacuum conveyor 141 is arranged at a position opposing the device in which the adhesive application unit 120 and the water-absorbent polymer dispersion unit 130 are integrated, and on the lower surface side of the plurality of long base portions 2 being transported. The vacuum conveyor 141 includes an endless air-permeable belt 144 that bridges a drive roller 142 and a plurality of driven rollers 143; and a vacuum box 145 arranged at a position opposing the aforementioned integrated device across the air-permeable belt 144. The plurality of long base portions 2, which have been formed by cutting the base sheet 20 with the base sheet cutting unit 110, are introduced onto the vacuum conveyor 141.

The manufacturing device 100 illustrated in FIG. 4 includes: a drive roller 151 that pays out the base sheet 20 from an original textile roll of the continuous base sheet 20; and a drive roller 152, at the most downstream side, that transports a precursor 1b of a sheet-like article 1 which has been manufactured.

Next, a method for manufacturing sheet-like articles 1 continuously using the aforementioned manufacturing device 100 of the present embodiment, i.e., an embodiment of the method for manufacturing sheet-like articles of the invention, will be described.

The method for manufacturing a sheet-like article 1 of the present embodiment involves: a cutting step of cutting a continuous base sheet 20 to thereby form a plurality of the long base portions 2; and a water-absorbent polymer particle dispersion step of dispersing water-absorbent polymer particles 3 on the surface of first side of the plurality of long base portions that have been formed. In the present embodiment, an adhesive application step of applying an adhesive 5 is provided before the water-absorbent polymer particle dispersion step. More specifically, the method for manufacturing a sheet-like article 1 of the present embodiment includes the adhesive application step after the cutting step, and the water-absorbent polymer particle dispersion step after the adhesive application step.

First, before executing the cutting step, negative pressure is generated inside the vacuum box 145 by activating an evacuation device connected thereto.

Next, the drive rollers 151 and 152 are driven, the cutting device 113 and the air-permeable belt 144 are rotated, and the vacuum conveyor 141 is activated. Then, the base sheet 20 is paid out by the drive roller 151 from the original textile roll of the continuous base sheet 20, and the base sheet 20 is supplied between the receiving roller 112 and the plurality of cutter blades 111a in the cutting device 113 of the base sheet cutting unit 110, to cut the continuous base sheet 20 and form a plurality of long base portions 2 (cutting step). In the present embodiment, as illustrated in FIG. 5, the plurality of cutter blades 111a, which are each arranged along the rotating direction of the rotary die 111b, are arranged side by side in the direction (X1 direction) orthogonal to the transporting direction (Y1 direction) of the continuous base sheet 20, and thus form the plurality of long base portions 2 by cutting the continuous base sheet 20 along the transporting direction (Y1 direction) of the base sheet 20 and at a plurality of sections in the orthogonal direction (X1 direction). The sections cut by the cutter blades 111a become the lateral side edge portions 2s of the respective long base portions 2.

In the present embodiment, each of the cutter blades 111a has a depression 114. Thus, a non-cut portion NTb corresponding to twice the length, in the longitudinal direction (Y direction), of the non-slit region NT is formed in the continuous base sheet 20 being transported, the non-cut portion NTb being formed intermittently at an interval corresponding to the length, in the longitudinal direction (Y direction), of the long base portion 2. The plurality of long base portions 2 formed in the cutting step are formed parallel to one another along the transporting direction (Y1 direction) and are arranged side by side in the orthogonal direction (X1 direction).

Next, an adhesive 5 is applied on the surface of first side (upper surface) of the long base portions 2 that have been formed in the cutting step (adhesive application step). In the present embodiment, while the long base portions 2 that have been formed in the cutting step are being transported by the vacuum conveyor 141 and are located above the vacuum box 145, the application head 121 of the adhesive application unit 120 applies the adhesive 5 intermittently on the surface of the first side (upper surface) of the long base portions 2 formed side by side in the orthogonal direction (X1 direction), except in non-cut portions NTb.

Next, water-absorbent polymer particles 3 are dispersed on the adhesive 5 applied on the surface of the first side (upper surface) of the long base portions 2 in the adhesive application step (water-absorbent polymer particle dispersion step). In the present embodiment, while the long base portions 2, which have the adhesive 5 applied on the surface of the first side (upper surface) in the adhesive application step, are being transported by the vacuum conveyor 141 and are located above the vacuum box 145, the water-absorbent polymer introduction unit 131 of the water-absorbent polymer dispersion unit 130 disperses the water-absorbent polymer particles 3 on the adhesive 5 applied on the surface of the first side (upper surface) of the long base portions 2 arranged side by side in the orthogonal direction (X1 direction), except in the non-cut portions NTb. By dispersing the water-absorbent polymer particles 3 as described above, a plurality of absorbent units 4 are formed, wherein the water-absorbent polymer particles 3 are fixed to the surface of the first side (upper surface) of the respective long base portions 2 by means of the adhesive 5. The absorbent units 4 formed as above are arranged such that their longitudinal direction (Y direction) is oriented in the transporting direction (Y1 direction), to thereby form a precursor 1b of a sheet-like article 1.

Then, the precursor 1b of the sheet-like article 1 is transported downstream by the drive roller 152, and, using a known cutting device (not illustrated), the precursor 1b is cut at every position located at half the length, in the transporting direction (Y1 direction), of the non-cut portion NTb. In this way, sheet-like articles 1, each including respective non-slit regions NT at both end portions in the longitudinal direction (Y direction), are manufactured continuously. With the manufacturing device 100 of the present embodiment and the manufacturing method of the present embodiment using this device, it is possible to manufacture sheet-like articles 1 stably and efficiently.

Further, according to the manufacturing method of the present embodiment, first, the long base portions 2 with a uniform width are formed by using the plurality of cutter blades 111a, 111a, 111a, . . . , and then, the adhesive 5 is applied on the surface of first side (upper surface) of the respective long base portions 2. Thus, the manufactured sheet-like article 1 is likely to be configured such that the long base portions 2, 2 of absorbent units which are adjacent to one another in the lateral direction (X direction) are contiguous over their entirety. Such sheet-like articles 1 can be manufactured stably and efficiently.

Next, other embodiments of the sheet-like article of the invention will be described. The description given for the foregoing embodiment applies as appropriate to features that are not particularly explained in relation to the other embodiments. In the sheet-like articles 1 illustrated in FIGS. 6, 7, and 9 to 11, members that are the same as those in the sheet-like article 1 illustrated in FIGS. 1 and 3 are accompanied by the same reference numbers.

Figure 6:
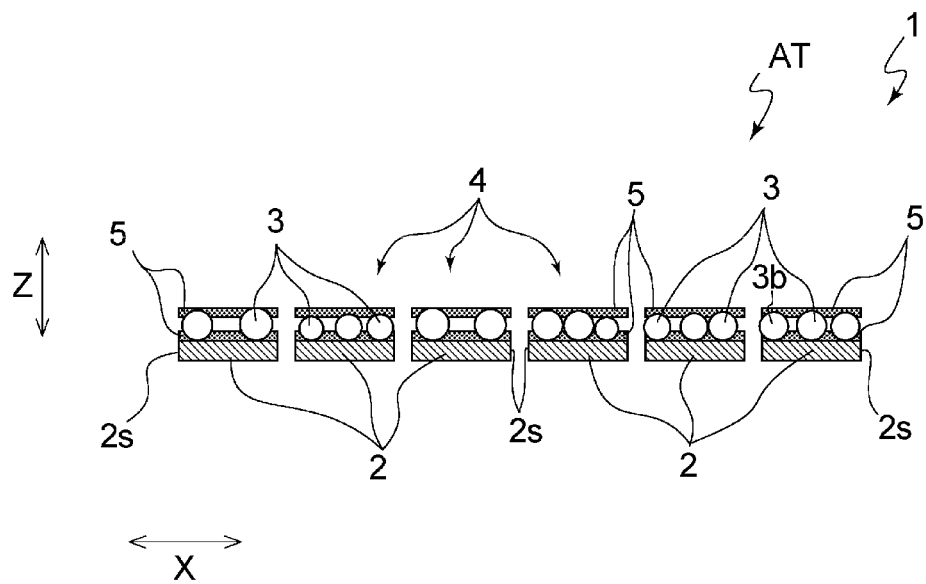
FIG. 6 is a cross-sectional view schematically illustrating another embodiment of a sheet-like article of the invention, the figure illustrating a state before water-absorbent polymer particles absorb a liquid (corresponding to FIG. 1).

The sheet-like article 1 illustrated in FIG. 6 is in a state before use, and is configured such that: water-absorbent polymer particles 3 are fixed on a surface of first side (upper surface) of long base portions 2 by an adhesive 5; and an adhesive 5 is further arranged on the water-absorbent polymer particles 3.

The sheet-like article 1 illustrated in FIG. 6 can be manufactured, for example, by providing, in the manufacturing device 100 illustrated in FIG. 4, another separate adhesive application unit 120 downstream of the water-absorbent polymer dispersion unit 130, and applying, after dispersing the water-absorbent polymer particles 3, an adhesive 5 on the water-absorbent polymer particles 3 with the separate adhesive application unit 120.

The sheet-like article 1 illustrated in FIG. 6 can achieve the effect that the water-absorbent polymer particles 3 are prevented from scattering and falling off during transportation and stable absorption performance is achieved.

Figure 7:
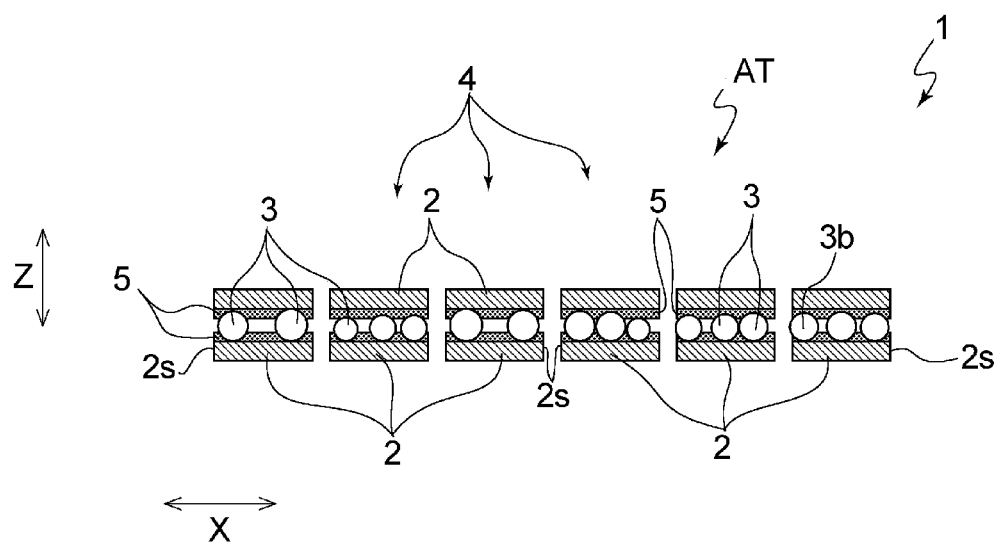
FIG. 7 is a cross-sectional view schematically illustrating another embodiment of a sheet-like article of the invention, the figure illustrating a state before water-absorbent polymer particles absorb a liquid (corresponding to FIG. 1).

The sheet-like article 1 illustrated in FIG. 7 is in a state before use, and is configured such that: water-absorbent polymer particles 3 are fixed on a surface of first side (upper surface) of long base portions 2 by an adhesive 5; an adhesive 5 is further arranged on the water-absorbent polymer particles 3; and second long base portions 2 are further arranged on the adhesive 5. Stated differently, the sheet-like article 1 illustrated in FIG. 7 is configured such that the water-absorbent polymer particles 3 are fixed by sandwiching the water-absorbent polymer particles 3 by the long base portions 2 on which the adhesive 5 has been applied on the surface of first side thereof.

The sheet-like article 1 illustrated in FIG. 7 can be manufactured as follows. For example, by using the manufacturing device 100 illustrated in FIG. 4, a plurality of long base portions 2 are formed by cutting a continuous base sheet 20, and then, an adhesive 5 is applied on the surface of first side (upper surface) of all of the long base portions 2 that have been formed. Then, the water-absorbent polymer particles 3 are dispersed only on the adhesive 5 applied on the surface of the first side (upper surface) of a plurality of the long base portions 2 that are located, for example, on the right side of a bisecting position in the orthogonal/cross direction (X1 direction), for example. Then, a plurality of the long base portions 2 that are located on the left side of the bisecting position in the orthogonal/cross direction (X1 direction) and that have the adhesive 5 applied on the surface of the first side (upper surface) are folded onto the water-absorbent polymer particles 3 on the aforementioned right side by using a known fold-back plate.

Figure 8:
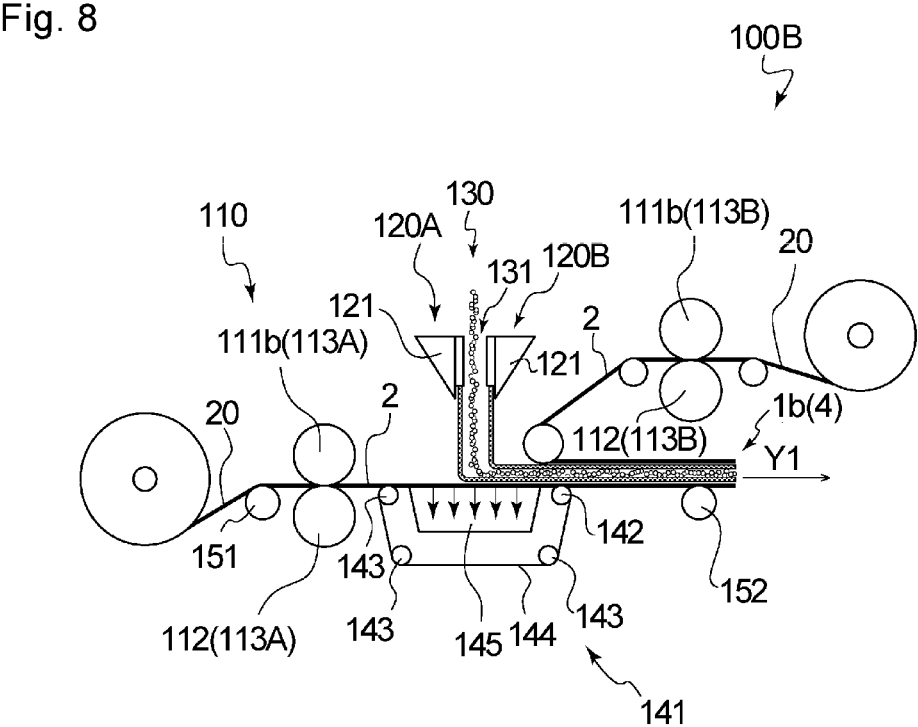
FIG. 8 is a schematic diagram illustrating an embodiment of a device for manufacturing the sheet-like article illustrated in FIG. 7.

Alternatively, the sheet-like article 1 illustrated in FIG. 7 can be manufactured using, for example, a manufacturing device 100E illustrated in FIG. 8. The manufacturing device 100B includes: a first slitting device 113A that cuts a continuous base sheet 20 for forming a plurality of long base portions 2 on the lower surface side of the sheet-like article 1 illustrated in FIG. 7; and, in addition to the first slitting device 113A, a second slitting device 113B that cuts another continuous base sheet 20 for forming a plurality of long base portions 2 on the upper surface side of the sheet-like article 1 illustrated in FIG. 7. The first slitting device 113A and the second slitting device 113E each include a rotary die 111*b* and a receiving roller 112. Further, the manufacturing device 100B not only includes a first adhesive application unit 120A upstream of the water-absorbent polymer dispersion unit 130, but also includes a second adhesive application unit 120B downstream of the water-absorbent polymer dispersion unit 130.

A method for manufactured the sheet-like article 1 illustrated in FIG. 7 by using the manufacturing device 100B illustrated in FIG. 8 is described below. First, one continuous base sheet 20 is cut by the first slitting device 113A to thereby form a plurality of long base portions 2, and then, with the first adhesive application unit 120, an adhesive 5 is applied on the surface of first side (upper surface) of all of the long base portions 2 that have been formed. Then, the water-absorbent polymer particles 3 are dispersed on the adhesive 5 applied on the surface of the first side (upper surface) of the plurality of long base portions 2, and an adhesive 5 is further applied by the second adhesive application unit 120B on the surface of the first side (upper surface) of the dispersed water-absorbent polymer particles 3. Separately, another continuous base sheet 20 is cut by the second slitting device 113B to thereby form a plurality of second long base portions 2. Then, the second long base portions 2 formed by cutting with the second slitting device 113B are arranged on the adhesive 5 applied onto the water-absorbent polymer particles 3 dispersed on the surface of the first side (upper surface) of the plurality of long base portions 2. Thereby, the sheet-like article 1 illustrated in FIG. 7 can be manufacture.

The sheet-like article 1 illustrated in FIG. 7 can achieve the effect that the water-absorbent polymer particles 3 are prevented from scattering and falling off during transportation.

Figure 9:
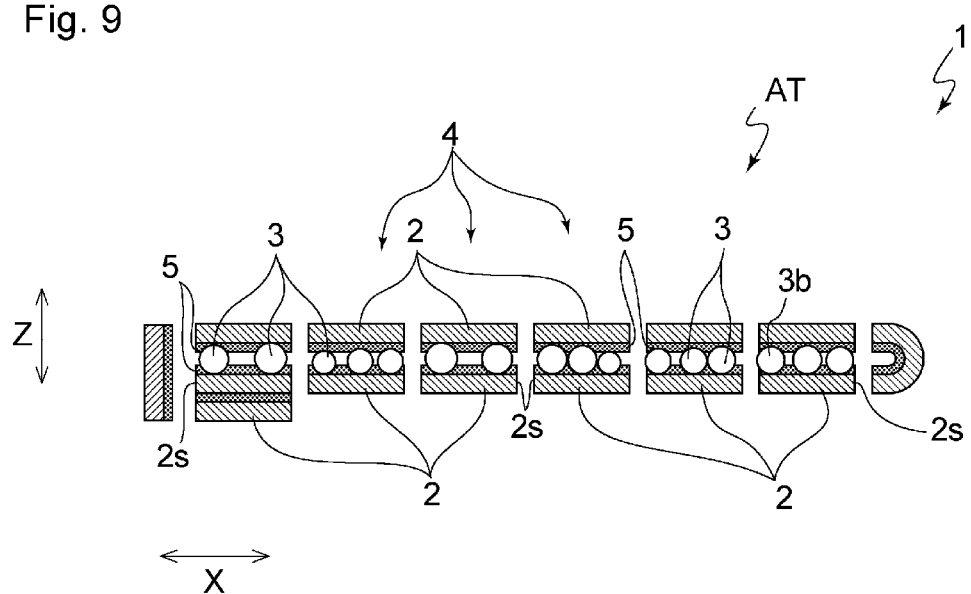
FIG. 9 is a cross-sectional view schematically illustrating another embodiment of a sheet-like article of the invention, the figure illustrating a state before water-absorbent polymer particles absorb a liquid (corresponding to FIG. 1).

The sheet-like article 1 illustrated in FIG. 9 is in a state before use, and has a similar configuration to the sheet-like article 1 illustrated in FIG. 7 and is configured such that: water-absorbent polymer particles 3 are fixed on a surface of first side (upper surface) of long base portions 2 by an adhesive 5; an adhesive 5 is further arranged on the water-absorbent polymer particles 3; and long base portions 2 are further arranged on the adhesive 5. Stated differently, the sheet-like article 1 illustrated in FIG. 9 is configured such that the water-absorbent polymer particles 3 are fixed by enveloping the water-absorbent polymer particles 3 with the plurality of long base portions 2 on which the adhesive 5 has been applied to the surface of first side thereof.

The sheet-like article 1 illustrated in FIG. 9 can be manufactured as follows. For example, by using the manufacturing device 100 illustrated in FIG. 4, a plurality of long base portions 2 are formed by cutting a continuous base sheet 20, and then, an adhesive 5 is applied on the surface of first side (upper surface) of all of the long base portions 2 that have been formed. Then, the water-absorbent polymer particles 3 are dispersed only on the adhesive 5 applied on the surface of the first side (upper surface) of a plurality of the long base portions 2 that are located, for example, on the right side of a position at a distance toward the right from a bisecting position in the orthogonal/cross direction (X1 direction), for example. Then, a plurality of the long base portions 2 that do not have the water-absorbent polymer particles 3 dispersed thereon and that have the adhesive 5 applied on the surface of the first side (upper surface) are folded by using a known fold-back plate onto the long base portions 2 having the water-absorbent polymer particles 3 fixed thereon, and are further folded back so as to envelop the water-absorbent polymer particles 3.

The sheet-like article 1 illustrated in FIG. 9 can achieve the effect that the water-absorbent polymer particles 3 are prevented from scattering and falling off during transportation.

Figure 10:
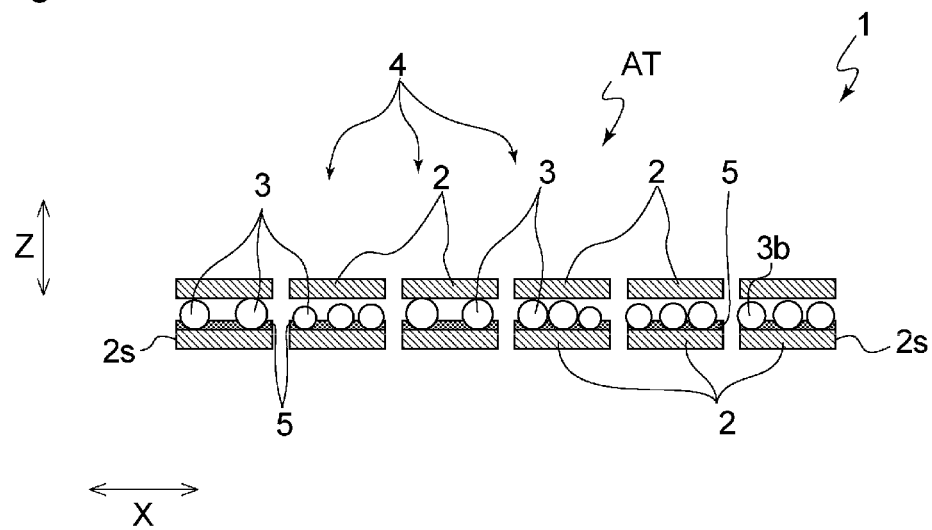
FIG. 10 is a cross-sectional view schematically illustrating another embodiment of a sheet-like article of the invention, the figure illustrating a state before water-absorbent polymer particles absorb a liquid (corresponding to FIG. 1).

The sheet-like article 1 illustrated in FIG. 10 is in a state before use, and is configured such that: water-absorbent polymer particles 3 are fixed on a surface of first side (upper surface) of long base portions 2 by an adhesive 5; and long base portions 2 are further arranged on the water-absorbent polymer particles 3.

The sheet-like article 1 illustrated in FIG. 10 can be manufactured as follows. For example, by using the manufacturing device 100 illustrated in FIG. 4, a plurality of long base portions 2 are formed by cutting a continuous base sheet 20. Then, an adhesive 5 is applied only on the surface of first side (upper surface) of a plurality of the long base portions 2 that are located, for example, on the right side of a bisecting position in the orthogonal/cross direction (X1 direction), for example, and then the water-absorbent polymer particles 3 are dispersed only on the applied adhesive 5. Then, a plurality of the long base portions 2 that are located on the left side of the bisecting position in the orthogonal/cross direction (X1 direction) and that do not have any adhesive 5 applied on the surface of the first side (upper surface) are folded onto the water-absorbent polymer particles 3 located on the aforementioned right side by using a known fold-back plate.

The sheet-like article 1 illustrated in FIG. 10 can achieve the effect that the water-absorbent polymer particles 3 are prevented from scattering and falling off during transportation.

Figure 11:
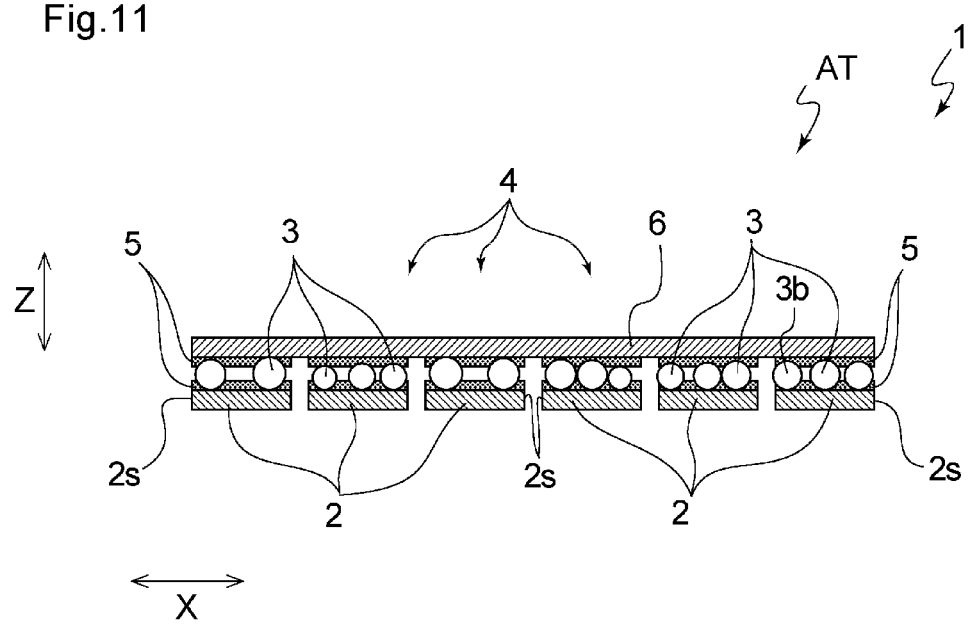
FIG. 11 is a cross-sectional view schematically illustrating another embodiment of a sheet-like article of the invention, the figure illustrating a state before water-absorbent polymer particles absorb a liquid (corresponding to FIG. 1).

The sheet-like article 1 illustrated in FIG. 11 is in a state before use, and is configured such that: water-absorbent polymer particles 3 are fixed on a surface of first side (upper surface) of long base portions 2 by an adhesive 5; an adhesive 5 is further arranged on the water-absorbent polymer particles 3; and a second base sheet 6 that has a wider width than the long base portion 2 and that is different from the base sheet (first base sheet) from which the long base portions 2 were formed is further arranged on the adhesive 5. Stated differently, the sheet-like article 1 illustrated in FIG. 11 is configured such that the water-absorbent polymer particles 3 are fixed by sandwiching the water-absorbent polymer particles 3 by the long base portions 2 on which the adhesive 5 has been applied on the surface of first side thereof and the second base sheet 6 on which the adhesive 5 has been applied on the surface of first side thereof.

Figure 12:
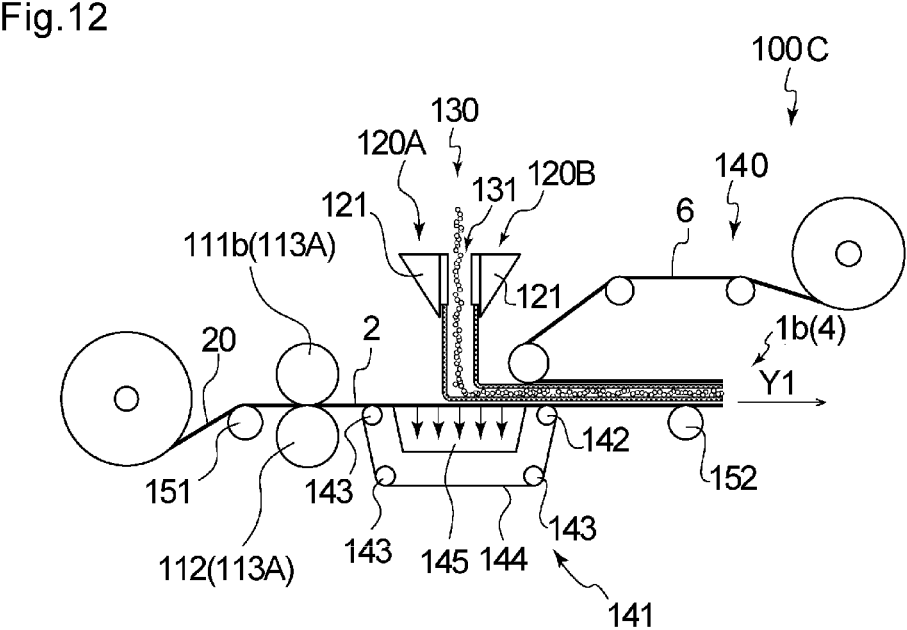
FIG. 12 is a schematic diagram illustrating an embodiment of a device for manufacturing the sheet-like article illustrated in FIG. 11.

The sheet-like article 1 illustrated in FIG. 11 can be manufactured using, for example, a manufacturing device 100C illustrated in FIG. 12. The manufacturing device 100C not only includes a first adhesive application unit 120A upstream of the water-absorbent polymer dispersion unit 130, but also includes a second adhesive application unit 120B downstream of the water-absorbent polymer dispersion unit 130. The manufacturing device also includes a transportation device 140 that transports the second base sheet 6 on the upper surface side of the sheet-like article 1 illustrated in FIG. 11.

A method for manufactured the sheet-like article 1 illustrated in FIG. 11 by using the manufacturing device 100C illustrated in FIG. 12 is described below. First, a continuous first base sheet 20 is cut by the first slitting device 113A to thereby form a plurality of long base portions 2, and then, with the first adhesive application unit 120A, an adhesive 5 is applied on the surface of first side (upper surface) of all of the long base portions 2 that have been formed. Then, the water-absorbent polymer particles 3 are dispersed on the adhesive 5 applied on the surface of the first side (upper surface) of the plurality of long base portions 2, and an adhesive 5 is further applied by the second adhesive application unit 120B on the surface of the first side (upper surface) of the dispersed water-absorbent polymer particles 3. Then, a continuous second base sheet 6 being transported by the transportation device 140 is arranged on the adhesive 5 applied onto the water-absorbent polymer particles 3 dispersed on the surface of the first side (upper surface) of the plurality of long base portions 2. Thereby, the sheet-like article 1 illustrated in FIG. 11 can be manufactured.

The sheet-like article 1 illustrated in FIG. 11 can achieve the effect that the water-absorbent polymer particles 3 are prevented from scattering and falling off during transportation.

The invention is not limited to the foregoing embodiments, and can be modified as appropriate.

In the aforementioned sheet-like articles 1 illustrated in FIGS. 1, 6, 7, and 9 to 11, the water-absorbent polymer particles 3 are fixed only to the surface of first side (upper surface) of the respective long base portions 2. However, from the viewpoint of improving the liquid absorption performance of the sheet-like article 1, the water-absorbent polymer particles may also be fixed to the surface of the second side (lower surface) of the respective long base portions 2, in addition to the surface of the first side (upper surface) thereof. In cases of fixing the water-absorbent polymer particles 3 to both faces (upper and lower surfaces) of the respective long base portions 2, for example, the manufacturing device 100 illustrated in FIG. 4 can be used to: first fix the water-absorbent polymer particles 3 to the surface of first side (upper surface) of the respective long base portions 2; then flip the long base portions 2 over with an inversion roller; then disperse and fix water-absorbent polymer particles 3 onto the surface of the second side (lower surface) of the respective long base portions 2 by using a separate water-absorbent polymer dispersion unit 130, to thereby manufacture the sheet-like article.

In cases of fixing the water-absorbent polymer particles 3 to both faces (upper and lower surfaces) of the respective long base portions 2, from the viewpoint of further achieving the aforementioned effects, it is preferable that the basis weight of the water-absorbent polymer 3 fixed on the surface of the second side (lower surface) of the long base portions 2 is greater than the basis weight of the water-absorbent polymer 3 fixed on the surface of the first side (upper surface) of the long base portions 2. The basis weight of the water-absorbent polymer 3 fixed on the surface of the first side (upper surface) of the long base portions 2 is preferably from 10 to 250 g/m$^2$, more preferably from 30 to 150 g/m$^2$. The basis weight of the water-absorbent polymer 3 fixed on the surface of the second side (lower surface) of the long base portions 2 is preferably from 30 to 400 g/m$^2$, more preferably from 50 to 300 g/m$^2$.

In cases of fixing the water-absorbent polymer 3 to both faces (upper and lower surfaces) of the respective long base portions 2, from the viewpoint of causing the non-skin-facing surface (lower surface), which is farther from the wearer's skin, to retain a large amount of liquid and improving texture to the touch by preventing liquid from remaining on the skin-facing surface (upper surface), it is preferable that the water-absorbent polymer 3 fixed on the surface of the first side (upper surface) of the long base portions 2 has a higher liquid permeation performance under pressure and a smaller centrifugal retention amount than the water-absorbent polymer 3 fixed on the surface of the second side (lower surface) of the long base portions 2. From the above viewpoint, as for the water-absorbent polymer 3 fixed on the surface of the first side (upper surface) of the long base portions 2, the liquid permeation rate under a pressure of 2.0 kPa is preferably 20 ml/minute or greater, more preferably 40 ml/minute or greater, and preferably 1000 ml/minute or less, more preferably 800 ml/minute or less, and more specifically, preferably from 20 to 1000 ml/minute, more preferably from 40 to 800 ml/minute. As for the water-absorbent polymer 3 fixed on the surface of the second side (lower surface) of the long base portions 2, the liquid permeation rate under a pressure of 2.0 kPa is preferably 0 ml/minute or greater, more preferably 10 ml/minute or greater, and preferably 400 ml/minute or less, more preferably 200 ml/minute or less, and more specifically, preferably from 0 to 400 ml/minute, more preferably from 10 to 200 ml/minute. The liquid permeation rate under pressure is found according to the following measurement method.

{Method for Measuring Liquid Permeation Rate Under Pressure}

The liquid permeation rate under pressure is measured by employing the measurement method and measurement device disclosed in JP 2003-235889 A. In a 100-ml glass beaker, 0.32±0.005 g of the water-absorbent polymer, which is the sample to be measured, is immersed in a sufficient amount of physiological saline solution (0.9 mass % sodium chloride aqueous solution) sufficient for swelling the water-absorbent polymer—e.g., a physiological saline solution in an amount equal to or more than 5 times the saturation absorption amount of the water-absorbent polymer—and the sample is left for 30 minutes. Provided separately is a filter cylindrical tube in which a metal mesh (mesh opening: 150 μm; bio-column sintered stainless steel filter 30SUS sold by Sansyo Co., Ltd.) and a fine tube (inner diameter: 4 mm; length: 8 cm) with a valve (inner diameter: 2 mm) are provided to the lower end of an opening in a vertically-arranged cylinder (inner diameter: 25.4 mm). In a state where the valve is closed, the whole content of the aforementioned beaker, including the swollen measurement sample, is poured into the cylindrical tube. Then, a 2-mm-dia. circular cylindrical rod having, at its tip end, a metal mesh with a mesh opening of 150 μm and a diameter of 25 mm is inserted into the filter cylindrical tube so that the metal mesh comes into contact with the measurement sample, and further, a weight is placed on the measurement sample such that a load of 2.0 kPa is applied thereto. The sample is left in this state for 1 minute, the valve is opened to let the liquid pass through, and the time (T1) (seconds)

from when the liquid level inside the filter cylindrical tube is at the 60 ml scale line to when the liquid level reaches the 40 ml scale line (i.e., the time required for 20 ml of liquid to pass through) is measured. By using the measured time T1 (seconds), the liquid permeation rate under a pressure of 2.0 kPa is calculated from the equation below. In the equation, T0 (seconds) is a measurement value of the time required for 20 ml of physiological saline solution to pass through the metal mesh when no measurement sample is placed inside the filter cylindrical tube.

$$\text{Liquid permeation rate under pressure (ml/min)}=20\times 60/(T1-T0)$$

The measurement is performed five times (n=5); the highest and lowest values are eliminated, and the average value of the remaining three samples is found as the measurement value. The measurement is performed at 23±2° C. at a humidity of 50±5%, and the sample is stored in this environment for 24 hours or longer before measurement. The method for measuring the liquid permeation rate under pressure is described in further detail in paragraphs {0008} and {0009} of JP 2003-235889 A, and the measurement device is illustrated in FIGS. 1 and 2 of the same publication.

From the aforementioned viewpoint, as for the water-absorbent polymer 3 fixed on the surface of the first side (upper surface) of the long base portions 2, the centrifugal retention amount (water absorption amount) is preferably 20 g/g or greater, more preferably 25 g/g or greater, and preferably 50 g/g or less, more preferably 45 g/g or less, and more specifically, preferably from 20 to 50 g/g, more preferably from 25 to 45 g/g. As for the water-absorbent polymer 3 fixed on the surface of the second side (lower surface) of the long base portions 2, the centrifugal retention amount (water absorption amount) is preferably 25 g/g or greater, more preferably 30 g/g or greater, and preferably 65 g/g or less, more preferably 55 g/g or less, and more specifically, preferably from 25 to 65 g/g, more preferably from 30 to 55 g/g. The centrifugal retention amount (water absorption amount) is found according to the following measurement method.

{Method for Measuring Centrifugal Retention Amount (Water Absorption Amount)}

The centrifugal retention amount (water absorption amount) is measured in compliance with JIS K 7223 (1996). A nylon woven fabric (sold by Sanriki Seisakusho; product name: nylon mesh; specification: 250 mesh) is cut into a rectangle that is 10 cm wide and 40 cm long, the rectangle is folded into two at the longitudinal center, and both ends are heat-sealed, to prepare a nylon bag that is 10 cm wide (inner dimension: 9 cm) and 20 cm long. Next, 1.00 g of the water-absorbent polymer, which is the sample to be measured, is weighed precisely, and is placed uniformly at the bottom of the prepared nylon bag. Then, the nylon bag containing the sample is immersed in a physiological saline solution (0.9 mass % sodium chloride aqueous solution) whose temperature has been adjusted to 25° C. After 1 hour from the start of immersion, the nylon bag is removed from the physiological saline solution, is hung in a vertical state for 1 hour to drain, and is then dehydrated by using a centrifugal drier (product of Kokusan Co., Ltd.; model: H-130C special). The dehydration is performed at 143 G (800 rpm) for 10 minutes. After dehydration, the mass of the sample is measured, and the centrifugal retention amount (water absorption amount) to be found is calculated according to the equation below.

$$\text{Centrifugal retention amount (g/g)}=(a'-b-c)/c$$

In the equation, a' is the total mass (g) of the centrifugally-dehydrated sample and the nylon bag, b is the mass (g) of the nylon bag before water absorption (when dry), and c is the mass (g) of the sample before water absorption (when dry).

The measurement is performed five times (n=5); the highest and lowest values are eliminated, and the average value of the remaining three samples is found as the measurement value. The measurement is performed at 23±2° C. at a humidity of 50±5%, and the sample is stored in this environment for 24 hours or longer before measurement.

The aforementioned sheet-like article 1 illustrated in FIG. 1 is formed by using a plurality of absorbent units 4 including long base portions 2 with a uniform width. The width of the long base portion 2, however, may be nonuniform. Preferably, in a planar view of the sheet-like article 1, the water-absorbent polymer particles 3 may be fixed in an unevenly distributed manner; and in a section where the basis weight of the fixed water-absorbent polymer 3 is relatively high, the distance between both lateral side edge portions 2s, 2s, of each long base portion 2, that extend along the longitudinal direction (Y direction) may be relatively short. Stated differently, when comparing a section where the basis weight of the fixed water-absorbent polymer 3 is large and a section where the basis weight is small, the distance between each long base portion 2's both lateral side edge portions 2s, 2s in a section where the basis weight of the fixed water-absorbent polymer 3 is large may be made shorter than the distance between each long base portion 2's both lateral side edge portions 2s, 2s in a section where the basis weight of the fixed water-absorbent polymer 3 is small. With the sheet-like article 1 configured as above, in a section where the basis weight of the fixed water-absorbent polymer 3 is large, the adjacent absorbent units 4, 4 are facilitated to move freely in the thickness direction (Z direction) and the sheet-like article 1 is less likely to become stiff, and also, it is possible to make full use of the absorption performance of the water-absorbent polymer particles 3 and the absorption performance of the sheet-like article 1 is easily improved.

Figure 13:
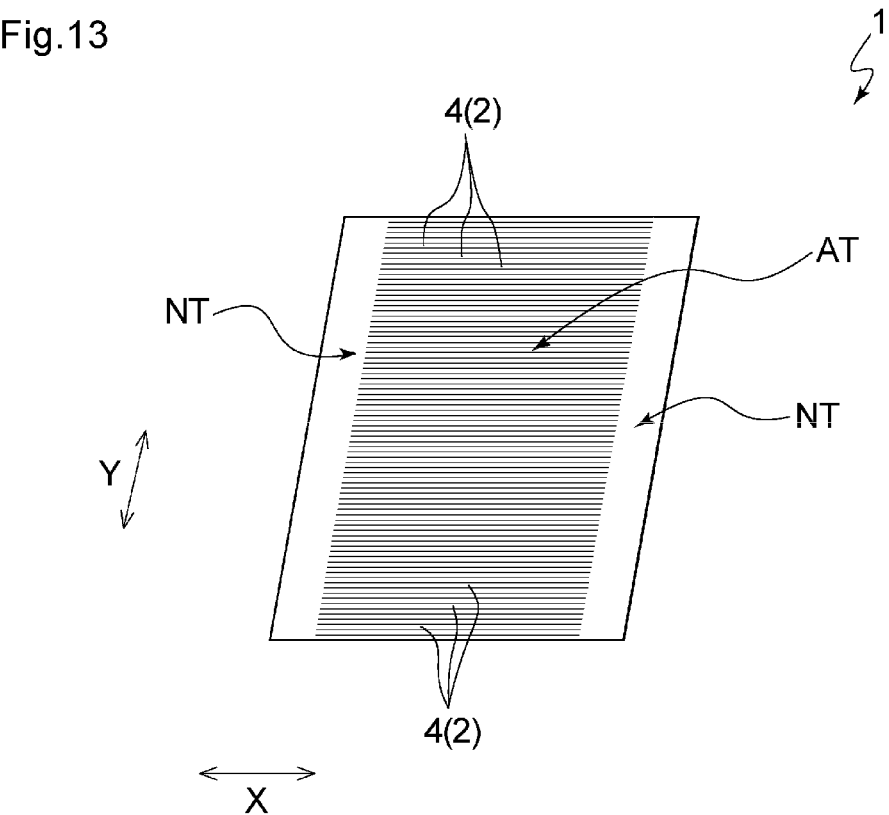
FIG. 13 is a perspective view as viewed from an upper surface side of yet another embodiment of a sheet-like article of the invention, the figure illustrating a state before water-absorbent polymer particles absorb a liquid (corresponding to FIG. 3).

Further, in the aforementioned sheet-like article 1 illustrated in FIG. 3, the absorbent units 4 are formed so that their longitudinal direction (Y direction) is oriented along the longitudinal direction (Y direction) of the sheet-like article 1, but instead, as illustrated in FIG. 13 for example, the absorbent units 4 may be arranged so that their longitudinal direction (Y direction) is oriented in the lateral direction (X direction) of the sheet-like article 1. The sheet-like article 1 illustrated in FIG. 13 includes non-slit regions NT respectively in both lateral sides extending along the longitudinal direction (Y direction). When manufacturing the sheet-like article 1 illustrated in FIG. 13, the sheet-like article can be formed by using a receiving roller and a rotary die in which cutter blades arranged parallel to one another in the axial direction of the roller are arranged intermittently in the circumferential direction, and supplying the base sheet 20 between the rotary die and the receiving roller.

Further, the sheet-like article 1 may be formed by arranging the absorbent units 4 so that their respective longitudinal directions Y are oriented in a plurality of directions. An example of a sheet-like article 1 formed by arranging the absorbent units so as to be oriented in a plurality of directions is a configuration in which: regions in which a plurality of absorbent units 4 are formed so that their longitudinal direction (Y direction) is oriented in the longitudinal direction (Y direction) of the sheet-like article 1 are provided respectively in both lateral sides extending along the longitudinal direction (Y direction) of the sheet-like article 1; and a region in which a plurality of absorbent units 4 are formed so that their longitudinal direction (Y direction) is oriented in the lateral direction (X direction) of the sheet-like article 1 is provided in a central portion sandwiched between the lateral sides. Such a sheet-like article 1 formed by arranging the absorbent units so as to be oriented in a plurality of directions can be formed, for example, by: making a plurality of cuts in both lateral sides extending along the transporting direction (Y1 direction) of the base sheet 20 being transported by using cutter blades 111a and a receiving roller 112; and then making a plurality of cuts in a central section, in the orthogonal/cross direction (X1 direction), in the base sheet 20 being transported by using a receiving roller and a cutting roller having blades arranged intermittently in the circumferential direction.

In the aforementioned sheet-like article 1 illustrated in FIG. 1, the absorbent units 4 and the long base portions 2 extend rectilinearly parallel to the longitudinal direction (Y direction), but their shape is not limited so long as they extend in the longitudinal direction (Y direction). For example, the absorbent units 4 and the long base portions 2 may extend so as to repeatedly depict S shapes in the longitudinal direction (Y direction), or may extend in a zig-zag form along the longitudinal direction (Y direction).

Figure 14:
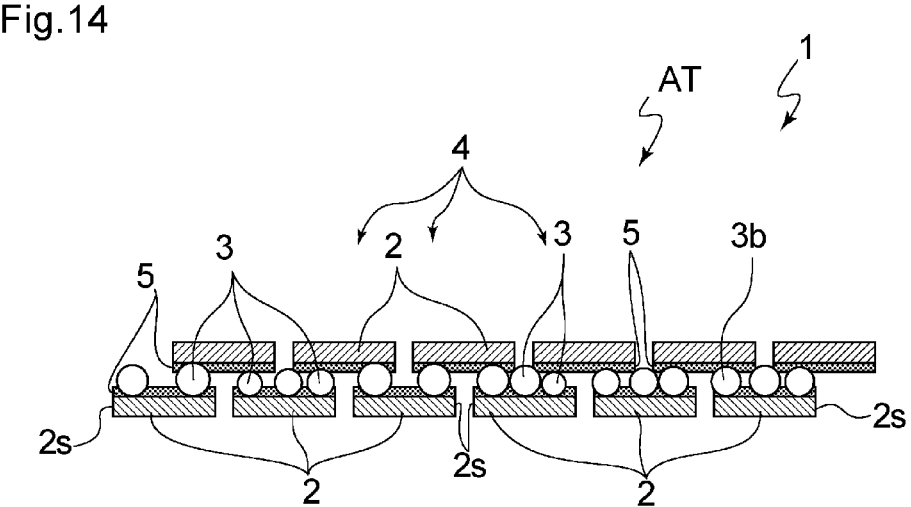
FIG. 14 is a cross-sectional view schematically illustrating another embodiment of a sheet-like article of the invention, the figure illustrating a state before water-absorbent polymer particles absorb a liquid (corresponding to FIG. 1).

Further, in the sheet-like articles 1 illustrated in FIGS. 7 and 10, in a state before use, the long base portions 2 arranged on the lower surface side of the water-absorbent polymer particles 3 and the long base portions 2 arranged on the upper surface side of the water-absorbent polymer particles 3 are arranged at the same positions in the thickness direction (Z direction), but their positions may be misaligned in the lateral direction (X direction), as in the sheet-like article 1 illustrated in FIG. 14, for example.

Further, in the aforementioned method for manufacturing the sheet-like articles 1 of the foregoing embodiments, an adhesive application step is provided after the cutting step, and a water-absorbent polymer dispersion step is provided after the adhesive application step, but in cases where the surface of first side of the base sheet 20 is to be napped, a napping step may be provided instead of the adhesive application step. The napping step may be provided before the cutting step. Examples of methods for performing napping include methods described in JP 2012-092476 A and JP 2013-028891 A.

Figure 15:
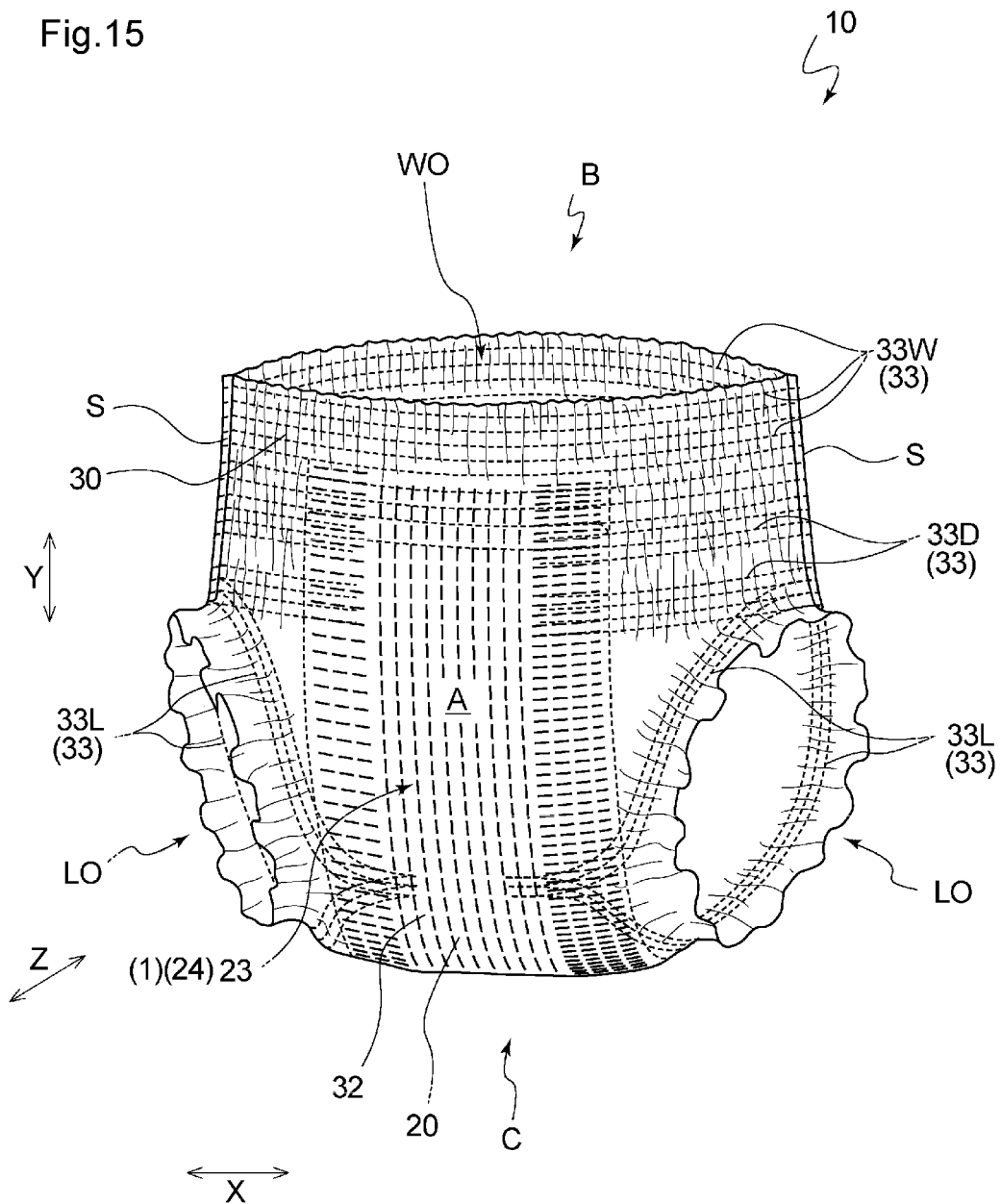
FIG. 15 is a perspective view of a pull-on disposable diaper which is an embodiment of an absorbent article of the invention.
Figure 16:
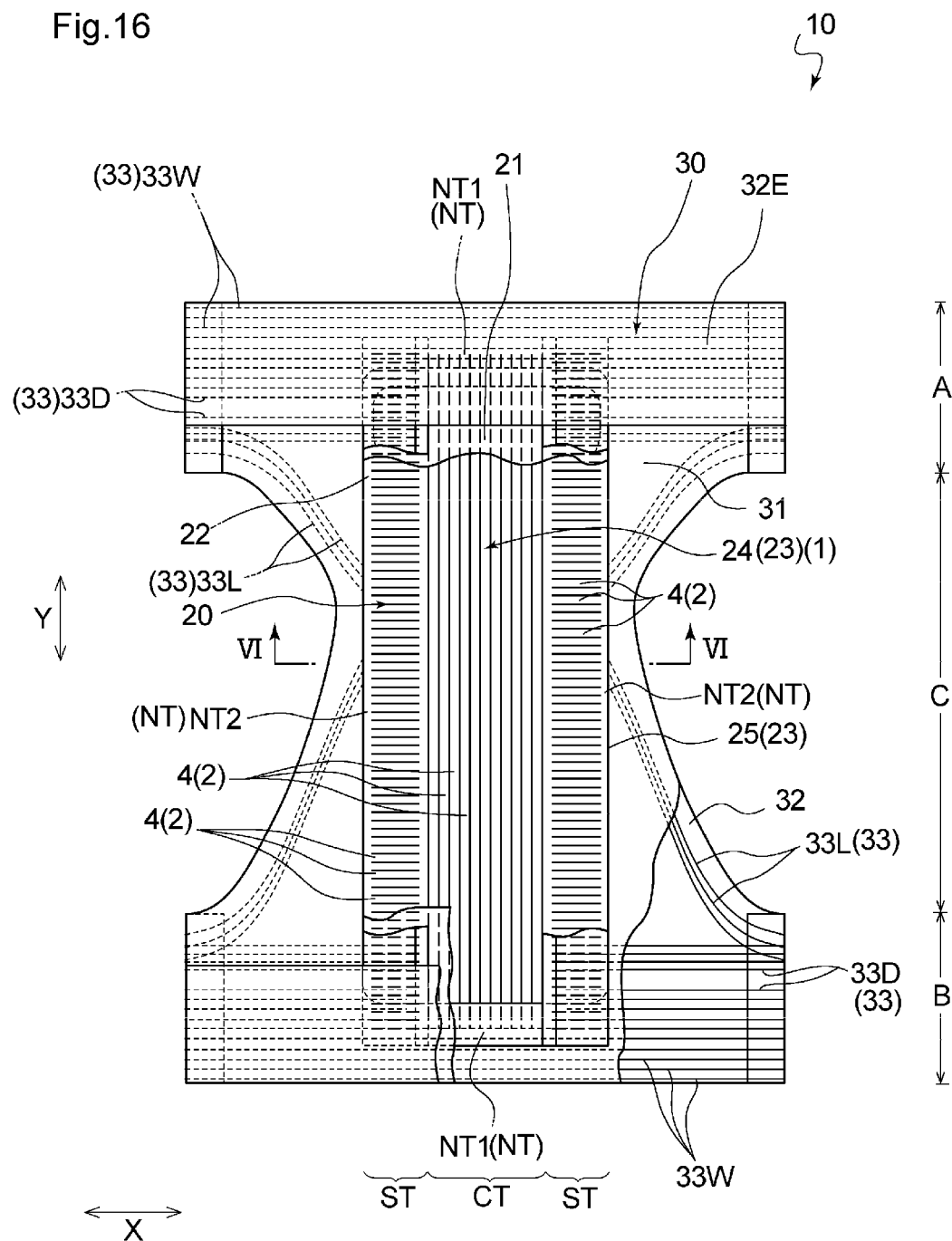
FIG. 16 is a partially cutaway plan view illustrating a state in which the diaper of FIG. 15 has been spread out (opened) by tearing the side seals apart and has been stretched and spread out in a planar manner.

Next, an absorbent article of the inventions described according to preferred embodiments thereof with reference to the drawings. FIG. 15 illustrates a perspective view of a natural state of a disposable diaper 10 (also referred to hereinafter simply as "diaper 10") which is an embodiment of an absorbent article of the invention. FIG. 16 is a plan view as viewed from the topsheet side, illustrating a state in which the diaper 10 of FIG. 15 has been spread out (opened) and stretched in a planar manner by tearing its side seals S apart. The diaper 10 illustrated in FIGS. 15 and 16 is, a so-called pull-on disposable diaper. The diaper 10 includes an absorbent assembly 20 including a topsheet 21, a backsheet 22, and an absorbent member 23 interposed between the topsheet 21 and the backsheet 22, and has an article longitudinal direction Y corresponding to a wearer's front-to-rear direction, and an article lateral direction X orthogonal to the article longitudinal direction Y. Preferably, the diaper 10 includes the absorbent assembly 20, and an outer cover 30 located on the non-skin-facing surface side of the absorbent assembly 20. The diaper 10 is divided into: a front portion A to be arranged on the wearer's front side when worn; a rear portion B to be arranged on the wearer's rear side; and a crotch portion C located therebetween. The crotch portion C is a region where the later-described outer cover 30's lateral side edges are narrowed inward in the article lateral direction X, and is arranged in the wearer's crotch section when the diaper 10 is worn. The front portion A is a region located more toward the wearer's front side than the crotch portion C when the diaper 10 is worn. The rear portion B is a region located more toward the wearer's rear side than the crotch portion C when the diaper 10 is worn. The diaper 10 has an article thickness direction Z in its thickness direction.

In the present Description, the "skin-facing surface side" refers to the side (face), of the front and rear sides (faces) of each member of the diaper 10, that is arranged on the wearer's skin side when the diaper 10 is worn. The "non-skin-facing surface side" refers to the side (face), of the front and rear sides (faces) of each member of the diaper 10, that is arranged on the opposite side from the wearer's skin side when the diaper 10 is worn. Further, in the following explanation, the "article longitudinal direction Y" refers to the direction extending from the front portion A to the rear portion B in the diaper 10 in a state spread out in a planar manner. The "article lateral direction X" is the direction orthogonal to the article longitudinal direction Y of the diaper 10 in a state spread out in a planar manner, and refers to the width direction of the diaper 10 in a state spread out in a planar manner.

As illustrated in FIG. 16, in the diaper 10, the absorbent assembly 20 has a rectangular shape that is oblong in longitudinal direction, and is joined to a central area, in the article lateral direction X, of the outer cover 30 by a known joining means, such as a hot-melt adhesive, in a manner that the absorbent assembly 20 extends from the front portion A up to the rear portion B with the absorbent assembly's article longitudinal direction Y matching the diaper 10's article longitudinal direction Y. The outer cover 30's both lateral side edge portions in a section located in the front portion A are joined together with the outer cover's respective lateral side edge portions in a section located in the rear portion B by a known joining means such as heat sealing, ultrasonic sealing, or the like. Thus, a pair of side seals S is formed in the diaper 10. This joining also forms, in the diaper 10, a waist opening WO and a pair of leg openings LO, LO as illustrated in FIG. 15, and the outer cover 30 is thus formed into a three-dimensional pull-on shape.

As illustrated in FIG. 16, in the diaper 10, the outer cover 30 includes an inner sheet 31, an outer sheet 32, and thread-form elastic members 33 in various sections and that are fixed between the two sheets. The inner sheet 31 and the outer sheet 32 have the same shape in the article lateral direction X. In the article longitudinal direction Y, however, the outer sheet 32 extends out from the front and rear end portions of the inner sheet 31, and the extension portions 32E cover the respective front and rear end regions, in the article longitudinal direction Y, of the absorbent assembly 20. The outer edge of the outer cover 30 constitutes the contour of the spread-out diaper 10.

As illustrated in FIGS. 15 and 16, in the diaper 10, the thread-form elastic members 33 include: waist elastic members 33W that are arranged between the inner sheet 31 and the outer sheet 32 and that form waist gathers in the peripheral edge section of the waist opening WO; leg elastic members 33L that form leg gathers in the peripheral edge section of each leg opening LO; and below-waist elastic members 33D that form below-waist gathers in a below-waist portion (a region from a position 20 mm below the peripheral edge of the waist opening WO to the upper end of the leg openings LO). The waist elastic members 33W, the leg elastic members 33L, and the below-waist elastic members 33D are joined and fixed in their stretched state by a joining means such as a hot-melt adhesive.

Figure 17:
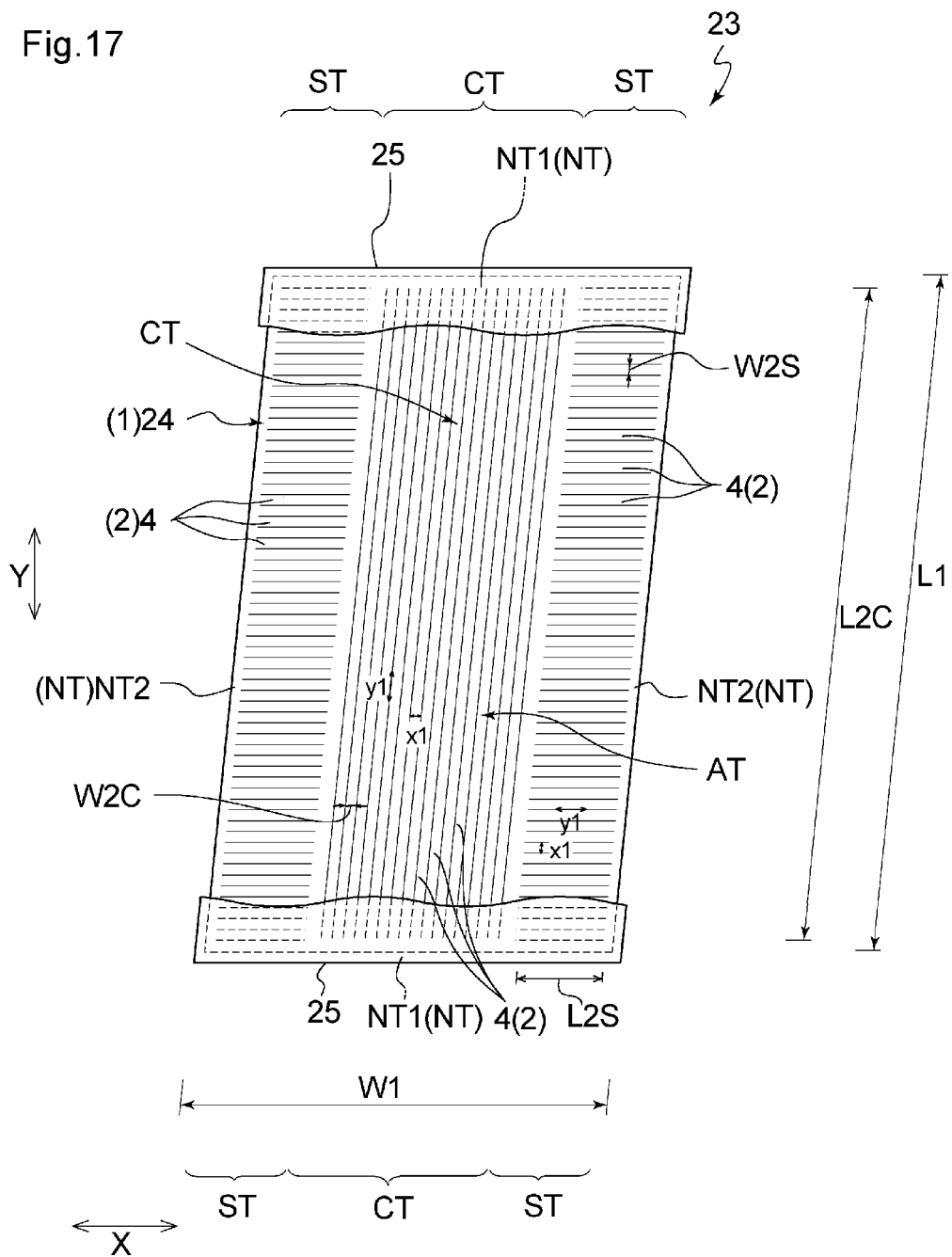
FIG. 17 is a partially cutaway perspective view of an absorbent member provided in the diaper illustrated in FIG. 15.

As illustrated in FIG. 16, in the diaper 10, the absorbent assembly 20 includes an absorbent member 23. As illustrated in FIG. 17, the absorbent member 23 includes an absorbent core 24, and a liquid-permeable core-wrap sheet 25 that covers the absorbent core 24. As illustrated in FIG. 17, in a planar view, the absorbent core 24 has a rectangular shape that is long in the article longitudinal direction Y. The absorbent member 23 is formed by covering the entire absorbent core 24 with the core-wrap sheet 25. In the absorbent article, a so-called sublayer sheet may be arranged on at least one of the skin-facing surface and the non-skin-facing surface of the absorbent member 23.

As illustrated in FIG. 17, in the diaper 10, the absorbent core 24 is formed of a sheet-like article 1 including a plurality of the absorbent units 4, each absorbent unit 4 including: a long base portion 2 having a lateral direction (x1 direction), a longitudinal direction (y1 direction) that is longer than the lateral direction (x1 direction), and a thickness direction (z1 direction); and water-absorbent polymer particles 3 (also referred to hereinafter simply as "water-absorbent polymer 3") that are fixed to a surface of first side of the long base portion 2, wherein the absorbent units 4 are arranged such that the absorbent unit 4's longitudinal direction (y1 direction) is oriented at least in one direction. Herein, the lateral direction (x1 direction), longitudinal direction (y1 direction), and thickness direction (z1 direction) of the long base portion 2 match the lateral direction (x1 direction), longitudinal direction (y1 direction), and thickness direction (z1 direction) of the absorbent unit 4. Note that, as illustrated in FIG. 17, the sheet-like article 1, which is the absorbent core 24, has a longitudinally-oblong rectangular shape that is long in the article longitudinal direction Y and short in the article lateral direction X in a planar view, and is arranged so as to extend from the front portion A up to the rear portion B with its article longitudinal direction Y matching the absorbent assembly 20's article longitudinal direction Y or the diaper 10's article longitudinal direction Y. The long base portion 2's thickness direction (z1 direction) and the absorbent unit 4's thickness direction (z1 direction) match the article thickness direction Z.

In the diaper 10, as illustrated in FIG. 17, the absorbent core 24 formed of the sheet-like article 1 includes, in a planar view, a central region CT in a central area in the article lateral direction X, and a pair of side regions ST, ST provided more outward, in the article lateral direction X, than the central region CT. The central region CT is located in a central area, in the article lateral direction X, of the absorbent core 24 and extends between both end portions, in the article longitudinal direction Y, of the absorbent core 24. The pair of side regions ST, ST is located more outward, in the article lateral direction X, than the central region CT, and extends between both end portions, in the article longitudinal direction Y, of the absorbent core 24.

Figure 18:
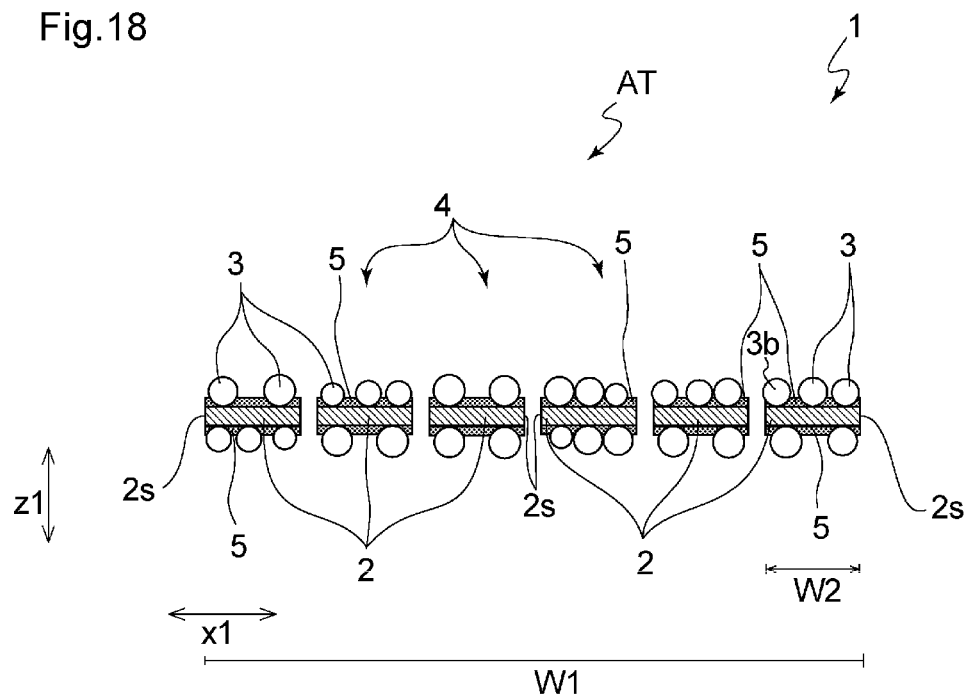
FIG. 18 is a cross-sectional view schematically illustrating an embodiment of a sheet-like article, which is an absorbent core of the absorbent member illustrated in FIG. 17, the figure illustrating a state before water-absorbent polymer particles absorb a liquid.
Figure 19:
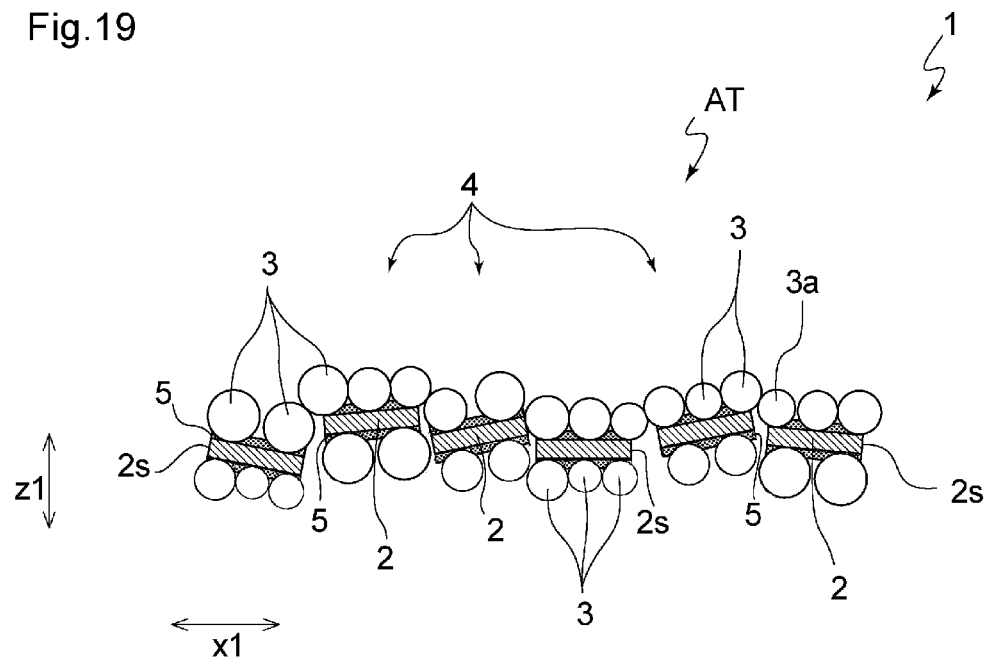
FIG. 19 is a cross-sectional view schematically illustrating a state in which the water-absorbent polymer particles in the sheet-like article illustrated in FIG. 18 have swollen by absorbing a liquid.

FIGS. 18 and 19 are cross-sectional views schematically illustrating the sheet-like article 1 which is the absorbent core 24. The sheet-like article 1 of FIG. 18 shows a state before water-absorbent polymer particles absorb a liquid (also referred to hereinafter simply as "a state before use"). The sheet-like article 1 of FIG. 19 shows a state in which the water-absorbent polymer particles have swollen by absorbing a liquid (also referred to hereinafter simply as "state after swelling"). Herein, a "state after swelling" refers to a state of the water-absorbent polymer particles after immersing the sheet-like article 1 in a physiological saline solution (0.9 mass % sodium chloride aqueous solution), whose temperature has been adjusted to 25° C., for 60 minutes.

As illustrated in FIGS. 16 and 17, in each side region ST of the sheet-like article 1, the absorbent units 4 are arranged such that their longitudinal direction (y1 direction) is oriented in the article lateral direction X. In the diaper 10, each side region ST is formed by arranging a plurality of absorbent units 4 such that the absorbent unit 4's longitudinal direction (y1 direction) is oriented in the sheet-like article 1's article lateral direction X. Preferably, the plurality of absorbent units 4 are arranged parallel to the article lateral direction X such that the absorbent units 4 do not intersect with one another. Each side region ST in the sheet-like article 1 illustrated in FIG. 17 is formed by using a plurality of the absorbent units 4 respectively including long base portions 2 with a uniform width, and by arranging the absorbent units 4 side by side in the article longitudinal direction Y and parallel to the article lateral direction X of the sheet-like article 1 such that the longitudinal direction (y1 direction) of the absorbent units 4 is oriented along the article lateral direction X of the sheet-like article 1.

As illustrated in FIG. 17, in each side region ST, from the viewpoint of facilitating movement of the absorbent units 4, there is no intervening member present between the absorbent units 4, 4 adjacent to one another in the lateral direction (x1 direction) of the long base portions 2 (absorbent units 4). Stated differently, the absorbent unit 4 in each side region ST is not wrapped by an intervening member. In FIGS. 18 and 19, the upper surface which is the first side of the long base portions 2 is the skin-facing surface that faces the wearer's skin, and the lower surface which is the second side of the long base portions 2 is the non-skin-facing surface that faces the backsheet.

Further, in the diaper 10, as illustrated in FIGS. 16 and 17, in the central region CT of the sheet-like article 1 which is the absorbent core 24, the absorbent units 4 are arranged such that their longitudinal direction (y1 direction) is oriented in the article longitudinal direction Y. Preferably, in the diaper 10, the central region CT is formed by arranging a plurality of absorbent units 4 such that the absorbent unit 4's longitudinal direction (y1 direction) is oriented in the sheet-like article 1's article longitudinal direction Y. More preferably, the plurality of absorbent units 4 are arranged parallel to the article longitudinal direction Y such that the absorbent units 4 do not intersect with one another. The central region CT in the sheet-like article 1 illustrated in FIG. 17 is formed by using a plurality of the absorbent units 4 respectively including long base portions 2 with a uniform width, and by arranging the absorbent units 4 side by side in the article lateral direction X and parallel to the article longitudinal direction Y of the sheet-like article 1 such that the longitudinal direction (y1 direction) of the absorbent units 4 is oriented along the article longitudinal direction Y of the sheet-like article 1. In the central region CT, from the viewpoint of facilitating movement of the absorbent units 4, there is no intervening member present between the absorbent units 4, 4 adjacent to one another in the lateral direction (x1 direction) of the long base portions 2 (absorbent units 4). Stated differently, the absorbent unit 4 in the central region CT is not wrapped by an intervening member.

As illustrated in FIG. 17, in a state before use, the sheet-like article 1, which is the absorbent core 24, includes an absorbent region AT in which a plurality of the absorbent units 4 are arranged so as to be oriented in one direction. In this diaper 10, the absorbent region AT refers to a region combining: regions, in the respective side regions ST, wherein the absorbent units 4 are arranged such that their longitudinal direction (y1 direction) is oriented in the article lateral direction X as illustrated in FIGS. 16 and 17; and a region, in the central region CT, wherein the absorbent units 4 are arranged such that their longitudinal direction (y1 direction) is oriented in the article longitudinal direction Y. From the viewpoint of facilitating absorption of liquid by the regions in which the water-absorbent polymer particles 3 are fixed, in a planar view of the sheet-like article 1 in a state before use, the percentage of the absorbent region AT to the entire sheet-like article 1 is preferably 20% or greater, more preferably 50% or greater, and preferably 100% or less, more preferably 90% or less, and more specifically, preferably from 20 to 100%, more preferably from 50 to 90%. The expression "the percentage of the absorbent region AT is 100%" refers, for example, to a configuration wherein: in each side region ST where the absorbent units 4 are arranged such that their longitudinal direction (y1 direction) is oriented in the article lateral direction X, the absorbent units 4 are arranged so as to span both lateral sides, of each side region ST, that extend along the article longitudinal direction Y; and, in the central region CT where the absorbent units 4 are arranged such that their longitudinal direction (y1 direction) is oriented in the article longitudinal direction Y, the absorbent units 4 are arranged so as to span both end portions, in the article longitudinal direction Y, of the central region CT. Note that, in a planar view of the sheet-like article 1, regions other than the absorbent region AT constitute non-slit regions NT described further below.

In each side region ST, in cases where the longitudinal direction (y1 direction) of the absorbent units 4 is arranged so as to be oriented along the article lateral direction X, it is preferable that preferably 10 pieces or more, more preferably 50 pieces or more, and preferably 3500 pieces or fewer, more preferably 1700 pieces or fewer, and more specifically, preferably from 10 to 3500 pieces, more preferably from 50 to 1700 pieces, of the absorbent units 4 are arranged in each side region ST.

In the central region CT, in cases where the longitudinal direction (y1 direction) of the absorbent units 4 is arranged so as to be oriented along the article longitudinal direction Y, it is preferable that preferably 2 pieces or more, more preferably 10 pieces or more, and preferably 1000 pieces or fewer, more preferably 500 pieces or fewer, and more specifically, preferably from 2 to 1000 pieces, more preferably from 10 to 500 pieces, of the absorbent units 4 are arranged in the central region CT.

If the absorbent units 4 are arranged in the central region CT such that the longitudinal direction (y1 direction) thereof is oriented in the article lateral direction X, it is preferable that preferably 10 pieces or more, more preferably 50 pieces or more, and preferably 3500 pieces or fewer, more preferably 1700 pieces or fewer, and more specifically, preferably from 10 to 3500 pieces, more preferably from 50 to 1700 pieces, of the absorbent units 4 are arranged in the central region CT.

It is preferable that the sheet-like article 1, which is the absorbent core 24, includes: in each of both end portions in the article longitudinal direction Y, a non-slit region NT in which the plurality of long base portions 2 are connected in the article lateral direction X; or, in each of both lateral sides extending along the article longitudinal direction Y, a non-slit region NT connected in the article longitudinal direction Y. As illustrated in FIG. 17, the diaper 10 of the present embodiment includes non-slit regions NT1, NT1 in the respective end portions in the article longitudinal direction Y, and non-slit regions NT2, NT2 in the respective lateral sides extending along the article longitudinal direction Y.

More specifically, the sheet-like article 1 of the present embodiment includes a single base sheet; non-slit regions NT are provided in the respective end portions in the article longitudinal direction Y and in the respective end portions in the article lateral direction X of the base sheet; and a plurality of long base portions 2 formed by a later-described cutting step are provided between the non-slit regions NT. Providing these non-slit regions NT is advantageous in that, in a state before use, the sheet form of the sheet-like article 1 is easy to maintain and the structure is less prone to getting disarranged, and the sheet is easy to transport during manufacture. Preferably, no water-absorbent polymer particle 3 is arranged in the non-slit regions NT (NT1, NT2). By not arranging any water-absorbent polymer particles 3 in the non-slit regions NT (NT1, NT2), even when liquid is absorbed, the water-absorbent polymer particles 3 are less likely to swell in the non-slit regions NT (NT1, NT2), and thus, even in a state after swelling, the sheet form of the sheet-like article 1 is easy to maintain and the structure is less prone to getting disarranged. Meanwhile, in regions where the water-absorbent polymer particles 3 are fixed, liquid can be absorbed easily, thus being effective in easily striking a balance over the entire sheet-like article 1.

Further, in cases where the non-slit regions NT1, NT1 are provided in the respective end portions in the article longitudinal direction Y, as in the sheet-like article 1 illustrated in FIG. 17, it is preferable that both end portions in the article longitudinal direction Y are fixed to the absorbent article, from the viewpoint that the sheet form of the sheet-like article 1 becomes easy to maintain and the structure becomes less prone to getting disarranged, and also the softness of the absorbent region AT is improved, making it less likely to cause uncomfortableness to the wearer. Herein, in this diaper 10, the absorbent article to which both end portions (non-slit regions NT1, NT1) in the article longitudinal direction Y are fixed refers to the absorbent article's constituent members including at least one of the topsheet 21, the backsheet 22, and the core-wrap sheet 25. In cases where both end portions in the article longitudinal direction Y are fixed to the absorbent article, it is even preferable that no water-absorbent polymer particle 3 is fixed in the non-slit regions NT1. Further, from the viewpoint of improving softness of the absorbent region AT and suppressing uncomfortableness to the wearer, it is particularly preferable that a section where the absorbent units 4 are arranged in the central region CT is not fixed to the absorbent article.

Further, in cases where the non-slit regions NT2, NT2 are provided in the respective lateral sides extending along the article longitudinal direction Y, as in the sheet-like article 1 illustrated in FIG. 17, it is preferable that both lateral sides extending along the article longitudinal direction Y are fixed to the absorbent article, from the viewpoint that the sheet form of the sheet-like article 1 becomes easy to maintain and the structure becomes less prone to getting disarranged, and also the softness of the absorbent region AT is improved, making it less likely to cause uncomfortableness to the wearer. Herein, in the diaper 10, the absorbent article to which both lateral sides (non-slit regions NT2, NT2) extending along the article longitudinal direction Y are fixed refers to at least one constituent member of the absorbent article, selected from the topsheet 21, the backsheet 22, and the core-wrap sheet 25. In cases where both lateral sides extending along the article longitudinal direction Y are fixed to the absorbent article, it is even preferable that no water-absorbent polymer particle 3 is fixed in the non-slit regions NT1. Further, from the viewpoint of improving softness of the absorbent region AT and suppressing uncomfortableness to the wearer, it is particularly preferable that a section where the absorbent units 4 are arranged in each side region ST is not fixed to the absorbent article.

In the diaper 10, the distance between both lateral side edge portions, which extend along the longitudinal direction (y1 direction), of each absorbent unit 4's long base portion 2 arranged in each side region ST of the sheet-like article 1 which is the absorbent core 24 is different from the distance between both lateral side edge portions, which extend along the longitudinal direction (y1 direction), of each absorbent unit 4's long base portion 2 arranged in the central region CT of the sheet-like article 1 which is the absorbent core 24. Herein, the "distance between both lateral side edge portions, which extend along the longitudinal direction (y1 direction), of the long base portion 2" is synonymous with the width (length in the lateral direction (x1 direction)) of the long base portion 2. In cases where the width of the central region CT is greater than the width of each side region ST, it is preferable that the width (W2S) (length in the lateral direction (x1 direction)) (cf. FIG. 17) of a single long base portion 2 arranged in each side region ST is shorter than the width (W2C) (length in the lateral direction (x1 direction)) (cf. FIG. 17) of a single long base portion 2 arranged in the central region CT, from the viewpoint of reducing uncomfortableness in the crotch section. In cases where the width of the central region CT is smaller than the width of each side region ST, it is preferable that the width (W2C) (length in the lateral direction (x1 direction)) (cf. FIG. 17) of a single long base portion 2 arranged in the central region CT is shorter than the width (W2S) (length in the lateral direction (x1 direction)) (cf. FIG. 17) of a single long base portion 2 arranged in each side region ST, from the viewpoint of fittability around the legs when the side regions ST have stood up.

In the central region CT of the sheet-like article 1, from the viewpoint of reducing uncomfortableness by improving bendability (improving softness) in the crotch section, the percentage of the width (W2C) (length in the lateral direction (x1 direction)) of a single long base portion 2 (cf. FIG. 17) to the width (W1) of the sheet-like article 1 (cf. FIG. 17) is preferably 0.1% or greater, more preferably 0.2% or greater, and preferably 20% or less, more preferably 4% or less, and more specifically, preferably from 0.1 to 20%, more preferably from 0.2 to 4%.

Preferably, from the same viewpoint, the width (W2C) of the long base portion 2 in the central region CT is preferably 0.3 mm or greater, more preferably 0.6 mm or greater, and preferably 10 mm or less, more preferably 2 mm or less, and more specifically, preferably from 0.3 to 10 mm, more preferably from 0.6 to 2 mm. Note that the width (W1) of the sheet-like article 1 is from 50 to 300 mm.

In the central region CT of the sheet-like article 1, from the same viewpoint, the percentage of the length (L2C) (length in the longitudinal direction (y1 direction)) of a single long base portion 2 (cf. FIG. 17) to the length (L1) of the sheet-like article 1 (cf. FIG. 17) is preferably 2% or greater, more preferably 20% or greater, and preferably 100% or less, more preferably 98% or less, and more specifically, preferably from 2 to 100%, more preferably from 20 to 98%.

Preferably, from the same viewpoint, the length (L2C) of the long base portion 2 in the central region CT is preferably 20 mm or greater, more preferably 200 mm or greater, and preferably 1000 mm or less, more preferably 980 mm or less, and more specifically, preferably from 20 to 1000 mm, more preferably from 200 to 980 mm. Note that the length (L1) of the sheet-like article 1 is approximately from 100 to 1000 mm.

In each side region ST of the sheet-like article 1, from the viewpoint of shape retainability during stand-up of the side regions ST, the percentage of the length (L2S) (length in the longitudinal direction (y1 direction)) of a single long base portion 2 (cf. FIG. 17) to the width (W1) of the sheet-like article 1 (cf. FIG. 17) is preferably 1.5% or greater, more preferably 3% or greater, and preferably 47% or less, more preferably 40% or less, and more specifically, preferably from 1.5 to 47%, more preferably from 3 to 40%.

Preferably, from the same viewpoint, the length (L2S) of the long base portion 2 in each side region ST is preferably 5 mm or greater, more preferably 10 mm or greater, and preferably 140 mm or less, more preferably 120 mm or less, and more specifically, preferably from 5 to 140 mm, more preferably from 10 to 120 mm.

In each side region ST of the sheet-like article 1, from the viewpoint of fittability around the legs during stand-up of the side regions ST, the percentage of the width (W2S) (length in the lateral direction (x1 direction)) of a single long base portion 2 (cf. FIG. 17) to the length (L1) of the sheet-like article 1 (cf. FIG. 17) is preferably 0.03% or greater, more preferably 0.06% or greater, and preferably 10% or less, more preferably 2% or less, and more specifically, preferably from 0.03 to 10%, more preferably from 0.06 to 2%.

Preferably, from the same viewpoint, the width (W2S) of the long base portion 2 in each side region ST is preferably 0.3 mm or greater, more preferably 0.6 mm or greater, and preferably 10 mm or less, more preferably 2 mm or less, and more specifically, preferably from 0.3 to 10 mm, more preferably from 0.6 to 2 mm.

The long base portions 2 constituting the absorbent units 4 are preferably made of a hydrophilic sheet from the viewpoint of easy diffusibility of liquid in the absorbent region AT and improvement in usage efficiency of the water-absorbent polymer 3. Examples of hydrophilic sheets include paper, nonwoven fabrics, cloths, and synthetic sponge made by foaming synthetic resins, and among the above, nonwoven fabrics are preferably used, from the viewpoint of relatively high tensile strength despite its thinness and capability of achieving softness and thinness. Examples of preferably usable nonwoven fabrics include hydrophilic nonwoven fabrics including hydrophilic fibers as constituent fibers, and hydrophilic nonwoven fabrics including, as constituent fibers, fibers obtained by imparting hydrophilicity to synthetic fibers. The basis weight of the nonwoven fabric is preferably from 5 to 100 g/m$^2$, more preferably from 10 to 40 g/m$^2$.

Various types of polymers conventionally used in the technical field of absorbent articles can be used for the water-absorbent polymer 3 to be fixed to the surface of the first side of the long base portions 2. Examples include sodium polyacrylate, (acrylic acid-vinyl alcohol) copolymer, crosslinked sodium polyacrylate, (starch-acrylic acid) graft polymer, (isobutylene-maleic anhydride) copolymer and saponified products thereof, potassium polyacrylate, and cesium polyacrylate. One type of polymer may be used singly, or two or more types may be used as a mixture. Based on differences in their shape, there are various types of water-absorbent polymer particles 3, such as the amorphous type, block type, barrel type, pellet-agglomeration type, and spherical type; any type of particle may be used. In the sheet-like article 1, spherical-type particles are used.

Examples of methods for fixing the water-absorbent polymer particles 3 to the surface of the long base portions 2 include methods using adhesives and chemical fixing methods employing a hydrogen bond etc., and in cases where the long base portions 2 are a nonwoven fabric or a cloth, the constituent fibers may be napped, and the water-absorbent polymer particles 3 may be fixed among the napped constituent fibers. In the sheet-like article 1 illustrated in FIGS. 18 and 19, an adhesive 5 is employed. More specifically, the water-absorbent polymer particles 3 of the sheet-like article 1 are fixed to the long base portions 2 by means of the adhesive 5. Fixing the water-absorbent polymer particles 3 to the surface of the long base portions 2 by means of the adhesive 5 suppresses the water-absorbent polymer particles 3 from falling off in a state before use of the sheet-like article 1 and in a state after the polymer has swollen.

For example, a hot-melt adhesive may be preferably used for the adhesive 5. Examples of hot-melt adhesives include styrene-based and olefin-based adhesives. Examples of styrene-based hot-melt adhesives that may be used include styrene-butadiene-styrene (SBS) copolymers, styrene-isoprene-styrene (SIS) copolymers, styrene-ethylene-butylene-styrene (SEBS) copolymers which are hydrogenated products of SBS, and blended hot-melt adhesives in which two or more types of the above are blended. Among the above, particularly, a blended hot-melt adhesive including SIS and SBS or a blended hot-melt adhesive including SIS and SEBS is preferably used from the viewpoint of the ease of balancing tack force and cohesive force. The amount of hot-melt adhesive applied is preferably from 0.5 to 100 g/m$^2$, more preferably from 5 to 50 g/m$^2$.

In the sheet-like article 1, the water-absorbent polymer particles 3 only need to be fixed only to the surface of first side (upper surface or lower surface) of the respective long base portions 2, but in the sheet-like article 1 illustrated in FIG. 18, from the viewpoint of improving the liquid absorption performance of the sheet-like article 1, the water-absorbent polymer particles are also fixed to the surface of the second side (lower surface) of the respective long base portions 2, in addition to the surface of the first side (upper surface) thereof. Herein, it is preferable that the type of polymer is the same between the water-absorbent polymer particles 3 arranged on the surface of the first side (upper surface) in the central region CT and the water-absorbent polymer particles 3 arranged on the surface of the first side (upper surface) in the side regions ST. Similarly, it is preferable that the type of polymer is the same between the water-absorbent polymer particles 3 arranged on the surface of the second side (lower surface) in the central region CT and the water-absorbent polymer particles 3 arranged on the surface of the second side (lower surface) in the side regions ST. The following describes, as an example, the water-absorbent polymer particles 3 arranged on the surface of first side (upper surface) and the water-absorbent polymer particles 3 arranged on the surface of the second side (lower surface) in the central region CT.

In cases of fixing the water-absorbent polymer particles 3 to the surface of both faces (upper and lower surfaces) of the respective long base portions 2, from the viewpoint of further achieving the aforementioned effects, it is preferable that the basis weight of the water-absorbent polymer 3 fixed on the surface of the second side (lower surface) of the long base portions 2 is greater than the basis weight of the water-absorbent polymer 3 fixed on the surface of the first side (upper surface) of the long base portions 2. The basis weight of the water-absorbent polymer 3 fixed on the surface of the first side (upper surface) of the long base portions 2 is preferably from 10 to 250 g/m$^2$, more preferably from 30 to 150 g/m$^2$. The basis weight of the water-absorbent polymer 3 fixed on the surface of the second side (lower surface) of the long base portions 2 is preferably from 30 to 400 g/m$^2$, more preferably from 50 to 300 g/m$^2$.

The basis weight of the water-absorbent polymer 3 fixed on the skin-facing surface side of the long base portions 2 and the basis weight of the water-absorbent polymer 3 fixed on the non-skin-facing surface side of the long base portions 2 are measured according to the following method.

{Method for Measuring Basis Weight of Water-Absorbent Polymer 3 Fixed on Skin-Facing Surface Side of Long Base Portions 2 and Basis Weight of Water-Absorbent Polymer 3 Fixed on Non-Skin-Facing Surface Side of Long Base Portions 2}

To prevent the water-absorbent polymer fixed on the non-skin-facing surface side of the long base portions 2 from falling off, the water-absorbent polymer is re-fixed from the upper surface thereof with an adhesive for example. Then, the water-absorbent polymer fixed on the skin-facing surface side is removed from the long base portions 2 with a solvent for example, and the adhesive adhering to the water-absorbent polymer is rinsed off. After drying the water-absorbent polymer, the weight of the water-absorbent polymer that had been fixed on the skin-facing surface side is measured. From the area of the long base portions 2 in the section where the water-absorbent polymer was fixed and the weight of the removed water-absorbent polymer, the weight of the water-absorbent polymer fixed per unit area is calculated, to find the basis weight of the water-absorbent polymer on the skin-facing surface side. The measurement is performed with five sheets, and the average value is calculated.

The basis weight of the water-absorbent polymer on the non-skin-facing surface side is found in a similar manner; the water-absorbent polymer on the skin-facing surface side is fixed, the water-absorbent polymer on the non-skin-facing surface side is removed and rinsed, and the basis weight is calculated.

In cases of fixing the water-absorbent polymer particles 3 to the surface of both faces (upper and lower surfaces) of the respective long base portions 2, from the viewpoint of causing the surface of the non-skin-facing surface (lower surface), which is farther from the wearer's skin, to retain a large amount of liquid and improving texture to the touch by preventing liquid from remaining on the surface of the skin-facing surface (upper surface), it is preferable that the water-absorbent polymer 3 fixed on the surface of the first side (upper surface) of the long base portions 2 has a higher liquid permeation performance under pressure and a smaller centrifugal retention amount than the water-absorbent polymer 3 fixed on the surface of the second side (lower surface) of the long base portions 2. As described here, it is preferable that the type of the water-absorbent polymer 3 fixed on the surface of the first side (upper surface) of the long base portions 2 is different from the type of the water-absorbent polymer 3 fixed on the surface of the second side (lower surface) of the long base portions 2. Herein, "the type of the water-absorbent polymer is different" means that the liquid permeation rate under pressure or the centrifugal retention amount is different. From the above viewpoint, as for the water-absorbent polymer 3 fixed on the surface of the first side (upper surface) of the long base portions 2, the liquid permeation rate under a pressure of 2.0 kPa is preferably 20 ml/minute or greater, more preferably 40 ml/minute or greater, and preferably 1000 ml/minute or less, more preferably 800 ml/minute or less, and more specifically, preferably from 20 to 1000 ml/minute, more preferably from 40 to 800 ml/minute. As for the water-absorbent polymer particles 3 fixed on the surface of the second side (lower surface) of the long base portions 2, the liquid permeation rate under a pressure of 2.0 kPa is preferably 0 ml/minute or greater, more preferably 10 ml/minute or greater, and preferably 400 ml/minute or less, more preferably 200 ml/minute or less, and more specifically, preferably from 0 to 400 ml/minute, more preferably from 10 to 200 ml/minute. The liquid permeation rate under pressure is found according to the following measurement method.

{Method for Measuring Liquid Permeation Rate Under Pressure}

The liquid permeation rate under pressure is measured by employing the measurement method and measurement device disclosed in JP 2003-235889 A. In a 100-ml glass beaker, 0.32±0.005 g of the water-absorbent polymer, which is the sample to be measured, is immersed in a sufficient amount of physiological saline solution (0.9 mass % sodium chloride aqueous solution) sufficient for swelling the water-absorbent polymer—e.g., a physiological saline solution in an amount equal to or more than 5 times the saturation absorption amount of the water-absorbent polymer—and the sample is left for 30 minutes. Provided separately is a filter cylindrical tube in which a metal mesh (mesh opening: 150 μm; bio-column sintered stainless steel filter 30SUS sold by Sansyo Co., Ltd.) and a fine tube (inner diameter: 4 mm; length: 8 cm) with a valve (inner diameter: 2 mm) are provided to the lower end of an opening in a vertically-arranged cylinder (inner diameter: 25.4 mm). In a state where the valve is closed, the whole content of the aforementioned beaker, including the swollen measurement sample, is poured into the cylindrical tube. Then, a 2-mm-dia. circular cylindrical rod having, at its tip end, a metal mesh with a mesh opening of 150 μm and a diameter of 25 mm is inserted into the filter cylindrical tube so that the metal mesh comes into contact with the measurement sample, and further, a weight is placed on the measurement sample such that a load of 2.0 kPa is applied thereto. The sample is left in this state for 1 minute, the valve is opened to let the liquid pass through, and the time (T1) (seconds) from when the liquid level inside the filter cylindrical rube is at the 60 ml scale line to when the liquid level reaches the 40 ml scale line (i.e., the time required for 20 nil of liquid to pass through) is measured. By using the measured time T1 (seconds), the liquid permeation rate under a pressure of 2.0 kPa is calculated from the equation below. In the equation, T0 (seconds) is a measurement value of the time required for 20 nil of physiological saline solution to pass through the metal mesh when no measurement sample is placed inside the filter cylindrical tube.

$$\text{Liquid permeation rate under pressure (ml/min)} = 20 \times 60/(T1-T0)$$

The measurement is performed five times (n=5), the highest and lowest values are eliminated, and the average value of the remaining three samples is found as the measurement value. The measurement is performed at 23±2° C. at a humidity of 50±5%, and the sample is stored in this environment for 24 hours or longer before measurement. The method for measuring the liquid permeation rate under pressure is described in further detail in paragraphs {0008} and {0009} of JP 2003-235889 A, and the measurement device is illustrated in FIGS. 1 and 2 of the same publication.

From the aforementioned viewpoint, as for the water-absorbent polymer 3 fixed on the surface of the first side (upper surface) of the long base portions 2, the centrifugal retention amount (water absorption amount) is preferably 20 g/g or greater, more preferably 25 g/g or greater, and preferably 50 g/g or less, more preferably 45 g/g or less, and more specifically, preferably from 20 to 50 g/g, more preferably from 25 to 45 g/g. As for the water-absorbent polymer 3 fixed on the surface of the second side (lower surface) of the long base portions 2, the centrifugal retention amount (water absorption amount) is preferably 25 g/g or greater, more preferably 30 g/g or greater, and preferably 65 g/g or less, more preferably 55 g/g or less, and more specifically, preferably from 25 to 65 g/g, more preferably from 30 to 55 g/g. The centrifugal retention amount (water absorption amount) is found according to the following measurement method.

{Method for Measuring Centrifugal Retention Amount (Water Absorption Amount)}

The centrifugal retention amount (water absorption amount) is measured in compliance with JIS K 7223 (1996). A nylon woven fabric (sold by Sanriki Seisakusho; product name: nylon mesh; specification: 250 mesh) is cut into a rectangle that is 10 cm wide and 40 cm long, the rectangle is folded into two at the longitudinal center, and both ends are heat-sealed, to prepare a nylon bag that is 10 cm wide (inner dimension: 9 cm) and 20 cm long. Next, 1.00 g of the water-absorbent polymer, which is the sample to be measured, is weighed precisely, and is placed uniformly at the bottom of the prepared nylon bag. Then, the nylon bag containing the sample is immersed in a physiological saline solution (0.9 mass % sodium chloride aqueous solution) whose temperature has been adjusted to 25° C. After 1 hour from the start of immersion, the nylon bag is removed from the physiological saline solution, is hung in a vertical state for 1 hour to drain, and is then dehydrated by using a centrifugal drier (product of Kokusan Co., Ltd.; model: H-130C special). The dehydration is performed at 143 G (800 rpm) for 10 minutes. After dehydration, the mass of the sample is measured, and the centrifugal retention amount (water absorption amount) to be found is calculated according to the equation below.

$$\text{Centrifugal retention amount (g/g)} = (a'-b-c)/c$$

In the equation, a' is the total mass (g) of the centrifugally-dehydrated sample and the nylon bag, b is the mass (g) of the nylon bag before water absorption (when dry), and c is the mass (g) of the sample before water absorption (when dry).

The measurement is performed five times (n=5); the highest and lowest values are eliminated, and the average value of the remaining three samples is found as the measurement value. The measurement is performed at 23±2° C. at a humidity of 50±5%, and the sample is stored in this environment for 24 hours or longer before measurement.

In the sheet-like article 1, in a state after swelling as illustrated in FIG. 19, the water-absorbent polymer particles 3 swell beyond the long base portion 2's lateral side edge portions 2s that extend along the longitudinal direction (y1 direction). Herein, "the water-absorbent polymer particles 3 swell beyond the long base portion 2's lateral side edge portions 2s" means, in other words, that, in a state after swelling of the sheet-like article 1, the swollen water-absorbent polymer particles 3 extend across the lateral side edge portions 2s of the long base portions 2, like the swollen water-absorbent polymer particle 3a as illustrated in FIG. 19, for example. Note that, so long as the swollen water-absorbent polymer particles 3 extend across the lateral side edge portions 2s of the long base portions 2 in a state after swelling of the sheet-like article 1, the water-absorbent polymer particles 3 may exist inward of the lateral side edge portions 2s of the long base portions 2 in a state before use of the sheet-like article 1. Alternatively, the water-absorbent polymer particles 3 may extend across the lateral side edge portions 2s of the long base portions 2 from the beginning, like the water-absorbent polymer particle 3b before use (before swelling) as illustrated in FIG. 18, for example.

Further, in the sheet-like article 1, in a swollen state as illustrated in FIG. 19, the position, in the thickness direction (z1 direction), of the water-absorbent polymer particles 3 in each long base portion 2 is varied, for example vertically and/or obliquely, from the position thereof before absorbing a liquid. Herein, "in a state after swelling of the sheet-like article 1, the position, in the thickness direction (z1 direction), of each long base portion 2 is varied from the position thereof before absorbing a liquid" means that the sheet-like article is formed such that the position of each long base portion 2 in a state after swelling of the water-absorbent polymer particles 3 is varied from the position of the long base portion 2 in a state before use (before swelling) of the water-absorbent polymer particles 3.

In the diaper 10, from the viewpoint of maintaining fittability in the side regions ST after urination, it is preferable that, on the surfaces of both faces (upper surface and lower surface) of each long base portion 2, the basis weight of the water-absorbent polymer 3 of the absorbent units 4 arranged in the central region CT of the sheet-like article 1, which is the absorbent core 24, is greater than the basis weight of the water-absorbent polymer 3 of the absorbent units 4 arranged in each side region ST of the sheet-like article 1, which is the absorbent core 24. From the aforementioned viewpoint, the basis weight of the water-absorbent polymer 3 of the absorbent units 4 arranged in the central region CT is preferably from 30 to 400 g/m$^2$, more preferably from 50 to 300 g/m$^2$, per each face. From the aforementioned viewpoint, the basis weight of the water-absorbent polymer 3 of the absorbent units 4 arranged in each side region ST is preferably from 10 to 250 g/m$^2$, more preferably from 30 to 150 g/m$^2$, per each face.

Figure 20:
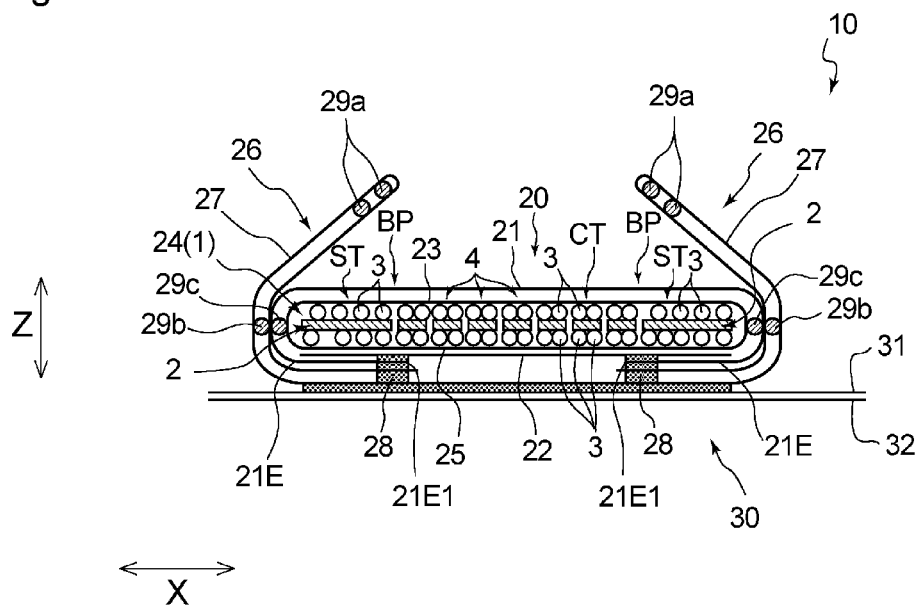
FIG. 20 is a cross-sectional view taken along line VI-VI illustrated in FIG. 16.

As illustrated in FIG. 20, in the absorbent assembly 20 of the diaper 10, the topsheet 21 covers the entire surface of the skin-facing surface of the absorbent member 23 including the absorbent core 24, and includes extension portions 21E extending outward, in the article lateral direction X, from respective lateral side edge portions of the absorbent member 23, the extension portions 21E being folded back toward the non-skin-facing surface side of the absorbent member 23 and respectively covering the absorbent member 23's non-skin-facing surface located in the respective side regions ST of the absorbent core 24. Preferably, the absorbent assembly 20 includes the topsheet 21, which covers the skin-facing surface of the absorbent core 24, and the backsheet 22, which covers the non-skin-facing surface of the absorbent core 24. The topsheet 21 is made of a liquid-permeable sheet, and is a sheet that faces the wearer's skin when the diaper 10 is worn. The topsheet 21 covers the entire region, in the article longitudinal direction Y, of the sheet-like article 1 which is the absorbent core 24, and the tip-end portion 21E1 of each extension portion 21E of the topsheet 21 extends beyond the respective side region ST of the sheet-like article 1, which is the absorbent core 24, and reaches the non-skin-facing surface of the absorbent member 23 located in the central region CT. The backsheet 22 covers the entire region, in the article longitudinal direction Y, of the sheet-like article 1 which is the absorbent core 24, and also covers the entire region in the article lateral direction X. The backsheet 22 is made of a liquid-impermeable or water-repellent sheet, and is a sheet that faces the outer cover 30.

In the diaper 10, as illustrated in FIG. 20, the tip-end portion 21E1 of each extension portion 21E of the topsheet 21 is located more toward the non-skin-facing surface side than the extension portion 21E, and is fixed to a constituent member of the absorbent article located adjacent to the extension portion 21E. Preferably, in the diaper 10, the absorbent assembly 20 includes a pair of leak-proof cuffs 26, 26 in the respective lateral sides along the article longitudinal direction Y. Each leak-proof cuff 26 is made by folding, into two, a water-repellent sheet material 27 having a rectangular shape that is long in the article longitudinal direction Y, and interposing and fixing a lateral side region of the folded sheet material 27 between the backsheet 22 and the extension portion 21E of the topsheet 21. Stated differently, in the diaper 10, the sheet material 27 forming the leak-proof cuff 26 serves as the absorbent article's constituent member on the non-skin-facing surface side to which the tip-end portion 21E1 of the topsheet 21 is fixed. This joining forms a joined region 28 extending along the article longitudinal direction Y.

In the diaper 10, the joined region 28 is formed by joining the sheet material 27 forming the leak-proof cuff 26, the tip-end portion 21E1 of the extension portion 21E of the topsheet 21, and the backsheet 22 together by using a known joining means such as heat sealing, high-frequency sealing, ultrasonic sealing, or a hot-melt adhesive. The joined region 28 may be formed as a continuous straight line, but is not limited thereto, and may be formed as an intermittent straight line having non-continuous portions in places, or may be formed as a continuous or intermittent curved line.

In the diaper 10, as illustrated in FIG. 20, the position where the tip-end portion 21E1 of the topsheet 21 is fixed to the sheet material 27 forming the leak-proof cuff 26—i.e., the position of the joined region 28—matches a position BP corresponding to a boundary between the central region CT and the side region ST of the sheet-like article 1 which is the absorbent core 24. Preferably, in the diaper 10, in a cross-sectional view as illustrated in FIG. 20, the position of the joined region 28 and the position BP corresponding to the boundary overlap one another in the article thickness direction Z.

As illustrated in FIG. 20, in the diaper 10, the sheet material 27, in a state folded into two, has its fold line located on the inner side in the article lateral direction X, and thread-form elastic members 29a are fixed in their stretched state inside the position of the fold line. The contraction of the elastic members 29a causes the leak-proof cuff 26 to stand up toward the wearer's skin side when the diaper 10 is worn.

Further, as illustrated in FIG. 20, in the diaper 10, in addition to the thread-form elastic, members 29a, a thread-form elastic member 29h is fixed in its stretched state inside the sheet material 27 folded into two and forming the leak-proof cuff 26. The elastic member 29b is arranged between the joined region 28 and the thread-form elastic members 29a in the leak-proof cuff 26, and is arranged over the entire article longitudinal direction Y of the leak-proof cuff 26. The thread-form elastic member 29b is arranged at a position outward, in the article lateral direction X, of a later-described thread-form elastic member 29c arranged at a lateral side of the absorbent member 23 in a spread-out state of the diaper 10.

Further, as illustrated in FIG. 20, in the diaper 10, an elastic member 29c is provided to each of the absorbent member 23's lateral side edge portions, which extend along the article longitudinal direction Y, and is arranged in its stretched state along the lateral side edge portion. The elastic member 29c is arranged over the entire length, in the article longitudinal direction Y, of the sheet-like article 1 which is the absorbent core 24. The elastic member 29c is located between the core-wrap sheet 25 constituting the absorbent member 23 and the topsheet 21 and is joined to both sheets. The contractile force of the elastic member 29c causes the absorbent member 23 located in each side region ST of the absorbent core 24 to stand up toward the wearer's skin side.

The constituent materials in the various sections of the aforementioned disposable diaper 10 are described below.

For the constituent materials in the various sections, materials ordinarily used in this technical field can be used without particular limitation.

For example, for the topsheet 21, it is possible to use a hydrophilic liquid-permeable nonwoven fabric or a porous film. For the backsheet 22, it is possible to use a liquid-impermeable material or water-repellent material. For the liquid-impermeable material, it is possible to use, for example, a resin film or a laminate of a resin film and nonwoven fabric. For the water-repellent material, a water-repellent nonwoven fabric can be used, for example. For the water-repellent nonwoven fabric, it is possible to use a later-described nonwoven fabric used for the sheet material 27 forming the leak-proof cuff 26. For the core-wrap sheet 25, it is possible to use, for example, tracing paper (tissue paper) made by a wet papermaking method or a liquid-permeable nonwoven fabric.

For the sheet material 27 forming the leak-proof cuff 26, it is possible to use, for example, a multilayer-structure composite nonwoven fabric including spun-bonded/melt-blown/spun-bonded layers, a spun-bonded nonwoven fabric, a heat-bonded nonwoven fabric, or an air-through nonwoven fabric. From the viewpoint of softness and water resistance, a multilayer-structure nonwoven fabric made of spun-bonded and melt-blown layers is preferable.

The inner sheet 31 and outer sheet 32 forming the outer cover 30 are preferably made of the same or different air-permeable sheets, such as nonwoven fabrics manufactured according to one of various methods. For example, spun-bonded nonwoven fabrics are preferably used for the inner sheet 31 and outer sheet 32.

The thread-form elastic members 29a, 29b, 29c used in the absorbent assembly 20 may be shaped preferably as rubber threads or rubber bands with a predetermined width (such as rubber tapes), and particularly preferably as rubber threads. Similarly, the thread-form elastic members 33 (waist elastic members 33W, leg elastic members 33L, and below-waist elastic members 33D) used in the outer cover 30 may be shaped preferably as rubber threads or rubber bands with a predetermined width (such as rubber tapes), and particularly preferably as rubber threads. Examples of materials for the elastic members 29a, 29b, 29c and the elastic members 33 (waist elastic members 33W, leg elastic members 33L, and below-waist elastic members 33D) include natural rubber, synthetic rubber such as styrene-butadiene, butadiene, isoprene and neoprene, EVA, extensible polyolefins, and urethane.

The following describes the effects of using the aforementioned diaper 10 of the present embodiment of the invention.

As illustrated in FIGS. 15 and 16, in the diaper 10, the absorbent core 24 of the absorbent member 23 is formed of a sheet-like article 1 including a plurality of absorbent units 4 provided with a water-absorbent polymer 3. Further, as illustrated in FIG. 17, in each side region ST of the sheet-like article 1 which is the absorbent core 24, the absorbent units 4 are arranged such that their longitudinal direction (y1 direction) is oriented in the article lateral direction X. Further, as illustrated in FIG. 20, the topsheet 21 covers the entire surface of the skin-facing surface of the absorbent member 23, and includes extension portions 21E extending outward, in the article lateral direction X, from respective lateral side edge portions of the absorbent member 23, wherein: the extension portions 21E are folded back toward the non-skin-facing surface side of the absorbent member 23 and respectively cover the absorbent member 23's non-skin-facing surface located in the respective side regions ST of the absorbent core 24; and the tip-end portion 21E1 of each extension portion 21E is fixed to a constituent member of the absorbent article located adjacent to the extension portion at the joined region 28. Since the absorbent units 4 are arranged such that their longitudinal direction (y1 direction) is oriented in the article lateral direction X and the topsheet 21 is arranged so as to envelop the side regions ST of the sheet-like article 1 in which the absorbent units 4 are arranged, the side sections of the absorbent member 23 that correspond to the respective side regions ST easily stand up when the diaper is worn as illustrated in FIG. 21, thus improving fittability and leakage-preventing performance of the crotch portion C and suppressing uncomfortableness to the wearer while the diaper is worn.

Figure 21:
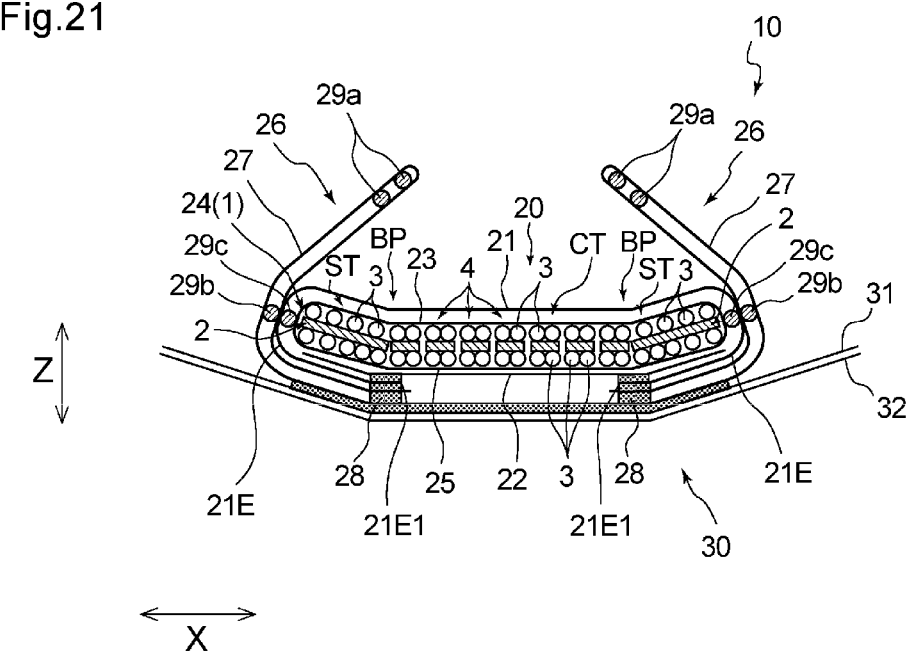
FIG. 21 is a cross-sectional view of the diaper illustrated in FIG. 20 in a state where the diaper is worn.

Further, in the diaper 10, as illustrated in FIG. 21, the thread-form elastic members 29a are fixed in their stretched state at the position of the bifold line of each sheet material 27 forming the leak-proof cuff 26. Thus, the contraction of the elastic members 29a causes the leak-proof cuffs 26 to stand up, thus further facilitating the absorbent member in the side sections of the absorbent member 23 to stand up. Furthermore, in the diaper 10, as illustrated in FIG. 21, the elastic member 29c is provided in its stretched state to each of the absorbent member 23's lateral side edge portions. Thus, the contractile force of the elastic member 29c causes the absorbent member 23 located in each side region ST of the absorbent core 24 to further stand up toward the wearer's skin side. Further, in the diaper 10, as illustrated in FIG. 21, the thread-form elastic member 29b is arranged in a position outward, in the article lateral direction X, of the elastic member 29c. Thus, the absorbent member 23 located in each side region ST is further facilitated to stand up.

Further, in the diaper 10, as illustrated in FIG. 20, the position (the joined region 28) where the tip-end portion 21E1 of the topsheet 21 is fixed to the sheet material 27 forming the leak-proof cuff 26 matches the position BP corresponding to the boundary between the central region CT and the side region ST of the sheet-like article 1 which is the absorbent core 24. Thus, the absorbent member in each side section of the absorbent member 23 is further facilitated to stand up.

Further, in the diaper 10, as illustrated in 17, in the central region CT of the sheet-like article 1 which is the absorbent core 24, the absorbent units 4 are arranged such that their longitudinal direction (y1 direction) is oriented in the article longitudinal direction Y. Thus, while the diaper 10 is worn, the section in the absorbent assembly 20 corresponding to the central region CT can easily fit against the wearer's crotch width. Further, body fluid easily diffuses in the article longitudinal direction Y in the central region CT of the sheet-like article 1, and thus, the entire sheet-like article 1 can be employed advantageously, thereby improving absorption performance.

Further, as illustrated in FIG. 19, in the sheet-like article 1 which is the absorbent core 24 in the diaper 10, in a state after swelling, the water-absorbent polymer particles 3 swell beyond the long base portion 2's lateral side edge portions 2s (cf. the water-absorbent polymer particle 3a in FIG. 19), and the positions, in the thickness direction (Z direction; z1 direction), of the water-absorbent polymer particles 3 in each long base portion 2 are varied from the positions thereof before absorbing a liquid. Thus, even when the water-absorbent polymer particles 3, 3 that have swollen beyond the lateral side edge portions 2s of the respective long base portions 2 of adjacent absorbent units 4, 4 come into contact with one another when the water-absorbent polymer particles 3 absorb body fluid and swell as illustrated in FIG. 19, the adjacent absorbent units 4, 4 are facilitated to move freely in the thickness direction (Z direction; z1 direction), which makes it possible to lessen collision between the swollen water-absorbent polymer particles 3, 3 and reduce pressure applied to the swollen water-absorbent polymer particles 3, thus suppressing inhibition of absorption of body fluid by the water-absorbent polymer particles 3. Thus, in the sheet-like article 1 which is the absorbent core 24, the water-absorbent polymer particles 3 are less likely to cause swelling inhibition when the water-absorbent polymer particles 3 absorb body fluid and swell, and it is possible to make full use of the absorption performance of the water-absorbent polymer particles 3. Thus, the absorption performance of the diaper 10 is easily improved. Particularly, in the sheet-like article 1 of the diaper 10, since there is no intervening member present between the absorbent units 4, 4 adjacent to one another, the absorbent units 4 can move easily, thus making it even more easy to achieve the aforementioned effects.

Further, in the sheet-like article 1 of the diaper 10, in a state after swelling as illustrated in FIG. 19, the respective positions of the long base portions 2 constituting adjacent absorbent units 4 are varied in the thickness direction (Z direction; z1 direction). Thus, the adjacent absorbent units 4, 4 are facilitated to move freely in the thickness direction (Z direction; z1 direction), which makes it possible to easily lessen collision between the swollen water-absorbent polymer particles 3, 3 and reduce pressure applied to the swollen water-absorbent polymer particles 3, thus suppressing inhibition of absorption of body fluid by the water-absorbent polymer particles 3.

In the sheet-like article 1 of the diaper 10, from the viewpoint of further suppressing swelling inhibition of the water-absorbent polymer particles 3 by causing the water-absorbent polymer particles 3 in a swollen state to swell beyond the lateral side edge portions 2s of the long base portions 2 and cause adjacent absorbent units 4, 4 to move freely in the thickness direction (Z direction; z1 direction), it is preferable that, in a state before use as illustrated in FIG. 18, the water-absorbent polymer particles 3 are arranged in the vicinity of the long base portion 2's lateral side edge portions 2s which extend along the longitudinal direction (y1 direction), and more preferably, the water-absorbent polymer particles 3 protrude beyond the long base portion 2's lateral side edge portions 2s (cf. the water-absorbent polymer particle 3b illustrated in FIG. 18).

Particularly, in the central region CT of the sheet-like article 1, from the viewpoint of further suppressing swelling inhibition of the water-absorbent polymer particles 3 by causing the water-absorbent polymer particles 3 in a swollen state to swell beyond the lateral side edge portions 2s of the long base portions 2 and cause adjacent absorbent units 4, 4 to move freely in the thickness direction (Z direction; z1 direction), it is preferable that the distance between the long base portion 2's both lateral side edge portions 2s, 2s that extend along the longitudinal direction (y1 direction) is greater than the average particle size of the water-absorbent polymer particles 3 in a state before use (before swelling), and is smaller than the average particle size of the water-absorbent polymer particles 3 in a state after swelling. Herein, "the distance between the long base portion 2's both lateral side edge portions 2s, 2s" is synonymous with the width (W2C) of the long base portion 2. It is preferable that the average particle size of the water-absorbent polymer particles 3 in a state before use (before swelling) is preferably 20 μm or greater, more preferably 200 μm or greater, and preferably 700 μm or less, more preferably 500 μm or less, and more specifically, preferably from 20 to 700 μm, more preferably from 200 to 500 μm. On the other hand, the average particle size of the water-absorbent polymer 3 in a state after swelling is preferably 200 μm or greater, more preferably 800 μm or greater, and preferably 3000 μm or less, more preferably 2000 μm or less, and more specifically, preferably from 200 to 3000 μm, more preferably from 800 to 2000 μm. The average particle size of the water-absorbent polymer particles 3 is found according to the following measurement method.

{Method for Measuring Average Particle Size d1 of Water-Absorbent Polymer Particles in a State Before Use}

The average particle size d1 in a state before use was measured using water-absorbent polymer particles before use by observing the diameter or major axis of the water-absorbent polymer particles with an optical microscope. Herein, "diameter" applies to cases where the water-absorbent polymer particle is spherical, and "major axis" applies to cases where the water-absorbent polymer particle is odd-formed, such as rhombic, rectangular, cluster-like, or football-shaped. The diameter or major axis is measured for a total of 50 water-absorbent polymer particles, and the number-average particle size is defined as the average particle size d1 of the water-absorbent polymer particles in a state before use.

{Method for Measuring Average Particle Size d2 of Water-Absorbent Polymer Particles in a State after Swelling}

The average particle size d2 in a state after swelling was measured by: immersing the sheet-like article 1 in a physiological saline solution (0.9 mass % sodium chloride aqueous solution) whose temperature has been adjusted to 25° C.; taking the sheet-like article 1 out from the physiological saline solution after 1 hour from the start of immersion; draining the sheet-like article by hanging the same in a vertical state for 30 minutes; and then observing, with an optical microscope, the diameter or major axis of the water-absorbent polymer particles on the surface of the long base portions 2. Herein, "diameter" applies to cases where the water-absorbent polymer particle is spherical, and "major axis" applies to cases where the water-absorbent polymer particle is odd-formed, such as rhombic, rectangular, cluster-like, or football-shaped. The diameter or major axis is measured for a total of 50 water-absorbent polymer particles, and the number-average particle size can be defined as the average particle size of the water-absorbent polymer particles in a state after swelling.

Figure 22:
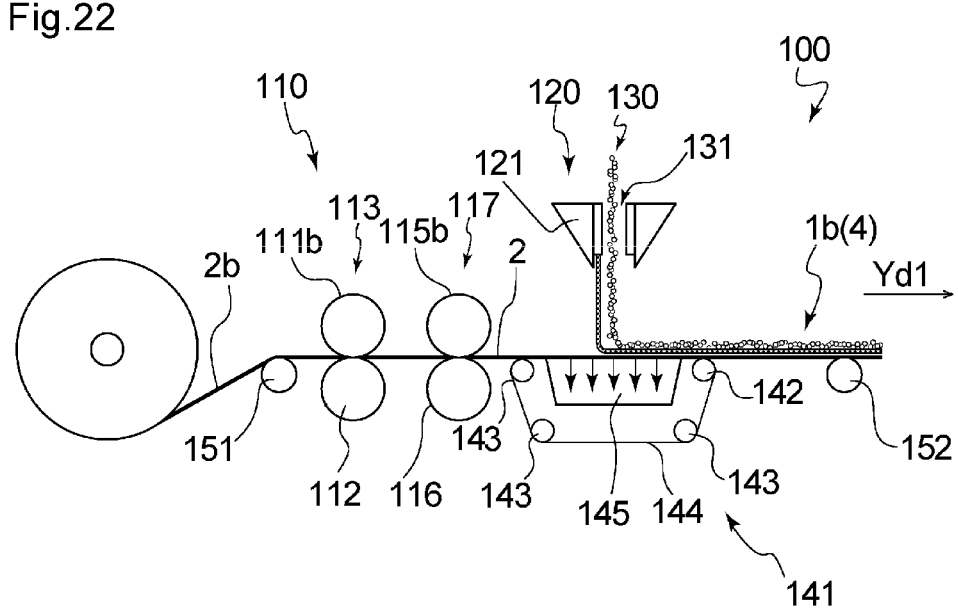
FIG. 22 is a schematic diagram illustrating an embodiment of a device for manufacturing a sheet-like article, which is an absorbent core of the diaper illustrated in FIG. 15.

Next, a preferred embodiment of a method for manufacturing a sheet-like article used in a disposable diaper 10, which is an embodiment of the invention, is described with reference to FIG. 22 according to an example of manufacturing the sheet-like article 1 configured as above. FIG. 22 illustrates a manufacturing device 100 suitably used for the manufacturing method of the present embodiment. The manufacturing device 100 of the present embodiment includes, in the following order from the upstream side toward the downstream side of the manufacturing steps: a base sheet cutting unit 110; an adhesive application unit 120; and a water-absorbent polymer dispersion unit 130. Note that, although the manufacturing device 100 illustrated in FIG. 22 uses a device in which the adhesive application unit 120 and the water-absorbent polymer dispersion unit 130 are integrated, the adhesive application unit 120 and the water-absorbent polymer dispersion unit 130 do not have to be integrated. In the integrated device, the adhesive application unit 120 is arranged on the upstream side of the device, and the water-absorbent polymer dispersion unit 130 is arranged on the downstream side of the integrated device.

The base sheet cutting unit 110 is a region for forming a plurality of long base portions 2 by cutting a continuous base sheet 2b, which is the material for the long base portions 2. Any one of various known cutting devices can be used without particular limitation for cutting the base sheet 2b. As illustrated in FIG. 22, this manufacturing device 100 employs: a set of a cutting device 113, as illustrated in FIG. 23, including a rotary die 111b having a plurality of cutter blades 111a, 111a, 111a, ... arranged on the circumferential surface thereof, and a receiving roller 112 that has a flat circumferential surface and that is arranged in opposition to the rotary die 111b; and a set of a cutting device 117, as illustrated in FIG. 24, including a rotary die 115b having a plurality of cutter blades 115a, 115a, 115a, ... arranged on the circumferential surface thereof, and a receiving roller 116 that has a flat circumferential surface and that is arranged in opposition to the rotary die 115b.

Figure 23:
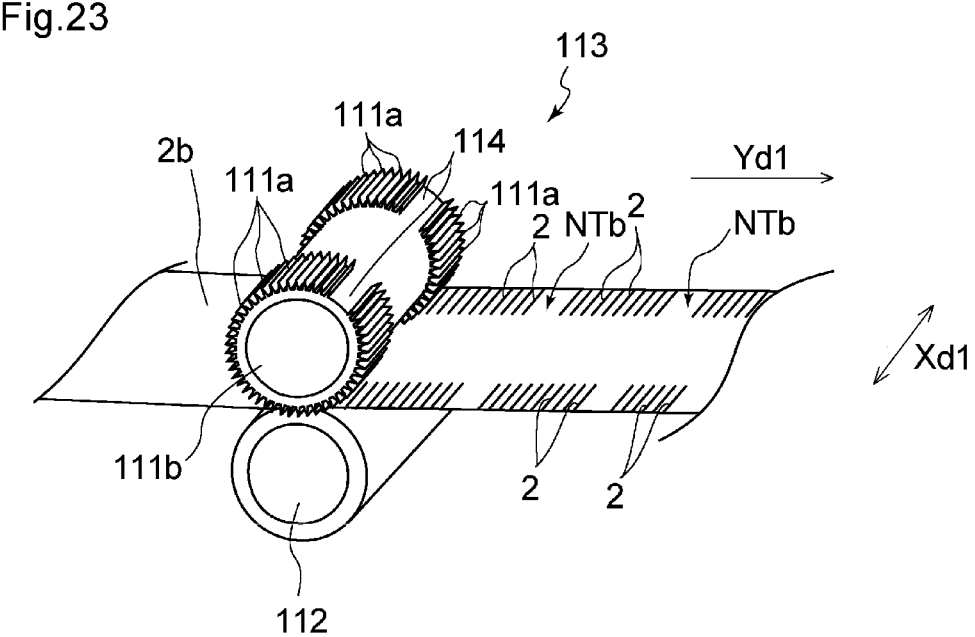
FIG. 23 is a schematic perspective view of an upstream-side base sheet cutting unit provided in the manufacturing device illustrated in FIG. 22.

As illustrated in FIG. 23, the upstream-side cutting device 113 includes a plurality of cutter blades 111a, 111a, 111a, ... arranged in each of the respective end portions in the roller's axial direction so as to correspond to the respective lateral sides extending along the transporting direction (Yd1 direction) of the base sheet 2b. The cutter blades 111a, 111a, 111a, ... are arranged with intervals therebetween in the roller's circumferential direction, and the direction of each blade is arranged in a direction (Xd1 direction) orthogonal to the transporting direction (Yd1 direction) of the continuous base sheet 2b. The distance between the cutter blades 111a, 111a adjacent to one another in the roller's circumferential direction corresponds to the width W2S (cf. FIG. 17) of each long base portion 2 to be formed in each side region ST. Herein, the transporting direction (Yd1 direction) of the base sheet 2b corresponds to the article longitudinal direction Y of the sheet-like article 1 to be manufactured, and the orthogonal direction (Xd1 direction) corresponds to the article lateral direction X of the sheet-like article 1 to be manufactured. Note that, for cutting the base sheet 2b, it is possible to use a laser device that performs melting-and-cutting by the irradiation of a laser beam.

As in the sheet-like article 1 illustrated in FIG. 17, in cases where the sheet-like article 1 includes respective non-slit regions NT2 at both end portions in the article lateral direction X, a non-arrangement section 114 where no cutter blade 111a is arranged may be formed on the circumferential surface of the roller, as illustrated in FIG. 23 for example. The length of the arc of the non-arrangement section 114 on the circumferential surface of the roller having the rotating cutter blades 111a corresponds to a length equal to the total length, in the article longitudinal direction Y, of the non-slit regions NT1 arranged at both end portions, in the article longitudinal direction Y, of the sheet-like article 1 illustrated in FIG. 17. Note that the length of the cutter blade 111a in the roller's axial direction corresponds to the length L2S (cf. FIG. 17), in the longitudinal direction (y1 direction), of each long base portion 2 in each side region ST of the sheet-like article 1 illustrated in FIG. 17. Further, in cases where the sheet-like article 1 includes non-slit regions NT2 in both lateral sides extending along the article longitudinal direction Y, it is possible to use cutter blades 111a whose length in the roller's axial direction does not extend up to the respective positions corresponding to the non-slit regions NT2.

Figure 24:
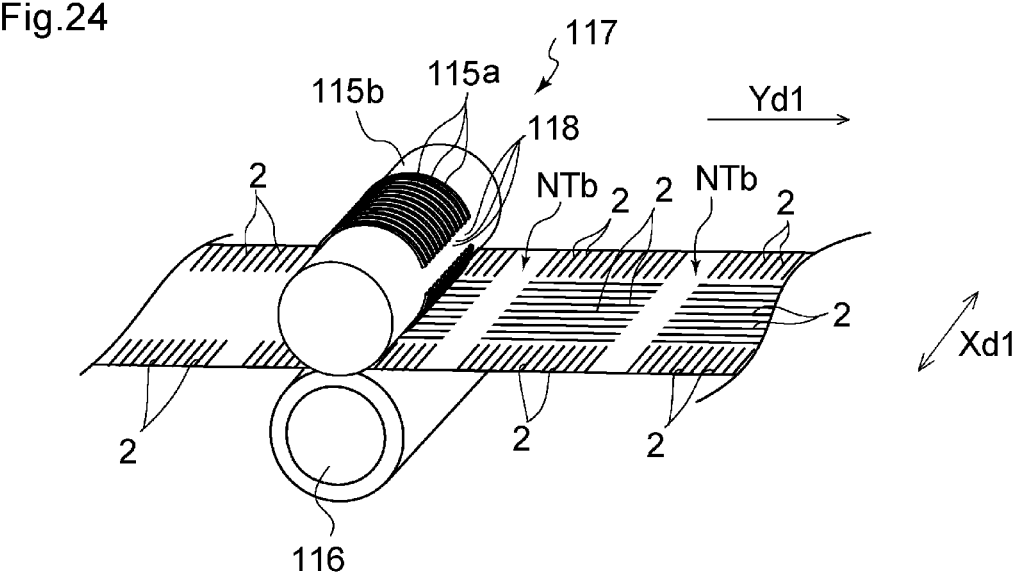
FIG. 24 is a schematic perspective view of a downstream-side base sheet cutting unit provided in the manufacturing device illustrated in FIG. 22.

The downstream-side cutting device 117 is a cutting device 117 including: a plurality of cutter blades 115a, 115a, 115a, ... corresponding to the central region in the direction (Xd1 direction) orthogonal to the transporting direction (Yd1 direction) of the continuous base sheet 2b as illustrated in FIG. 24; and a receiving roller 116 that is arranged in opposition common to the cutter blades 115a, 115a, 115a, ... and that has a flat circumferential surface. The cutter blades 115a, 115a, 115a, ... of the cutting device 117 are arranged side by side in the orthogonal direction (Xd1 direction). The distance between the cutter blades 115a, 115a adjacent to one another in the orthogonal direction (Xd1 direction) corresponds to the width W2C (cf. FIG. 17) of each long base portion 2 to be formed in the central region CT. Note that, for cutting the base sheet 2b, it is possible to use: a cutting device employing a shear-cut method in which cutting is achieved by rubbing the side surfaces of an upper blade and a lower blade against one another; or a laser device that performs melting-and-cutting by the irradiation of a laser beam.

As in the sheet-like article 1 illustrated in FIG. 17, in cases where the sheet-like article 1 includes respective non-slit regions NT1 at both end portions in the article longitudinal direction Y, a non-arrangement section 118 where no cutter blade 115a is arranged may be formed on the circumferential surface of the roller, as illustrated in FIG. 24 for example. The length of the arc of the non-arrangement section 118 on the outer circumference of the rotating cutter blades 115a corresponds to a length equal to the total length, in the article longitudinal direction Y, of the non-slit regions NT1 of the sheet-like article 1 illustrated in FIG. 17. It is possible to prepare a plurality of cutter blades 115a, 115a, 115a, ... each having such a non-arrangement section 118, and to align the positions of the respective non-arrangement sections 118, 118 of the cutter blades 115a adjacent to one another in the Xd1 direction. Note that the length of the arc in a section excluding the non-arrangement section 118 in the outer circumference of each rotating cutter blade 115a corresponds to the length L2C (cf. FIG. 17), in the longitudinal direction (y1 direction), of each long base portion 2 in the central region CT of the sheet-like article 1 illustrated in FIG. 17.

The adhesive application unit 120, which is located downstream of the base sheet cutting unit 110, is a region for applying an adhesive 5 on the surface of first side (upper surface) of the respective long base portions 2. As illustrated in FIG. 22, the manufacturing device 100 includes an application head 121. Any one of various known application devices can be used without particular limitation for the application head 121. In the Xd1 direction, the application head 121 is formed having a length corresponding to the width (length in the article lateral direction X) of the absorbent region AT of the sheet-like article 1. The application head 121 configured as above is arranged above first side (upper surface) of the long base portions 2 at a distance therefrom.

The water-absorbent polymer dispersion unit 130, which is located downstream of the adhesive application unit 120, is a region for dispersing water-absorbent polymer particles 3 on the surface of the first side (upper surface) of the long base portions 2, to thereby form absorbent units 4. As illustrated in FIG. 22, the manufacturing device 100 includes a water-absorbent polymer introduction unit 131. For the water-absorbent polymer introduction unit 131, any one of various known introduction devices can be used without particular limitation. In the Xd1 direction, the water-absorbent polymer introduction unit 131 is formed having a length corresponding to the width (length in the article lateral direction X) of the absorbent region AT of the sheet-like article 1. The water-absorbent polymer introduction unit 131 configured as above is arranged above the first side (upper surface) of the long base portions 2 at a distance therefrom.

In the manufacturing device 100 illustrated in FIG. 22, a vacuum conveyor 141 is arranged at a position opposing the device in which the adhesive application unit 120 and the water-absorbent polymer dispersion unit 130 are integrated, and on the lower surface side of the plurality of long base portions 2 being transported. The vacuum conveyor 141 includes an endless air-permeable belt 144 that bridges a drive roller 142 and a plurality of driven rollers 143; and a vacuum box 145 arranged at a position opposing the aforementioned integrated device across the air-permeable belt 144. The plurality of long base portions 2, which have been formed by cutting the base sheet 2b with the base sheet cutting unit 110, are introduced onto the vacuum conveyor 141.

The manufacturing device 100 illustrated in FIG. 22 includes: a drive roller 151 that pays out the base sheet 2b from an original textile roll of the continuous base sheet 2b; and a drive roller 152, at the most downstream side, that transports a precursor 1b of a sheet-like article 1 which has been manufactured.

Next, a method for manufacturing sheet-like articles 1 continuously using the aforementioned manufacturing device 100 of the present embodiment, i.e., an embodiment of a method for manufacturing a sheet-like article 1 used in a disposable diaper 10 which is an embodiment of the invention, will be described.

The method for manufacturing a sheet-like article 1 employing the manufacturing device 100 involves: a cutting step of cutting a continuous base sheet 2b to thereby form a plurality of the long base portions 2; and a water-absorbent polymer particle dispersion step of dispersing water-absorbent polymer particles 3 after the cutting step. In the present embodiment, an adhesive application step of applying an adhesive 5 is provided before the water-absorbent polymer particle dispersion step. More specifically, the method for manufacturing a sheet-like article 1 employing the manufacturing device 100 includes the adhesive application step after the cutting step, and the water-absorbent polymer particle dispersion step after the adhesive application step.

First, before executing the cutting step, negative pressure is generated inside the vacuum box 145 by activating an evacuation device connected thereto.

Next, the drive rollers 151 and 152 are driven, the cutting device 113 and the air-permeable belt 144 are rotated, and the vacuum conveyor 141 is activated. Then, the base sheet 2b is paid out by the drive roller 151 from the original textile roll of the continuous base sheet 2b, and the base sheet 2b is supplied between the receiving roller 112 and the roller including the plurality of cutter blades 111a, and also between the receiving roller 116 and the cutter blades 115a, in the cutting device 113 of the base sheet cutting unit 110, to cut the continuous base sheet 2b and form a plurality of long base portions 2 (cutting step). In the method for manufacturing a sheet-like article 1 employing the manufacturing device 100, the continuous base sheet 2b is first cut by being supplied between the receiving roller 112 and the roller including the plurality of cutter blades 111a, and is then cut by being supplied between the receiving roller 116 and the cutter blades 115a, to thereby be formed into the plurality of long base portions 2. However, the long base portions 2 may be formed by supplying and cutting the base sheet between the receiving roller 116 and the cutter blades 115a, and then supplying and cutting the base sheet between the receiving roller 112 and the roller including the plurality of cutter blades 111a.

In the embodiment using the cutting device 113 on the upstream side, as illustrated in FIG. 23, the plurality of cutter blades 111a, 111a, 111a, . . . are arranged in both end portions in the roller's axial direction, and the direction of each cutter blade 111a arranged in each end portion in the roller's axial direction is arranged along the direction (Xd1 direction) orthogonal to the transporting direction (Yd1 direction) of the continuous base sheet 2b. Thus, the continuous base sheet 2b is cut in both side regions which extend along the transporting direction (Yd1 direction) of the base sheet 2b, and a plurality of long base portions 2 are formed by cutting the base sheet at a plurality of sections in both side regions along the orthogonal direction (Xd1 direction) with intervals therebetween in the transporting direction (Yd1 direction). The sections cut by the cutter blades 111a become the lateral side edge portions 2s of the respective long base portions 2 arranged in the side regions ST.

In the present embodiment employing the manufacturing device 100, a non-arrangement section 114 where no cutter blade 111a is arranged is formed on the circumferential surface in both end portions in the roller's axial direction. Thus, a non-cut portion NTb corresponding to a length equal to the total length, in the article longitudinal direction Y, of the non-slit regions NT1 is formed intermittently in the continuous base sheet 2b being transported. The plurality of long base portions 2 formed in both side regions by the upstream-side cutting device 113 in the cutting step are formed parallel to the orthogonal direction (Xd1 direction) and are arranged side by side in the transporting direction (Yd1 direction).

Next, in the embodiment using the cutting device 117 on the downstream side, as illustrated in FIG. 24, the plurality of cutter blades 115a are arranged in the central region in the direction (Xd1 direction) orthogonal to the transporting direction (Yd1 direction) of the base sheet 2b, and each cutter blade 115a is arranged side by side in the orthogonal direction (Xd1 direction), Thus, the continuous base sheet 2b is cut in the central region, and a plurality of long base portions 2 are formed by cutting the base sheet at a plurality of sections in the central region along the transporting direction (Yd1 direction) with intervals therebetween in the orthogonal direction (Xd1 direction). The sections cut by the cutter blades 115a become the lateral side edge portions 2s of the respective long base portions 2 arranged in the central region CT.

In the present embodiment employing the manufacturing device 100, each cutter blade 115a has a non-arrangement section 118. By matching the positions of the respective non-arrangement sections 118 with the non-cut portion NTb formed by the upstream-side cutting device 113, a non-cut portion NTb corresponding to a length equal to the total length, in the article longitudinal direction Y, of the non-slit regions NT1 is formed intermittently in the continuous base sheet 2b being transported. The plurality of long base portions 2 formed in the central region by the downstream-side cutting device 117 in the cutting step are formed parallel to the transporting direction (Yd1 direction) and are arranged side by side in the orthogonal direction (Xd1 direction).

Next, an adhesive 5 is applied on the surface of first side of the long base portions 2 that have been formed in the cutting step (adhesive application step). In the present embodiment employing the manufacturing device 100, while the long base portions 2 that have been formed in the cutting step are being transported by the vacuum conveyor 141 and are located above the vacuum box 145, the application head 121 of the adhesive application unit 120 applies the adhesive 5 intermittently on the surface of the first side (upper surface) of the long base portions 2 formed side by side in the orthogonal direction (Xd1 direction), except in non-cut portions NTb.

Next, water-absorbent polymer particles 3 are dispersed on the adhesive 5 applied on the surface of the first side (upper surface) of the long base portions 2 formed in the adhesive application step (water-absorbent polymer particle dispersion step). In the present embodiment employing the manufacturing device 100, while the long base portions 2, which have the adhesive 5 applied on the surface of the first side (upper surface) in the adhesive application step, are being transported by the vacuum conveyor 141 and are located above the vacuum box 145, the water-absorbent polymer introduction unit 131 of the water-absorbent polymer dispersion unit 130 disperses the water-absorbent polymer particles 3 on the adhesive 5 applied on the surface of the first side (upper surface) of the long base portions 2 arranged side by side, except in the non-cut portions NTb. By dispersing the water-absorbent polymer particles 3 as described above, a plurality of absorbent units 4 are formed, wherein the water-absorbent polymer particles 3 are fixed to the surface of the respective long base portions 2 by means of the adhesive 5.

In the sheet-like article 1, the water-absorbent polymer particles 3 are fixed to the surfaces of both faces (upper and lower surfaces) of the respective long base portions 2. Thus, for example, the manufacturing device 100 illustrated in FIG. 18 can be used to: first fix the water-absorbent polymer particles 3 to the surface of first side (upper surface) of the respective long base portions 2; then flip the long base portions 2 over with an inversion roller; then disperse and fix water-absorbent polymer particles 3 onto the surface of the second side (lower surface) of the respective long base portions 2 by using a separate water-absorbent polymer dispersion unit 130, to thereby manufacture the sheet-like article.

A precursor 1b of the sheet-like article 1 is formed according to the above. In the precursor 1b of the sheet-like article 1 formed as above, the absorbent units 4 formed in the central region are arranged such that their longitudinal direction (y1 direction) is oriented in the transporting direction (Yd1 direction), and the absorbent units 4 formed in the side regions are arranged such that their longitudinal direction (y1 direction) is oriented in the orthogonal direction (Xd1 direction).

Then, the precursor 1b of the sheet-like article 1 is transported downstream by the drive roller 152, and, using a known cutting device (not illustrated), the precursor 1b is cut at every position located at half the length, in the transporting direction (Yd1 direction), of the non-cut portion NTb. In this way, sheet-like articles 1, each including respective non-slit regions NT at both end portions in the article longitudinal direction Y, are manufactured continuously. With the embodiment employing the manufacturing device 100, it is possible to manufacture sheet-like articles 1 stably and efficiently.

Further, according to the embodiment employing the manufacturing device 100, first, the long base portions 2 with a uniform width are formed by using the plurality of cutter blades 111a, 111a, 111a, . . . or the plurality of cutter blades 115a, 115a, 115a, . . . , and then, the adhesive 5 is applied on the surface of first side (upper surface) of the respective long base portions 2. Thus, the manufactured sheet-like article 1 is likely to be configured such that the long base portions 2, 2 of absorbent units which are formed adjacent to one another in the lateral direction (x1 direction) in the central region CT or the side regions ST are contiguous over their entirety. Such sheet-like articles 1 can be manufactured stably and efficiently.

The disposable diaper 10 which is an embodiment of the invention can be manufactured similarly to known methods for manufacturing pull-on disposable diapers according to the so-called cross-flow system, except that the sheet-like article 1 manufactured by using the manufacturing device 100 is used as the absorbent core 24. For example, while continuously transporting sheet-like articles 1 such that their longitudinal direction is in the flow direction (longitudinal flow), the entirety of each sheet-like article is covered by a continuous core-wrap Sheet 25, to form a continuous strip of absorbent members 23 in which the sheet-like articles 1 are arranged intermittently in the flow direction. Then, the upper surface of the continuous strip of the absorbent members 23 is covered by a topsheet member, which is formed by fixing sheet materials 27 to the respective lateral sides of a continuous topsheet 21, each sheet material 27 having been folded and having continuous thread-form elastic members 29a, 29b, 29c arranged therein. Also, the lower surface of the continuous strip of the absorbent members 23 is covered by a continuous backsheet 22. Then, both lateral sides, of the topsheet member, which extend along the flow direction (longitudinal flow) are wrapped downward onto the lower surface side of the continuous strip of the absorbent members 23, and these constituent members are fixed together. Then, the sheet-like articles 1 adjacent to one another in the flow direction (longitudinal flow) are cut therebetween, to continuously manufacture absorbent assemblies 20 in the flow direction (longitudinal flow). Thereafter, each of the absorbent assemblies 20 is turned 90 degrees, and is fixed by an adhesive, such as a hot-melt adhesive, onto an inner sheet 31 of a continuous outer cover 30 manufactured in a separate process, to thereby form a continuous strip of diaper 10. Next, leg holes are formed inside annular portions annularly surrounded by leg elastic members 33L in the continuous strip of the outer cover 30 on which the absorbent assemblies 20 have been arranged. Next, both lateral sides, in the flow direction, of the continuous strip of the outer cover 30 are superposed on one another, to fold the continuous strip of the outer cover 30 and each of the absorbent, assemblies 20 into two. Thereafter, side seals S are formed intermittently, and then cutting is performed at each, of the side seals 5, to thereby continuously manufacture diaper 10.

The invention is not limited to the foregoing embodiments and can be modified as appropriate.

As illustrated in FIGS. 16 and 17, the aforementioned sheet-like article 1, which is the absorbent core 24 of the diaper 10, is formed by using a plurality of absorbent units 4 including long base portions 2 with a uniform width in the central region CT and both side regions ST. The width of the long base portion 2, however, may be nonuniform. Preferably, in a planar view of the sheet-like article 1, the water-absorbent polymer particles 3 may be fixed in an unevenly distributed manner; and in a section where the basis weight of the fixed water-absorbent polymer 3 is relatively high, the distance between both lateral side edge portions 2s, 2s, of each long base portion 2, that extend along the longitudinal direction (y1 direction) may be relatively short. Stated differently, when comparing a section where the basis weight of the fixed water-absorbent polymer 3 is large and a section where the basis weight is small, the distance between each long base portion 2's both lateral side edge portions 2s, 2s in a section where the basis weight of the fixed water-absorbent polymer 3 is large may be made shorter than the distance between each long base portion 2's both lateral side edge portions 2s, 2s in a section where the basis weight of the fixed water-absorbent polymer 3 is small. With the sheet-like article 1 configured as above, in a section where the basis weight of the fixed water-absorbent polymer 3 is large, the adjacent absorbent units 4, 4 are facilitated to move freely in the thickness direction (Z direction; z1 direction) and the sheet-like article 1 is less likely to become stiff, and also, it is possible to make full use of the absorption performance of the water-absorbent polymer 3 and the absorption performance of the sheet-like article 1 is easily improved.

The aforementioned sheet-like article 1 of the diaper 10 illustrated in FIG. 17 is formed such that, in the central region CT, the absorbent units 4 are arranged such that their longitudinal direction (y1 direction) is oriented in the article longitudinal direction Y of the sheet-like article 1, but the absorbent units 4 may be arranged such that their longitudinal direction (y1 direction) is oriented in the article lateral direction X of the sheet-like article 1.

In the aforementioned sheet-like article 1 of the diaper 10 illustrated in FIG. 17, in each side region ST, the absorbent units 4 and the long base portions 2 extend rectilinearly parallel to the article lateral direction X, but their shape is not limited so long as they extend in the article lateral direction X. For example, the absorbent units 4 and the long base portions 2 may extend so as to repeatedly depict S shapes in the article lateral direction X, or may extend in a zig-zag form along the article lateral direction X.

Further, in the diaper 10 illustrated in FIGS. 16 and 20, the absorbent assembly 20 includes a pair of leak-proof cuffs 26, 26 in the respective lateral sides along the article longitudinal direction Y. The absorbent article of the invention, however, does not have to include a pair of leak-proof cuffs 26, 26. In cases where no pair of leak-proof cuffs 26, 26 is provided, the backsheet 22 or the inner sheet 31 constituting the outer cover 30 serves as the constituent member of the absorbent article on the non-skin-facing surface side to which the tip-end portion 21E1 of each extension portion 21E of the topsheet 21 is fixed.

Further, in the aforementioned method for manufacturing the sheet-like articles 1 of the foregoing embodiments, an adhesive application step is provided after the cutting step, and a water-absorbent polymer dispersion step is provided after the adhesive application step, but in cases where first side of the base sheet 2b is to be napped, a napping step may be provided instead of the adhesive application step. The napping step may be provided before the cutting step. Examples of methods for performing napping include methods described in JP 2012-092476 A and JP 2013-028891 A.

Other than the aforementioned disposable diaper 10, the absorbent article of the invention may be an article used for absorbing and retaining excreted body fluid such as urine or menstrual blood. Absorbent articles include, for example, open-type disposable diapers, sanitary napkins, and incontinence pads, but are not limited thereto, and widely encompass articles used for absorbing liquids excreted from the human body.

In relation to the foregoing embodiments, the following sheet-like articles and absorbent articles are further disclosed.

{1}
A sheet-like article for an absorbent article, the sheet-like article comprising
a plurality of absorbent units, each absorbent unit including
a long base portion having a lateral direction, a longitudinal direction that is longer than the lateral direction, and a thickness direction, and
water-absorbent polymer particles that are fixed to a surface of first side of the long base portion,
the absorbent units being arranged such that the absorbent unit's longitudinal direction is oriented at least in one direction, wherein:
when the water-absorbent polymer particles absorb a liquid, the water-absorbent polymer particles swell beyond the long base portion's lateral side edge portions that extend along the longitudinal direction, and a position, in the thickness direction, of each long base portion is varied from the position thereof before absorbing the liquid.

{2}
The sheet-like article as set forth in clause {1}, wherein, before the water-absorbent polymer particles absorb a liquid, the water-absorbent polymer particles are arranged in the vicinity of the long base portion's lateral side edge portions.

{3}
The sheet-like article as set forth in clause {1} or {2}, wherein, before the water-absorbent polymer particles absorb a liquid, the water-absorbent polymer particles protrude beyond the long base portion's lateral side edge portions.

{4}
The sheet-like article as set forth in any one of clauses {1} to {3}, wherein, before the water-absorbent polymer particles absorb a liquid, the long base portions which are adjacent to one another are at least partially contiguous.

{5}
The sheet-like article as set forth in any one of clauses {1} to {4}, wherein, before the water-absorbent polymer particles absorb a liquid, the long base portions which are adjacent to one another are contiguous over their entirety.

{6}
The sheet-like article as set forth in any one of clauses {1} to {5}, wherein the sheet-like article includes, in each of both end portions in the longitudinal direction, a non-slit region in which the plurality of long base portions are connected in the lateral direction.

{7}
The sheet-like article as set forth in any one of clauses {1} to {6}, wherein:
the sheet-like article includes, in each of both end portions in the longitudinal direction, a non-slit region in which the plurality of long base portions are connected in the lateral direction; and
no water-absorbent polymer particle is fixed in the non-slit regions.

{8}
The sheet-like article as set forth in any one of clauses {1} to {7}, wherein the sheet-like article's both end portions in the longitudinal direction are fixed to the absorbent article.

{9}

The sheet-like article as set forth in any one of clauses {1} to {8}, wherein a distance between the long base portion's both lateral side edge portions that extend along the longitudinal direction is greater than an average particle size of the water-absorbent polymer particles in a state before absorbing a liquid, and is smaller than an average particle size of the water-absorbent polymer particles in a swollen state after absorbing a liquid.

{10}

The sheet-like article as set forth in any one of clauses {1} to {9}, wherein the long base portions are hydrophilic.

{11}

The sheet-like article as set forth in any one of clauses {1} to {10}, wherein the long base portions are a nonwoven fabric.

{12}

The sheet-like article as set forth in any one of clauses {1} to {11}, wherein:
  in a planar view of the sheet-like article, the water-absorbent polymer particles are fixed in an unevenly distributed manner; and
  in a section where the basis weight of the fixed water-absorbent polymer particles is relatively high, the distance between the long base portion's both lateral side edge portions that extend along the longitudinal direction is relatively short.

{13}

The sheet-like article as set forth in any one of clauses {1} to {12}, wherein, before the water-absorbent polymer particles absorb a liquid, the water-absorbent polymer particles are fixed on a surface of the second side of each long base portion.

{14}

The sheet-like article as set forth in clause {13}, wherein a basis weight of the water-absorbent polymer particles fixed on the surface of the second side of the long base portions is greater than a basis weight of the water-absorbent polymer particles fixed on the surface of the first side of the long base portions.

{15}

The sheet-like article as set forth in clause {13} or {14}, wherein the water-absorbent polymer particles fixed on the surface of the first side of the long base portions have a higher liquid permeation performance under pressure and a smaller centrifugal retention amount than the water-absorbent polymer particles fixed on the surface of the second side of the long base portions.

{16}

The sheet-like article as set forth in any one of clauses {1} to {15}, wherein the water-absorbent polymer particles are fixed to the long base portions by an adhesive.

{17}

The sheet-like article as set forth in any one of clauses {1} to {16}, wherein there is no intervening member present between the absorbent units adjacent to one another in the lateral direction.

{18}

The sheet-like article as set forth in any one of clauses {1} to {17}, wherein a plurality of the absorbent units are arranged such that their longitudinal direction is oriented along the longitudinal direction of the sheet-like article.

{19}

The sheet-like article as set forth in clause {18}, wherein 3 pieces or more, preferably 50 pieces or more, and 1000 pieces or fewer, preferably 500 pieces or fewer, and more specifically, from 3 to 1000 pieces, preferably from 50 to 500 pieces, of the absorbent units are arranged in a single sheet-like article.

{20}

The sheet-like article as set forth in any one of clauses {1} to {17}, wherein:
  a plurality of the absorbent units are arranged such that their longitudinal direction is oriented along the lateral direction of the sheet-like article; and
  3 pieces or more, preferably 50 pieces or more, and 3500 pieces or fewer, preferably 2000 pieces or fewer, and more specifically, from 3 to 3500 pieces, preferably from 50 to 2000 pieces, of the absorbent units are arranged in a single sheet-like article.

{21}

The sheet-like article as set forth in any one of clauses {1} to {20}, wherein the length, in the lateral direction, of the absorbent unit is from 0.5 to 10 mm, preferably from 1 mm to 5 mm.

{22}

The sheet-like article as set forth in any one of clauses {1} to {21}, wherein the length, in the longitudinal direction, of the absorbent unit is from 20 to 200 times, preferably from 40 to 80 times the length, in the lateral direction, of the absorbent unit.

{23}

The sheet-like article as set forth in clause {22}, wherein the length, in the longitudinal direction, of the absorbent unit is from 10 to 500 mm, preferably from 200 to 400 mm.

{24}

The sheet-like article as set forth in any one of clauses {1} to {23}, wherein a ratio of the width of the long base portion to the width of the sheet-like article is 0.001 or greater, preferably 0.002 or greater, and 0.2 or less, preferably 0.04 or less, and more specifically from 0.001 to 0.2, preferably from 0.002 to 0.04.

{25}

The sheet-like article as set forth in any one of clauses {1} to {24}, wherein the width of the long base portion is 0.3 mm or greater, preferably 0.6 mm or greater, and 10 mm or less, preferably 2 mm or less, more preferably 1.8 mm or less, and more specifically from 0.3 to 10 mm, preferably from 0.6 to 2 mm, more preferably from 0.6 to 1.8 mm.

{26}

The sheet-like article as set forth in any one of clauses {1} to {25}, wherein another long base portion is arranged on the water-absorbent polymer particles, and the water-absorbent polymer particles are fixed by being sandwiched between two of the long base portions from above and below.

{27}

The sheet-like article as set forth in any one of clauses {1} to {25}, wherein a base sheet having a wider width than the long base portion is arranged on the water-absorbent polymer particles, and the water-absorbent polymer particles are fixed by being sandwiched between the long base portion and the base sheet.

{28}

An absorbent member for an absorbent article, the absorbent member comprising:
  the sheet-like article as set forth in any one of clauses {1} to {27}; and
  a liquid-permeable core-wrap sheet that covers the sheet-like article.

{29}
An absorbent article comprising:
the absorbent member as set forth in clause {28};
a topsheet arranged on a skin-facing surface side of the absorbent member; and
a backsheet arranged on a non-skin-facing surface side of the absorbent member.

{30}
A method for manufacturing a sheet-like article for an absorbent article, the sheet-like article comprising a plurality of absorbent units each including
a long base portion having a lateral direction, a longitudinal direction that is longer than the lateral direction, and a thickness direction, and
water-absorbent polymer particles that are fixed to a surface of first side of the long base portion,
the absorbent units being arranged such that the absorbent unit's longitudinal direction is oriented at least in one direction, wherein, when the water-absorbent polymer particles absorb a liquid, the water-absorbent polymer particles swell beyond the long base portion's lateral side edge portions that extend along the longitudinal direction, and a position, in the thickness direction, of each long base portion is varied from the position thereof before absorbing the liquid,
the method comprising:
a cutting step of cutting a continuous base sheet to thereby form a plurality of the long base portions; and
a water-absorbent polymer particle dispersion step of dispersing the water-absorbent polymer particles on the surface of the first side of the plurality of long base portions that have been formed.

{31}
The method for manufacturing a sheet-like article as set forth in clause {30}, wherein the method comprises, before the water-absorbent polymer particle dispersion step, an adhesive application step of applying an adhesive.

{32}
The method for manufacturing a sheet-like article as set forth in clause {31}, wherein:
the method comprises the adhesive application step after the cutting step, and the water-absorbent polymer particle dispersion step after the adhesive application step; and
the adhesive is applied in the adhesive application step on the surface of the first side of the long base portions that have been formed in the cutting step, and the water-absorbent polymer particles are dispersed in the water-absorbent polymer particle dispersion step on the adhesive that has been applied on the surface of the first side of the long base portions, to thereby form the sheet-like article in which the water-absorbent polymer particles are fixed by the adhesive to the long base portions.

{33}
The method for manufacturing a sheet-like article as set forth in any one of clauses {30} to {32}, wherein, in the cutting step, the continuous base sheet is cut along the base sheet's transporting direction at a plurality of sections in the cross direction, to form the plurality of long base portions.

{34}
The method for manufacturing a sheet-like article as set forth in any one of clauses {30} to {33}, wherein, in the cutting step, non-cut portions are formed in the continuous base sheet, the non-cut portions being arranged intermittently in the transporting direction of the base sheet.

{35}
The method for manufacturing a sheet-like article as set forth in clause {31} or {32}, wherein:
in the cutting step, non-cut portions are formed in the continuous base sheet, the non-cut portions being arranged intermittently in the transporting direction of the base sheet; and
in the adhesive application step, the adhesive is intermittently applied excluding the non-cut portions.

{36}
The method for manufacturing a sheet-like article as set forth in any one of clauses {30} to {35}, wherein:
in the cutting step, non-cut portions are formed in the continuous base sheet, the non-cut portions being arranged intermittently in the transporting direction of the base sheet; and
the water-absorbent polymer particles are dispersed excluding the non-cut portions.

{37}
The method for manufacturing a sheet-like article as set forth in any one of clauses {30} to {35}, wherein, after the water-absorbent polymer dispersion step, an adhesive is applied to the dispersed water-absorbent polymer particles.

{38}
The method for manufacturing a sheet-like article as set forth in any one of clauses {30} to {37}, wherein:
in the cutting step, the base sheet is cut to thereby form the plurality of long base portions;
an adhesive is applied on the surface of the first side of all of the long base portions that have been formed; and
the water-absorbent polymer particles are dispersed only on the adhesive applied on the surface of the first side of a plurality of the long base portions, among all of the long base portions, that are located on one side of a bisecting position where the base sheet is bisected in a cross direction and the water-absorbent polymer particles are thereby fixed to the long base portions by the adhesive, and then, a plurality of the long base portions that are located on the other side of the bisecting position and that have the adhesive applied on the surface of the first side are folded onto the water-absorbent polymer particles, to thereby obtain a sheet-like article in which the water-absorbent polymer particles are sandwiched between the long base portions.

{39}
The method for manufacturing a sheet-like article as set forth in any one of clauses {30} to {37}, wherein:
in the cutting step, the base sheet is cut to thereby form the plurality of long base portions;
an adhesive is applied on the surface of the first side of the long base portions;
the water-absorbent polymer particles are dispersed on the face, of the long base portions to which the adhesive has been applied, where the adhesive has been applied;
an adhesive is further applied onto the water-absorbent polymer particles that have been dispersed; and
second long base portions obtained by cutting a second base sheet are arranged on the adhesive applied onto the water-absorbent polymer particles, to thereby obtain a sheet-like article in which the water-absorbent polymer particles are sandwiched between the long base portions and the second long base portions.

{40}
The method for manufacturing a sheet-like article as set forth in any one of clauses {30} to {37}, wherein:
in the cutting step, the base sheet is cut to thereby form the plurality of long base portions;
an adhesive is applied on the surface of the first side of the long base portions;

the water-absorbent polymer particles are dispersed on the surface of the face, of the long base portions to which the adhesive has been applied, where the adhesive has been applied;

an adhesive is further applied onto the water-absorbent polymer particles that have been dispersed; and a second base sheet having a wider width than the long base portion is arranged on the adhesive applied onto the water-absorbent polymer particles, to thereby obtain a sheet-like article in which the water-absorbent polymer particles are sandwiched between the long base portions and the second base sheet.

{41}

The absorbent article as set forth in clause {29}, comprising an absorbent assembly including the topsheet, the backsheet, and the absorbent member interposed between the topsheet and the backsheet, the absorbent article having an article longitudinal direction corresponding to a wearer's front-to-rear direction, and an article lateral direction orthogonal to the article longitudinal direction, wherein:

the absorbent member includes an absorbent core formed of the sheet-like article comprising a plurality of the absorbent units, each absorbent unit including the long base portion having a lateral direction, a longitudinal direction that is longer than the lateral direction, and a thickness direction, and the water-absorbent polymer particles that are fixed to a surface of first side of the long base portion, the absorbent units being arranged such that the absorbent unit's longitudinal direction is oriented at least in one direction;

the absorbent core includes a central region in a central area in the article lateral direction, and a pair of side regions provided more outward, in the article lateral direction, than the central region;

in each side region, the absorbent units are arranged such that the absorbent unit's longitudinal direction is oriented in the article lateral direction;

the topsheet covers a skin-facing surface of the absorbent member, and includes extension portions extending outward, in the article lateral direction, from respective lateral side edge portions of the absorbent member, the extension portions being folded back toward a non-skin-facing surface side of the absorbent member and respectively covering the absorbent member's non-skin-facing surface located in the respective side regions of the absorbent core; and a tip-end portion of each folded-back extension portion of the topsheet is fixed to a constituent member of the absorbent article located adjacent to the extension portion.

{42}

The absorbent article as set forth in clause {41}, wherein an elastic member is provided to each of the lateral side edge portions of the absorbent member and is arranged along the lateral side edge portion, wherein a contractile force of the elastic member causes the absorbent member located in each side region of the absorbent core to stand up toward the wearer's skin side.

{43}

The absorbent article as set forth in clause {41} or {42}, wherein a distance between both lateral side edge portions, which extend along the longitudinal direction, of each absorbent unit's long base portion arranged in the absorbent core's side region is different from a distance between both lateral side edge portions, which extend along the longitudinal direction, of each absorbent unit's long base portion arranged in the absorbent core's central region.

{44}

The absorbent article as set forth in any one of clauses {41} to {43}, wherein, in the central region of the absorbent core, the absorbent units are arranged such that their longitudinal direction is oriented along the article longitudinal direction.

{45}

The absorbent article as set forth in any one of clauses {41} to {44}, wherein the basis weight of the water-absorbent polymer of the absorbent units arranged in the central region of the absorbent core is greater than the basis weight of the water-absorbent polymer of the absorbent units arranged in each side region of the absorbent core.

{46}

The absorbent article as set forth in any one of clauses {41} to {45}, wherein the position where the tip-end portion of the extension portion of the topsheet is joined to the constituent member of the absorbent article matches a position corresponding to a boundary between the central region and each side region of the absorbent core.

{47}

The absorbent article as set forth in any one of clauses {41} to {46}, wherein, when the absorbent core is in a state after swelling, the water-absorbent polymer particles swell beyond the long base portion's lateral side edge portions that extend along the longitudinal direction, and the respective positions, in the thickness direction, of the water-absorbent polymer particles in each long base portion differ from the positions thereof before absorbing the liquid.

{48}

The absorbent article as set forth in any one of clauses {41} to {47}, wherein:

the absorbent units are arranged in the central region of the absorbent core; and in a section where the absorbent units are arranged in the central region, the absorbent core is not fixed to the absorbent article.

{49}

The absorbent article as set forth in any one of clauses {41} to {48}, wherein both end portions, in the longitudinal direction, of the absorbent core are fixed to the absorbent article.

{50}

The absorbent article as set forth in any one of clauses {41} to {49}, wherein both lateral sides, of the absorbent core, that extend along the longitudinal direction are fixed to the absorbent article.

{51}

The absorbent article as set forth in any one of clauses {41} to {50}, wherein, in the absorbent core, the water-absorbent polymer particles are not fixed in both end portions in the longitudinal direction or in both lateral sides extending along the longitudinal direction.

{52}

The absorbent article as set forth in any one of clauses {41} to {51}, wherein the long base portions of the absorbent core are hydrophilic.

{53}

The absorbent article as set forth in any one of clauses {41} to {52}, wherein, in the absorbent core, the type of the water-absorbent polymer fixed on the surface of the first side of the long base portions is different from the type of the water-absorbent polymer fixed on the surface of the second side of the long base portions.

{54}

The absorbent article as set forth in any one of clauses {41} to {53}, wherein, in each side region, the plurality of absorbent units are arranged parallel to the article lateral direction X such that the absorbent units do not intersect with one another.

{55}

The absorbent article as set forth in any one of clauses {41} to {54}, wherein each side region is formed by using a plurality of the absorbent units respectively including long base portions with a uniform width, and by arranging the absorbent units side by side in the article longitudinal direction and parallel to the article lateral direction of the sheet-like article such that the longitudinal direction (y1 direction) of the absorbent units is oriented along the article lateral direction of the sheet-like article.

{56}

The absorbent article as set forth in any one of clauses {41} to {55}, wherein, in each side region, there is no intervening member present between the absorbent units adjacent to one another in the lateral direction (x1 direction) of the long base portion.

{57}

The absorbent article as set forth in any one of clauses {41} to {56}, wherein the central region is formed by arranging a plurality of absorbent units such that the longitudinal direction (y1 direction) of the absorbent units is oriented along the article longitudinal direction of the sheet-like article, and preferably, the absorbent units are arranged parallel to the article longitudinal direction Y such that the absorbent units do not intersect with one another.

{58}

The absorbent article as set forth in any one of clauses {41} to {57}, wherein, in the central region, there is no intervening member present between the absorbent units adjacent to one another in the lateral direction (x1 direction) of the long base portion.

{59}

The absorbent article as set forth in any one of clauses {41} to {58}, wherein:

in a state before use, the sheet-like article includes an absorbent region in which a plurality of the absorbent units are arranged so as to be oriented in one direction; and the percentage of the absorbent region to the entire sheet-like article is preferably 20% or greater, more preferably 50% or greater, and preferably 100% or less, more preferably 90% or less.

{60}

The absorbent article as set forth in any one of clauses {41} to {59}, wherein, in each side region, in cases where the longitudinal direction (y1 direction) of the absorbent units is arranged so as to be oriented along the article lateral direction X, it is preferable that 10 pieces or more, more preferably 50 pieces or more, and preferably 3500 pieces or fewer, more preferably 1700 pieces or fewer, of the absorbent units are arranged in each side region.

{61}

The absorbent article as set forth in any one of clauses {41} to {60}, wherein, in the central region, in cases where the longitudinal direction (y1 direction) of the absorbent units is arranged so as to be oriented along the article longitudinal direction Y, it is preferable that 2 pieces or more, more preferably 10 pieces or more, and preferably 1000 pieces or fewer, more preferably 500 pieces or fewer, of the absorbent units are arranged in the central region.

{62}

The absorbent article as set forth in any one of clauses {411 to 161}, wherein the width (length in the lateral direction (x1 direction)) of a single long base portion arranged in each side region is shorter than the width (length in the lateral direction (x1 direction)) of a single long base portion arranged in the central region.

{63}

The absorbent article as set forth in any one of clauses {41} to {62}, wherein, in the central region of the sheet-like article, the percentage of the width (length in the lateral direction (x1 direction)) of a single long base portion to the width of the sheet-like article is preferably 0.1% or greater, more preferably 0.2% or greater, and preferably 20% or less, more preferably 4% or less.

{64}

The absorbent article as set forth in any one of clauses {41} to {63}, wherein the width of the long base portion in the central region is preferably 0.3 mm or greater, more preferably 0.6 mm or greater, and preferably 10 mm or less, more preferably 2 mm or less.

{65}

The absorbent article as set forth in any one of clauses {41} to {64}, wherein, in the central region of the sheet-like article, the percentage of the length (length in the longitudinal direction (y1 direction)) of a single long base portion 2 to the length of the sheet-like article 1 is preferably 2% or greater, more preferably 20% or greater, and preferably 100% or less, more preferably 98% or less.

{66}

The absorbent article as set forth in any one of clauses {41} to {65}, wherein the length of the long base portion in the central region is preferably 20 mm or greater, more preferably 200 mm or greater, and preferably 1000 mm or less, more preferably 980 mm or less.

{67}

The absorbent article as set forth in any one of clauses {41} to {66}, wherein, in the side region, the percentage of the length (length in the longitudinal direction (y1 direction)) of a single long base portion to the width of the sheet-like article is preferably 1.5% or greater, more preferably 3% or greater, and preferably 47% or less, more preferably 40% or less.

{68}

The absorbent article as set forth in any one of clauses {41} to {67}, wherein the length of the long base portion in each side region is preferably 5 mm or greater, more preferably 10 mm or greater, and preferably 140 mm or less, more preferably 120 mm or less.

{69}

The absorbent article as set forth in any one of clauses {41} to {68}, wherein, in each side region of the sheet-like article, the percentage of the width (length in the lateral direction (x1 direction)) of a single long base portion to the length of the sheet-like article is preferably 0.03% or greater, more preferably 0.06% or greater, and preferably 10% or less, more preferably 2% or less.

{70}

The absorbent article as set forth in any one of clauses {41} to {69}, wherein the width of the long base portion in each side region is preferably 0.3 mm or greater, more preferably 0.6 mm or greater, and preferably 10 mm or less, more preferably 2 mm or less.

{71}

The absorbent article as set forth in any one of clauses {41} to {70}, wherein the basis weight of the water-absorbent polymer fixed to the surface of the first side of the long base portions is preferably from 10 to 250 g/m$^2$, and the basis weight of the water-absorbent polymer 3 fixed to the surface of the second side of the long base portions is preferably from 30 to 400 g/m².

{72}

The absorbent article as set forth in any one of clauses 1411 to 1711, wherein, as for the water-absorbent polymer fixed on the surface of the first side of the long base portions, the liquid permeation rate under a pressure of 2.0 kPa is preferably 20 ml/minute or greater, more preferably 40 ml/minute or greater, and preferably 1000 ml/minute or less, more preferably 800 ml/minute or less.

{73}

The absorbent article as set forth in any one of clauses {41} to {72}, wherein, as for the water-absorbent polymer particles fixed on the surface of the second side of the long base portions, the liquid permeation rate under a pressure of 2.0 kPa is preferably 0 ml/minute or greater, more preferably 10 ml/minute or greater, and preferably 400 ml/minute or less, more preferably 200 ml/minute or less.

{74}

The absorbent article as set forth in any one of clauses {41} to {73}, wherein, as for the water-absorbent polymer fixed on the surface of the first side of the long base portions, the centrifugal retention amount (water absorption amount) is preferably 20 g/g or greater, more preferably 25 g/g or greater, and preferably 50 g/g or less, more preferably 45 g/g or less.

{75}

The absorbent article as set forth in any one of clauses {41} to {74}, wherein, as for the water-absorbent polymer fixed on the surface of the second side of the long base portions, the centrifugal retention amount (water absorption amount) is preferably 25 g/g or greater, more preferably 30 g/g or greater, and preferably 65 g/g or less, more preferably 55 g/g or less.

{76}

The absorbent article as set forth in any one of clauses {41} to {75}, wherein, on the surfaces of both faces (upper surface and lower surface) of each long base portion, the basis weight of the water-absorbent polymer of the absorbent units arranged in the central region of the sheet-like article, which is the absorbent core, is greater than the basis weight of the water-absorbent polymer of the absorbent units arranged in each side region of the sheet-like article, which is the absorbent core.

{77}

The absorbent article as set forth in any one of clauses {41} to {76}, wherein the basis weight of the water-absorbent polymer of the absorbent units arranged in the central region is preferably from 30 to 400 g/m², more preferably from 50 to 300 g/m², per each face.

{78}

The absorbent article as set forth in any one of clauses {41} to {77}, wherein the basis weight of the water-absorbent polymer of the absorbent units arranged in each side region is preferably from 10 to 250 g/m², more preferably from 30 to 150 g/m², per each face.

{79}

The absorbent article as set forth in any one of clauses {41} to {78}, wherein, preferably, the distance between the long base portion's both lateral side edge portions that extend along the longitudinal direction (y1 direction) is greater than the average particle size of the water-absorbent polymer particles in a state before use (before swelling), and is smaller than the average particle size of the water-absorbent polymer particles in a state after swelling.

{80}

The absorbent article as set forth in any one of clauses {41} to {79}, wherein the average particle size of the water-absorbent polymer particles in a state before use (before swelling) is preferably 20 μm or greater, more preferably 200 μm or greater, and preferably 700 μm or less, more preferably 500 μm or less.

{81}

The absorbent article as set forth in any one of clauses {41} to {80}, wherein the average particle size of the water-absorbent polymer in a state after swelling is preferably 200 μm or greater, more preferably 800 μm or greater, and preferably 3000 μm or less, more preferably 2000 μm or less.

INDUSTRIAL APPLICABILITY

The present invention provides a sheet-like article in which inhibition by swelling is less likely to occur, and in which the absorption performance of water-absorbent polymers can be put to full use. Further, the present invention provides a sheet-like article manufacturing method with which such sheet-like articles can be manufactured efficiently.

The present invention provides an absorbent article in which the absorbent member in the side sections can easily stand up, thereby improving fittability and leakage-preventing performance in the crotch portion, and the absorbent member whose side sections have stood up is less likely to cause uncomfortableness.

The invention claimed is:

1. A sheet-like article for an absorbent article, the sheet-like article comprising
    a plurality of absorbent units, each absorbent unit including
        a long base portion having a lateral direction, a longitudinal direction that is longer than the lateral direction, and a thickness direction, and
        water-absorbent polymer particles that are fixed to a surface of a first side of the long base portion, wherein, before the water-absorbent polymer particles absorb a liquid, the water-absorbent polymer particles protrude beyond lateral side edge portions of the long base portion,
    the absorbent units being arranged such that the absorbent unit's longitudinal direction is oriented at least in one direction,
    wherein:
    when the water-absorbent polymer particles absorb a liquid, the water-absorbent polymer particles swell beyond the long base portion's lateral side edge portions that extend along the longitudinal direction, and a position, in the thickness direction, of each long base portion is varied from the position thereof before absorbing the liquid,
    a distance between the long base portion's both lateral side edge portions that extend along the longitudinal direction is greater than an average particle size of the water-absorbent polymer particles in a state before absorbing a liquid, and
    a distance between the long base portion's both lateral side edge portions that extend along the longitudinal direction is smaller than an average particle size of the water-absorbent polymer particles in a swollen state after absorbing a liquid.

2. The sheet-like article according to claim 1, wherein the sheet-like article includes, in each of both end portions in the longitudinal direction, a non-slit region in which the plurality of long base portions are connected in the lateral direction.

3. The sheet-like article according to claim 1, wherein the sheet-like article's both end portions in the longitudinal direction are fixed to the absorbent article.

4. The sheet-like article according to claim 1, wherein the long base portions are a nonwoven fabric.

5. The sheet-like article according to claim 1, wherein the water-absorbent polymer particles are fixed to the long base portions by an adhesive.

6. The sheet-like article according to claim 1, wherein:
the sheet-like article includes, in each of both end portions in the longitudinal direction, a non-slit region in which the plurality of long base portions are connected in the lateral direction; and
no water-absorbent polymer particle is fixed in the non-slit regions.

7. The sheet-like article according to claim 1, wherein there is no intervening member present between the absorbent units adjacent to one another in the lateral direction.

8. The sheet-like article according to claim 1, wherein another long base portion is arranged on the water-absorbent polymer particles, and the water-absorbent polymer particles are fixed by being sandwiched between two of the long base portions from above and below.

9. The sheet-like article according to claim 1, wherein a base sheet having a wider width than the long base portion is arranged on the water-absorbent polymer particles, and the water-absorbent polymer particles are fixed by being sandwiched between the long base portion and the base sheet.

10. An absorbent member for an absorbent article, the absorbent member comprising:
the sheet-like article according to claim 1; and
a liquid-permeable core-wrap sheet that covers the sheet-like article.

11. An absorbent article comprising:
the absorbent member according to claim 10;
a topsheet arranged on a skin-facing surface side of the absorbent member; and
a backsheet arranged on a non-skin-facing surface side of the absorbent member.

12. The absorbent article according to claim 11, comprising
an absorbent assembly including the topsheet, the backsheet, and the absorbent member interposed between the topsheet and the backsheet, the absorbent article having an article longitudinal direction corresponding to a wearer's front-to-rear direction, and an article lateral direction orthogonal to the article longitudinal direction, wherein:
the absorbent member includes an absorbent core formed of the sheet-like article comprising
a plurality of the absorbent units, each absorbent unit including
the long base portion having a lateral direction, a longitudinal direction that is longer than the lateral direction, and a thickness direction, and
the water-absorbent polymer particles that are fixed to a surface of first side of the long base portion,
the absorbent units being arranged such that the absorbent unit's longitudinal direction is oriented at least in one direction;
the absorbent core includes a central region in a central area in the article lateral direction, and a pair of side regions provided more outward, in the article lateral direction, than the central region;
in each side region, the absorbent units are arranged such that the absorbent unit's longitudinal direction is oriented in the article lateral direction;
the topsheet covers a skin-facing surface of the absorbent member, and includes extension portions extending outward, in the article lateral direction, from respective lateral side edge portions of the absorbent member, the extension portions being folded back toward a non-skin-facing surface side of the absorbent member and respectively covering the absorbent member's non-skin-facing surface located in the respective side regions of the absorbent core; and
a tip-end portion of each folded-back extension portion of the topsheet is fixed to a constituent member of the absorbent article located adjacent to the extension portion.

13. A sheet-like article for an absorbent article, the sheet-like article comprising
a plurality of absorbent units, each absorbent unit including a long base portion having a lateral direction, a longitudinal direction that is longer than the lateral direction, and a thickness direction, and water-absorbent polymer particles that are fixed to a surface of a first side of the long base portion, the absorbent units being arranged such that the absorbent unit's longitudinal direction is oriented at least in one direction, and,
in each of both end portions in the longitudinal direction, a non-slit region in which the plurality of long base portions are connected in the lateral direction, no water-absorbent polymer particle being fixed in the non-slit regions, wherein,
before the water-absorbent polymer particles absorb a liquid, the water-absorbent polymer particles protrude beyond lateral side edge portions of the long base portion,
when the water-absorbent polymer particles absorb a liquid, the water-absorbent polymer particles swell beyond the long base portion's lateral side edge portions that extend along the longitudinal direction, and a position, in the thickness direction, of each long base portion is varied from the position thereof before absorbing the liquid, and
a distance between the long base portion's both lateral side edge portions that extend along the longitudinal direction is greater than an average particle size of the water-absorbent polymer particles in a state before absorbing a liquid.

14. An absorbent member for an absorbent article, the absorbent member comprising:
the sheet-like article according to claim 13; and
a liquid-permeable core-wrap sheet that covers the sheet-like article.

15. An absorbent article comprising:
the absorbent member according to claim 14;
a topsheet arranged on a skin-facing surface side of the absorbent member; and
a backsheet arranged on a non-skin-facing surface side of the absorbent member.

* * * * *